(12) United States Patent
Liu et al.

(10) Patent No.: US 8,025,879 B2
(45) Date of Patent: Sep. 27, 2011

(54) MODIFIED GLYCOPROTEINS AND USES THEREOF

(75) Inventors: Cheng Liu, Richmond, CA (US); Jingyi Xiang, Walnut Creek, CA (US); Su Yan, Albany, CA (US); Pei Wang, Fremont, CA (US); Wei Chan Tai, Emeryville, CA (US)

(73) Assignee: Eureka Therapeutics, Inc., Emeryville, CA (US)

( * ) Notice: Subject to any disclaimer, the term of this patent is extended or adjusted under 35 U.S.C. 154(b) by 0 days.

(21) Appl. No.: 12/507,044

(22) Filed: Jul. 21, 2009

(65) Prior Publication Data

US 2010/0081794 A1    Apr. 1, 2010

Related U.S. Application Data

(60) Provisional application No. 61/194,292, filed on Sep. 26, 2008, provisional application No. 61/120,722, filed on Dec. 8, 2008, provisional application No. 61/168,186, filed on Apr. 9, 2009.

(51) Int. Cl.
*C07K 14/00* (2006.01)
*C07K 16/18* (2006.01)

(52) U.S. Cl. .................. 424/133.1; 530/387.3; 530/395

(58) Field of Classification Search ............... 424/133.1; 530/387.3, 395
See application file for complete search history.

(56) References Cited

U.S. PATENT DOCUMENTS

| | | |
|---|---|---|
| 6,602,684 B1 | 8/2003 | Umana et al. |
| 6,737,056 B1 | 5/2004 | Presta |
| 6,946,292 B2 | 9/2005 | Kanda et al. |
| 7,393,683 B2 | 7/2008 | Kanda et al. |
| 7,416,727 B2 | 8/2008 | Presta |
| 7,425,446 B2 | 9/2008 | Kanda et al. |
| 2004/0072290 A1 | 4/2004 | Umana et al. |
| 2005/0074843 A1 | 4/2005 | Umana et al. |
| 2005/0079605 A1 | 4/2005 | Umana et al. |
| 2005/0272128 A1 | 12/2005 | Umana et al. |
| 2005/0272916 A1 | 12/2005 | Hanai et al. |
| 2006/0064781 A1 | 3/2006 | Kanda et al. |
| 2006/0182741 A1 | 8/2006 | Bourel et al. |
| 2007/0015239 A1 | 1/2007 | Bihoreau et al. |
| 2008/0118501 A1 | 5/2008 | Schindler et al. |
| 2008/0280322 A9 | 11/2008 | Umana et al. |
| 2009/0285830 A1 | 11/2009 | Adams et al. |
| 2010/0081150 A1 | 4/2010 | Liu et al. |
| 2010/0081172 A1* | 4/2010 | Liu et al. ...................... 435/69.6 |
| 2010/0081195 A1 | 4/2010 | Liu et al. |
| 2011/0059075 A1 | 3/2011 | Wittrup et al. |

FOREIGN PATENT DOCUMENTS

| | | |
|---|---|---|
| EP | 1176195 A1 | 1/2002 |
| EP | 1331266 A1 | 7/2003 |
| EP | 1176195 A4 | 3/2005 |
| EP | 1914244 A2 | 4/2008 |
| EP | 1914244 A3 | 6/2008 |
| JP | 2008113663 A | 5/2008 |
| WO | WO 2005/012358 A2 | 2/2005 |
| WO | WO 2005/040221 A1 | 5/2005 |
| WO | WO 2005/012358 A3 | 9/2005 |
| WO | WO 2006/014679 A1 | 2/2006 |
| WO | WO 2006/014685 A1 | 2/2006 |
| WO | WO 2006/133148 A2 | 12/2006 |
| WO | WO 2007/028144 A2 | 3/2007 |
| WO | WO 2007/029054 A1 | 3/2007 |
| WO | WO 2007/048077 A2 | 4/2007 |
| WO | WO 2006/133148 A3 | 5/2007 |
| WO | WO 2007/053767 A1 | 5/2007 |
| WO | WO 2007/028144 A3 | 6/2007 |
| WO | WO 2007/048077 A3 | 7/2007 |
| WO | WO 2007/084672 A2 | 7/2007 |
| WO | WO 2007/084672 A3 | 10/2007 |
| WO | WO 2007/146847 A2 | 12/2007 |
| WO | WO 2007/146847 A3 | 11/2008 |

OTHER PUBLICATIONS

Wright et al (Springer Semin Immunopathology ,15 :259-273 (1993)).*
Delente (Trends in Biotechnology 3, letters to editor, No. 9, (1985)).*
Olden et al (Biochem et Biophys Acta 650:209-232 (1982)).*
Perkel et al. (Proc. Soc. Exp. Biol. Med. Mar. 1989;190(3):286-93; Abstract).*
Banerjee, et al. The evolution of N-glycan-dependent endoplasmic reticulum quality control factors for glycoprotein folding and degradation. Proc Natl Acad Sci U S A. Jul. 10, 2007;104(28):11676-81.
Czlapinski, et al. Synthetic glycobiology: Exploits in the Golgi compartment. Curr Opin Chem Biol. Dec. 2006;10(6):645-51.
International search report dated Nov. 24, 2009 for PCT Application No. US2009/51325.
Lowe, et al. A genetic approach to Mammalian glycan function. Annu Rev Biochem. 2003;72:643-91.
Natsume, et al. Fucose removal from complex-type oligosaccharide enhances the antibody-dependent cellular cytotoxicity of single-gene-encoded bispecific antibody comprising of two single-chain antibodies linked to the antibody constant region. J Biochem. Sep. 2006;140(3):359-68.

(Continued)

*Primary Examiner* — Lynn Bristol
(74) *Attorney, Agent, or Firm* — Wilson Sonsini Goodrich & Rosati

(57) ABSTRACT

The present disclosure provides compositions and methods comprising cells producing glycoproteins with variant glycosylation patterns. The methods and compositions may be used in producing antibodies and proteins of therapeutic value.

6 Claims, 33 Drawing Sheets

OTHER PUBLICATIONS

Sallustio, et al. Novel genetic instability associated with a developmentally regulated glycosyltransferase locus in Chinese hamster ovary cells. Somat Cell Mol Genet. Sep. 1989;15(5):387-400.

Shields, et al. Lack of fucose on human IgG1 N-linked oligosaccharide improves binding to human Fcgamma RIII and antibody-dependent cellular toxicity. J Biol Chem. Jul. 26, 2002;277(30):26733-40.

Shinkawa, et al. The absence of fucose but not the presence of galactose or bisecting N-acetylglucosamine of human IgG1 complex-type oligosaccharides shows the critical role of enhancing antibody-dependent cellular cytotoxicity. J Biol Chem. Jan. 31, 2003;278(5):3466-73.

Yamane-Ohnuki, et al. Establishment of FUT8 knockout Chinese hamster ovary cells: an ideal host cell line for producing completely defucosylated antibodies with enhanced antibody-dependent cellular cytotoxicity. Biotechnol Bioeng. Sep. 5, 2004;87(5):614-22.

Culture medium definition. Dictionary.com. Accessed May 4, 2011.

Fermentor definition. Dictionary.com. Accessed May 4, 2011.

Jones, et al. Controlling N-linked glycan site occupancy. Biochim Biophys Acta. Nov. 15, 2005;1726(2):121-37.

* cited by examiner

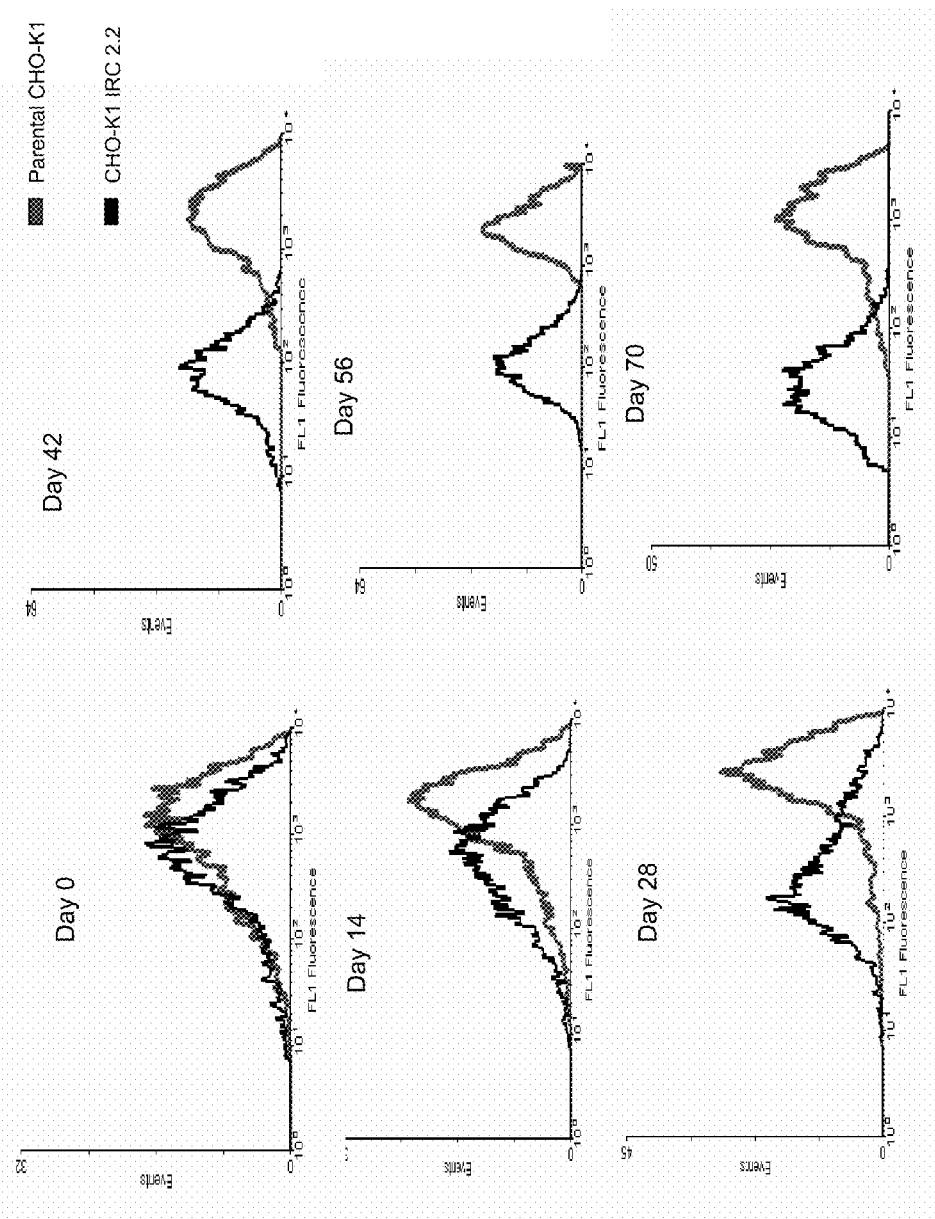

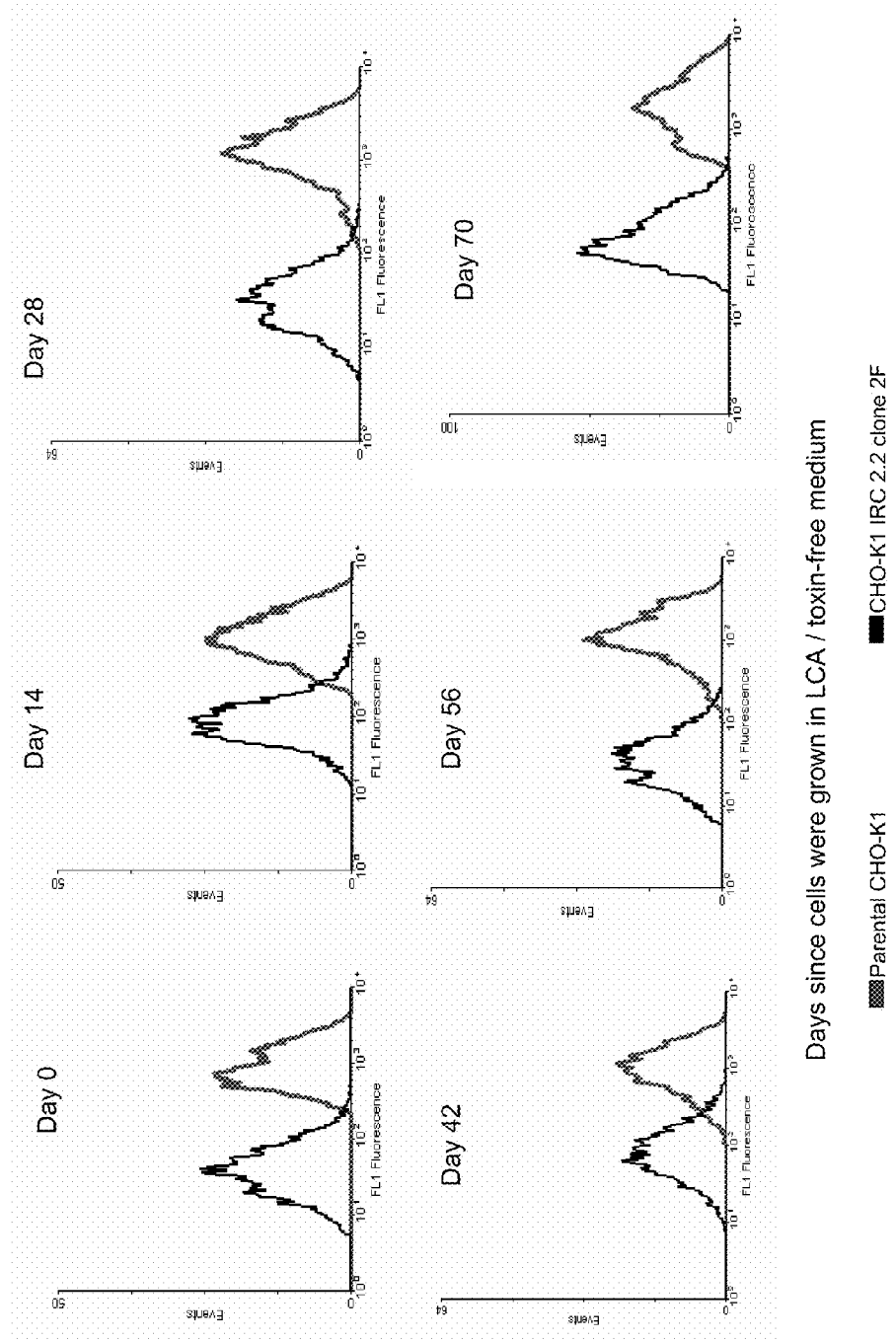

| | Fucose | GlcNac | Galactose | Glucose | Mannose |
|---|---|---|---|---|---|
| Wild Type Cells | | | | | |
| CHO-ET101 | + | + | + | - | + |
| CHO-ET201 | + | + | + | - | + |
| Mutant Clones | | | | | |
| CHO-1E5-ET101 | +/- | +/- | - | + | + |
| CHO-2.6-ET101 | +/- | +/- | - | +/- | + |
| CHO-3F-ET101 | +/- | +/- | - | + | + |
| CHO-2.6-ET201 | +/- | +/- | - | +/- | + |
| CHO-3F-ET201 | +/- | +/- | - | + | + |

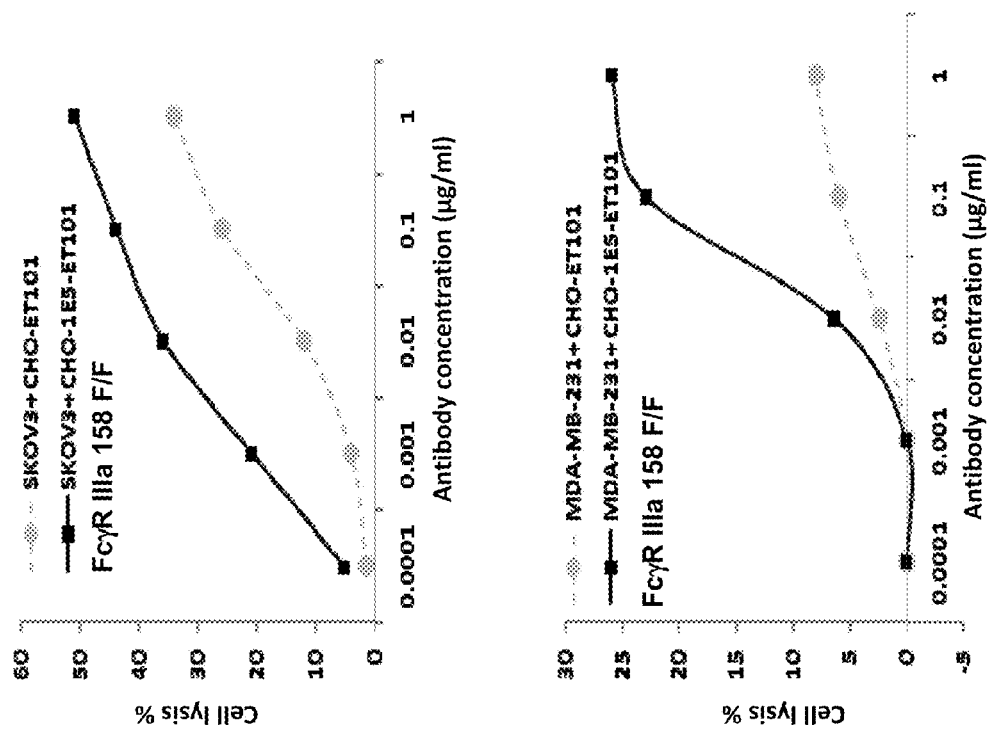

MODIFIED GLYCOPROTEINS AND USES THEREOF

CROSS-REFERENCE

This application claims priority to U.S. Ser. Nos. 61/194,292 filed on Sep. 26, 2008, 61/120,722 filed on Dec. 8, 2008, and 61/168,186 filed on Apr. 9, 2009, all of which are incorporated herein in their entirety for all purposes.

BACKGROUND

Variations in composition of the carbohydrate, saccharide, or sugar molecule, have been shown to affect the affinity of IgG for three classes of FcγRs (FcγRI, FcγRII, and FcγRIII) that link IgG-mediated immune response with cellular effector functions (Wright and Morrison, *Trends Biotechnol* 15(1): 26-32; Gessner et al., *Ann Hematol* 76(6): 231-48 (1998); Jefferis et al, *Immunol Rev* 163: 59-76 (1998). Ravetch and Bolland, *Annu Rev Immunol* 19: 275-90 (2001)).

Sugar chains of glycoproteins are generally divided into the following two broad types based on the binding form to a proteinaceous moiety: namely a sugar chain which binds to asparagine (N-glycoside-linked sugar chain), and a sugar chain which binds to other amino acids, such as serine or threonine (O-glycoside-linked sugar chain). Typically, they have a basic common core structure shown by the following structural formula (I):

(I)

The N-glycoside-linked sugar chains have various structures, with various sugar molecules. The sugar chain terminus which binds to asparagine is typically called a reducing end, and the opposite side is called a non-reducing end. N-glycoside-linked sugar chains can include a high mannose type in which mannose alone binds to the non-reducing end of the core structure; a complex type in which the non-reducing end side of the core structure has at least one parallel branch of galactose-N-acetylglucosamine (Gal-GlcNAc) and the non-reducing end side of Gal-GlcNAc has a structure of sialic acid, bisecting N-acetylglucosamine or the like; a hybrid type in which the non-reducing end side of the core structure has branches of both of the high mannose type and complex type; and the like. The structure of a sugar chain can be determined by sugar chain genes, such as a gene for a glycosyltransferase which synthesizes a sugar chain, and/or a gene for a glycolytic enzyme which hydrolyzes the sugar chain.

Glycoproteins are typically modified with a sugar chain in the endoplasmic reticulum (ER) lumen. For example, during the biosynthesis step of the N-glycoside-linked sugar chain, a relatively large sugar chain is transferred to a polypeptide chain that is elongating in the ER lumen. Sugar molecules can be added in succession to phosphate groups of a long chain lipid carrier comprising about 20 α-isoprene units, such as dolichol phosphate (P-Dol). For example, N-acetylglucosamine (GlcNAc) is transferred to P-Dol to form GlcNAc-P-P-Dol and then one more GlcNAc is transferred to form GlcNAc-GlcNAc-P-P-Dol. Next, five mannoses (Man) are transferred to thereby form $(Man)_5$-$(GlcNAc)_2$-P-P-Dol and then four Man's and three glucoses (Glc) are transferred. As a result, a sugar chain precursor, $(Glc)_3$-$(Man)_9$-$(GlcNAc)_2$-P-P-Dol, a core oligosaccharide, is formed. The sugar chain precursor comprising 14 sugars can then be transferred to a polypeptide having an asparagine-X-serine or asparagine-X-threonine sequence in the ER lumen. The dolichol pyrophosphate (P-P-Dol) bound to the core oligosaccharide is typically released and becomes dolichol phosphate (P-Dol) by hydrolysis with pyrophosphatase, and is recycled. Trimming of the sugar chain typically starts after the sugar chain binds to the polypeptide. For example, 3 Glc's and 1 or 2 Man's are eliminated on the ER, such as by the action of α-1,2-glucosidase I, α-1,3-glucosidase II and α-1,2-mannosidase.

The glycoprotein which was subjected to trimming on the ER can be transferred to the Golgi body and further modified. For example, present in the cis part of the Golgi body are N-acetylglucosamine phosphotransferase (which aids in the addition of mannose phosphate), N-acetylglucosamine 1-phosphodiester α-N-acetylglucosamimidase and α-mannosidase I (which reduce the Man residues to 5). Present in the medium part of the Golgi body are N-acetylglucosamine transferase I (GnTI) (which aids in the addition of the first outside GlcNAc of the complex type N-glycoside-linked sugar chain), α-mannosidase II (which aids in the removal of 2 Man's), N-acetylglucosamine transferase II (GnTII) (which aids in the addition of the second GlcNAc from the outside) and α-1,6-fucosyltransferase (which aids in the addition of fucose to the reducing end N-acetylglucosamine). Present in the trans part of the Golgi body are galactose transferase, which aids in the addition of galactose, and sialyltransferase, which relates to addition of sialic acid such as N-acetylneuraminic acid or the like. Thus, various N-glycoside-linked sugar chains can be formed by activities of these various enzymes.

Sugar chain structure variations, or variant glycosylation patterns due to various sugar molecule content in such chains, plays an important role in the effector function of glycoproteins, such as antibodies. For example, in the Fc region of an antibody of an IgG type, two N-glycoside-linked sugar chain binding sites are typically present. In serum IgG, the sugar chain binding site generally binds a complex type sugar chain having multiple branches, and in which addition of sialic acid or bisecting N-acetylglucosamine is low. There are a variety of manners and forms in which addition of galactose is made to the non-reducing end of the complex type sugar chain and the addition of fucose to the N-acetylglucosamine in the reducing end (see for example, Leppanen et al., *Biochemistry,* 36, 7026-7036 (1997)).

Fucosylation is an example of a process in which newly synthesized antibodies can be modified by the addition of fucose saccharides in the Golgi apparatus of a cell. This protein modification can be visualized by staining the cells with fluorophore-conjugated LCA (Lens culimaris agglutinin-A), a chemical that preferentially binds to proteins modified with fucose. Recently, it has been observed that fucosylation of antibodies affects antibody binding to human FcγR and antibody-dependent cellular cytotoxicity (ADCC). Antibody-binding affinity and antibody-mediated ADCC is strongly enhanced when antibodies have low levels of fucose (Shields et al, *J Biol Chem* 277(30): 26733-4 (2002); Shinkawa et al, *J Biol Chem* 278(5): 3466-73 (2003)).

Protein fucosylation is a process that begins with the uptake of free fucose, followed by phosphorylation by fucose kinase and conversion to GDP-fucose by GDP-fucose pyrophosphorylase. Fucosyltransferases transfer the fucose residue to glycans or protein within secretary pathways, subsequently the modified glycoproteins are delivered to the cell surface for secretion. The fucosylation status of antibody-producing cells correlates with the fucose content in the antibody produced, and that the absence of fucosyltransferase abrogated the fucosylation at both cellular and antibody levels (Yamane-Ohnuki et al, *Biotechnol Bioeng* 87(5): 614-22 (2004)).

ADCC is an important mechanism of action by which therapeutic antibodies induce immune responses and mediate the killing of cancer cells. Enhancement of ADCC by therapeutic antibodies can improve clinical responses and reduce the therapeutic dosages, thus diminishing possible side effects (Adams and Weiner, *Nat Biotechnol* 23(9): 1147-57 (2005)). In vivo models and clinical trials have demonstrated that therapeutic antibodies, such as Herceptin, possess cytotoxic properties, including ADCC. These properties are main factors in Herceptin induced breast tumor regression and protection from lung metastasis (Carter et al, *Proc Natl Acad Sci USA* 89(10): 4285-9 (1992); Lewis et al, *Cancer Immunol Immunother* 37(4): 255-63 (1993); Cooley et al, *Exp Hematol* 27(10): 1533-41 (1999); Clynes et al, *Nat Med* 6(4): 443-6 (2000); Repka et al., *Clin Cancer Res* 9(7): 2440-6 (2003); Gennari et al, *Clin Cancer Res* 10(17): 5650-5 (2004); Nahta and Esteva, *Cancer Lett* 232(2): 123-38 (2006)). Further, it was demonstrated that antibodies produced by fucosylation-low cells enhance ADCC activity (Shields et al., *J Biol Chem* 277(30): 26733-4 (2002); Shinkawa et al., *J Biol Chem* 278 (5): 3466-73 (2003)).

Expression of ADCC activity of human IgG1 subclass antibodies typically requires binding of the Fc region of an antibody to an antibody receptor existing on the surface of an effector cell, such as a killer cell, a natural killer cell, an activated macrophage or the like (FcγR) and various complement components. It has been suggested that several amino acid residues in the second domain of the antibody hinge region and C region (hereinafter referred to as "Cγ2 domain") and a sugar chain linked to the Cγ2 domain are important for this binding reaction.

Currently, several strategies have been proposed for enhancing monoclonal antibody-mediated ADCC against tumor cells, such as: 1) developing specific anti-cancer antibodies in which one arm of the antibody binds to an IgG receptor in order to more efficiently recruit immune effector cells (Segal et al., *J Immunol Methods* 248(1-2): 1-6 (2001)); 2) using recombinant human cytokines to increase the effector function of immune effector cells (Carson et al, *Eur J Immunol* 31(10): 3016-25 (2001); Repka et al., *Clin Cancer Res* 9(7) 2440-6 (2003)); 3) using IgG-cytokine fusion protein (Penichet and Morrison, *J Immunol Methods* 248(1-2): 91-101 (2001)); 4) altering the Fc sequence of an antibody for improved binding to an IgG receptor (Shields et al, *J Biol Chem* 276(9): 6591-604 (2001)); and 5) optimization of the levels of Asn297-linked carbohydrates (Umana et al, *Nat Biotechnol* 17(2): 176-80 (1999); Davies et al., *Biotechnol Bioeng* 74(4): 288-94 (2001); Shinkawa et al, *J Biol Chem* 278(5): 3466-73 (2003)).

One approach is to modify the fucose content of anticancer antibodies to increase binding affinity for FcγRs and ADCC. IgG1 has two N-linked oligossacharide chains bound to Asn297, composed of a trimannosyl core structure with the presence or absence of a core fucose, bisecting N-acetylglucosamine and terminal galactose (Rademacher et al, *Biochem Soc Symp* 51: 131-48 (1986)). The nature and importance of Asn297-linked carbohydrates in immunoglobulin G effector functions has long been recognized. It has been demonstrated that defucosylated Rituxan, an anti-CD20 antibody for lymphoma treatment, strongly binds to FcγRIIIa with high affinity and 100-fold enhanced ADCC activity (Shinkawa et al, *J Biol Chem* 278(5):3466-73 (2003); Yamane-Ohnuki et al, *Biotechnol Bioeng* 87(5): 614-22 (2004); Kanda et al, *Biotechnol Bioeng* 94(4): 680-8 (2006)). Others have shown that binding low-fucose Herceptin to FcγRIIIa was improved by about 50-fold over normal-fucose Herceptin, and as a result, Herceptin-mediated-ADCC was substantially improved (Shields et al, *J Biol Chem* 277(30): 26733-40 (2002)). This indicates that defucosylation of anti-cancer antibodies increases their binding affinity to FcγR and enhances ADCC. Further, it suggests that modification of fucose content represents a way to improve anti-cancer immune response of antibodies so as to augment their therapeutic efficacy and expand the treatment to cancer patients that are unresponsive to fucosylated antibodies.

However, there remains a need for alternative methods for modifying antibodies of high therapeutic potential.

SUMMARY OF THE INVENTION

There exists a need to produce therapeutic proteins with increased effector functions. The present disclosure provides methods and compositions to meet this need, as well as related advantages, by producing cells lines and glycoproteins with variant glycosylation patterns, or glycoslyation patterns that are modified in comparison to a corresponding wildtype protein, or protein produced in a cell line with an unmodified glycosylation pattern. The differences in the sugar chain content of glycoproteins expressed by host cells and development of a host cell which can be used for the production of these glycoproteins with variant glycosylation patterns, such as an antibody, can have higher effector function.

In one embodiment, provided herein are methods and compositions for producing and selecting a host cell that is modified to yield a variant glycosylation pattern as compared to an unmodified parental host cell. The method of selecting a host cell with a variant glycosylation pattern may comprise providing a plurality of host cells; introducing random genetic mutation(s) to the plurality of host cells; and selecting from the plurality of cells at least one cell that exhibits a variant glycosylation pattern characterized by a change in the level of at least one type of sugar molecules as compared to a corresponding parental cell that has not been subject to said random genetic mutation. Furthermore, the genetic mutation(s) may be induced by a chemical mutagen.

The host cell may be a eukaryotic cell, such as a mammalian cell. The modified host cell can be a Chinese Hamster Ovarian (CHO) cell. The host cell may be a modified CHO cell, such as a CHO-1E5, CHO-3F, or CHO-2.6 cell. The host cell may also be a myeloma cell. The modified host cell can be an NS0, SP2/0, HEK293, PER.C6, or YB2/0 cell. The host cell that is modified exhibits a variant glycosylation pattern that can be characterized by a change in levels of at least two types of sugar molecules present on a surface of the host cell as compared to an unmodified parental host cell. The change in level can be at least approximately one-, two-, three-, four-, five-, six-, seven-, eight-, nine-, ten-fold or higher. The variant glycosylation pattern can be evidenced by a change in level of fucosylation, mannosylation, N-acetylglucosaminylation, or combinations thereof. In some embodiments, the change can be in the level of galactose, glucose, or both. The change can be an increase or a decrease in levels of galactose, glucose or both. For example, the change can be an increase in glucose and a decrease in galactose.

In some embodiments, the change in level may be a reduction in the level of fucosylation of the modified host cell as compared to the unmodified parental host cell. The variant glycosylation pattern can also be evidenced by a change in level of mannosylation, such as level of α-linked mannose. The level of mannosylation may be increased in the modified host cell. The variant glycosylation pattern can also be evidenced by a change in level of N-acetylglucosaminylation, such as a decrease or increase of N-acetylglucosaminylation in the modified host cell. The N-acetylglucosaminylation may involve α- or β-linked N-acetylglucosamine. The host cell that is modified to yield a variant glycosylation pattern as compared to an unmodified parental host may have 1,6-fucosyltransferase activity comparable to that of the unmodified parental host cell. In another aspect, the modified host cell can maintain its variant glycosylation pattern after at least approximately 30, 40, 50, 60, 80, 100, 120, 150, 200, 1000 or more passages. The modified host cell may also be grown in a serum-free medium, in suspension, and/or in a fermentor.

In another aspect, the present invention provides a population of antibodies produced by a modified non-lymphocytic host cell that produces antibodies exhibiting a substantially homogeneous pattern of N-linked glycan, wherein members of said population bind at least two distinct antigens.

In another aspect, the present invention provides a modified host cell that produces N-linked glycans having a variant glycosylation pattern characterized by a change in the level of one or more sugar moieties selected from the group consisting of glucose, galactose, mannose, and glucosamine. In some embodiments, the variant glycosylation pattern is characterized by a reduction in the level of galactose. In some embodiments, the variant glycosylation pattern is characterized by a reduction in the level of D-glucosamine. In some embodiments, the variant glycosylation pattern is characterized by an increase in the level of mannose. In some embodiments, the variant glycosylation pattern is characterized by an increase in the level of glucose. In some embodiments, the modified host cell produces antibodies that exhibit ADCC activity higher than that of a corresponding unmodified host cell. In some embodiments, the modified host cell produces antibodies having an increased binding affinity to FcγRIIIA receptor as compared to a corresponding antibody produced by a corresponding unmodified host cell. In some embodiments, the modified host cell is a Chinese Hamster Ovarian (CHO) cell. In some embodiments, the modified host cell is selected from the group consisting of NS0, SP2/0, HEK293, PER.C6 and YB2/0 cell. In some embodiments, the modified host cell is a myeloma cell. In some embodiments, the modified host cell maintains the variant glycosylation pattern after at least approximately 60 passages. In some embodiments, the modified host cell grows in a serum-free medium. In some embodiments, the modified host cell grows in suspension. In some embodiments, the modified host cell comprises a heterologous sequence encoding a heterologous glycoprotein.

In yet another aspect, the present invention provides an isolated host cell that produces glycoproteins exhibiting a substantially homogeneous pattern of N-linked glycan. In some embodiments, the substantially homogeneous pattern of N-linked glycan is evidenced by a single peak resolved by mass spectrometry. In some embodiments, the N-linked pattern has a structure of Formula I or II, in which a fucose moiety can optionally be linked to the first 4GlcNAc from the right:

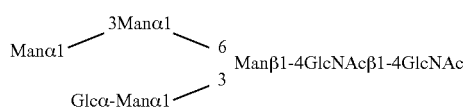

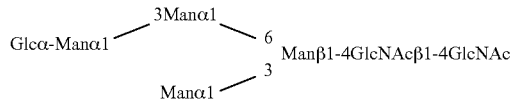

In yet another aspect, the modified host cell may comprise a heterologous sequence, wherein the heterologous sequence may encode a heterologous glycoprotein, such as an antibody or an enzyme. As disclosed herein, a method of producing a modified glycoprotein comprising: providing a heterologous polynucleotide sequence that encodes the modified glycoprotein; and causing the modified glycoprotein to be expressed in a modified host cell is also provided. Thus, also provided herein is a glycoprotein, such as a heterologous glycoprotein encoded by a heterologous sequence, that exhibits a variant glycosylation pattern characterized by a change in levels of at least two types of sugar molecules as compared to a corresponding wildtype glycoprotein, such as produced by an unmodified parental host cell. The variant glycosylation pattern can be evidenced by a change in level of N-linked oligosaccharides. The heterologous glycoprotein may exhibit a reduced or increased level of glucose, galactose, fucose, mannose, and/or of N-acetylglucosamine content as compared to a corresponding wildtype glycoprotein produced by an unmodified parental host cell. The N-acetylglucosamine may be α- or β-linked N-acetylglucosamine.

In one aspect, the glycoprotein is an antibody or antibody fragment. The antibody may bind a cancer antigen. For example, the antigen may be selected from the group consisting of HER2, CD20, EGF receptor, VEGF receptor, PDGF receptor, EpCam, CD3, CD4, CD19, CD30, CD33, CD40, CD51, CD55, CD80, CD95, CCR2, CCR3, CCR4, CCR5, folate receptor, CXCR4, insulin-like growth factor receptor, and integrin family members. The antibody may also exhibit increased antibody-dependent cellular cytotoxicity (ADCC) as compared to a corresponding antibody produced by an unmodified host cell. Furthermore, the antibody may include an IgG antibody. As disclosed herein, the antibody may also exhibit a variant glycosylation pattern characterized by a change in levels of at least two types of sugar molecules as compared to a corresponding wildtype antibody, such as produced by an unmodified parental host cell. The sugar molecules may be attached through an Fc region of the antibody.

In another aspect, the present invention provides an N-linked glycan comprising one glucose molecule, four mannose molecules, and two N-acetylglycosamine molecules. In some embodiments, the N-linked glycan comprises one or more fucose molecules. In some embodiments, the N-linked glycan has a structure of formula (I), in which a fucose moiety can optionally be linked to the first 4GlcNAc from the right.

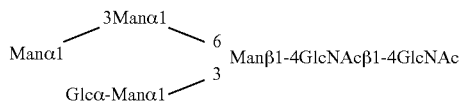

In some embodiments, the N-linked glycan has a structure of formula (II), in which a fucose moiety can optionally be linked to the first 4GlcNAc from the right.

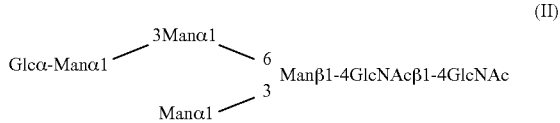

(II)

In another aspect, the present invention provides an isolated glycoprotein that contains an N-glycan disclosed herein. In some embodiments, the glycoprotein is an antibody. In some embodiments, the glycoprotein is an enzyme. In some embodiments, the N-linked glycan is attached to an Fc region of the antibody. In some embodiments, the antibody binds to a cancer antigen. In some embodiments, the cancer antigen is selected from the group consisting of HER2, Immunoglobulin epsilon Fc receptor II, Alk-1, CD20, EGF receptor, VEGF receptor, FGF receptor, NGF receptor, PDGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha and beta Integrins. In some embodiments, the antibody is produced by a modified host cell which produces a substantially homogeneous population of N-linked glycans. In some embodiments, the antibody has an increased ADCC (antibody-dependent cellular cytotoxicity) activity as compared to a corresponding antibody produced by an unmodified CHO cell clone, CHO-K1 (ATCC #CCL-61 and CRL-9618) or CHO-DG44 (Invitrogen #12609-012). In some embodiments, the antibody has an increased binding affinity to FcγRIIIA receptor as compared to a corresponding antibody produced by an unmodified CHO cell clone, CHO-K1 (ATCC #CCL-61 and CRL-9618) or CHO-DG44 (Invitrogen #12609-012). In some embodiments, the antibody is an inhibitory antibody. In some embodiments, the antibody is a stimulatory antibody. In some embodiments, the antibody is an IgG antibody.

In some embodiments, the host cell that produces glycoproteins exhibiting a substantially homogeneous pattern of N-linked glycan is a non-lymphocytic cell. In some embodiments, the host cell is a CHO cell. In some embodiments, the host cell produces antibodies exhibiting a substantially homogeneous pattern of N-linked glycan.

In still another aspect, the present invention provides a method of producing a modified glycoprotein comprising: (a) providing a heterologous polynucleotide sequence that encodes the modified glycoprotein; and (b) causing the modified glycoprotein to be expressed in a host cell disclosed herein. In some embodiments, the modified glycoprotein is secreted by the host cell. In some embodiments, the host cell is maintained in a serum free medium. In some embodiments, the host cell is maintained in a suspension culture. In some embodiments, the modified glycoprotein is an antibody.

Also provided in the present invention is a culture medium comprising a host cell as disclosed herein. In some embodiments, the culture medium is serum free. The present invention also discloses a culture fermentor comprising a plurality of host cells that produce N-glycan having a variant glycosylation pattern or glycoprotein exhibiting a substantially homogeneous pattern of N-glycan in a culture medium.

In another aspect, the present invention provides an antibody produced by a modified host cell, the antibody comprising an N-linked glycan, wherein the antibody has increased binding affinity to an Fc gamma receptor IIIa (FcγRIIIa), and/or decreased binding affinity to an Fc gamma receptor IIb (FcγRIIb), as compared to a corresponding antibody produced by an unmodified host cell, thereby enhancing ADCC (antibody-dependent cell-mediated cytotoxicity) activity against effector cells expressing FcγRIIIa and/or FcγRIIb. In another aspect, the present invention provides an antibody produced by a modified host cell, the antibody comprising an N-linked glycan, wherein the antibody exhibits an increased ADCC activity, as compared to a corresponding antibody produced by a corresponding unmodified host cell, and wherein the increased ADCC activity is against effector cells expressing a high affinity Fc gamma receptor, FcγRIIIa 158V/V, and effector cells expressing a low affinity Fc gamma receptor, FcγRIIIa 158F/F or FcγRIIIa 158F/V.

In some embodiments of the antibody of the present invention, the N-linked glycan comprises one glucose molecule, four mannose molecules, and two N-acetylglycosamine molecules. In some embodiments, the N-linked glycan comprises one or more fucose molecules. In some embodiments, the N-linked glycan having a structure of formula (I) or (II), in which a fucose moiety can optionally be linked to the first 4GlcNAc from the right.

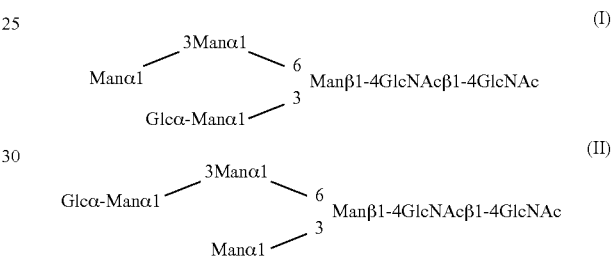

In some embodiments, the N-linked glycan is attached to an Fc region of the antibody. In some embodiments, the antibody binds to a cancer antigen. The cancer antigen can include but are not limited to HER2, Immunoglobulin epsilon Fc receptor II, Alk-1, CD20, EGF receptor, VEGF receptor, FGF receptor, NGF receptor, PDGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha and beta Integrins. The antibody of the present invention can be an inhibitory antibody or a stimulatory antibody. In some embodiments, the antibody is an IgG antibody. In some embodiments, the antibody has an increased ADCC (antibody-dependent cell-mediated cytotoxicity) activity against effector cells expressing a low affinity FcR, FcγRIIIa 158F/F or FcγRIIIa 158 F/V, as compared to a corresponding antibody produced by an unmodified CHO cell clone, CHO-K1 (ATCC #CCL-61 and CRL-9618) or CHO-DG44 (Invitrogen #12609-012). In some embodiments, the antibody has an increased ADCC (antibody-dependent cell-mediated cytotoxicity) activity against effector cells expressing a high affinity FcR, FcγRIIIa 158V/V, as compared to a corresponding antibody produced by an unmodified CHO cell clone, CHO-K1 (ATCC #CCL-61 and CRL-9618) or CHO-DG44 (Invitrogen #12609-012). In some embodiments, the host cell is a Chinese Hamster Ovarian (CHO) cell. The host cell can include but are not limited to NS0, SP2/0, HEK293, PER.C6 and YB2/0 cell. The host cell can also be a myeloma cell. In some embodiments, the effector cell is a human peripheral blood mononuclear cell (PBMC). In some embodiments, the effector cell is an NK cell, a monocyte, a macrophage, or a polymorphonuclear neutraphils (PMN).

In another aspect, the present invention provides a modified host cell characterized in its ability to produce a modified antibody having an N-linked glycan, wherein the antibody exhibiting an increased binding affinity to an Fc gamma receptor IIIa (FcγRIIIa), and/or decreased binding affinity to an Fc gamma receptor IIb (FcγRIIb), as compared to a corresponding antibody produced by an unmodified host cell, thereby enhancing ADCC (antibody-dependent cell-mediated cytotoxicity) activity against effector cells expressing FcγRIIIa and/or FcγRIIb. In yet another aspect, the present invention provides a modified host cell characterized in its ability to produce a modified antibody having an N-linked glycan, wherein the antibody exhibits an increased ADCC activity, as compared to a corresponding antibody produced by a corresponding unmodified host cell, and wherein the increased ADCC activity is against effector cells expressing a high affinity Fc gamma receptor, FcγRIIIa 158V/V, and effector cells expressing a low affinity Fc gamma receptor, FcγRIIIa 158F/F or FcγRIIIa 158F/V.

In some embodiments of the modified host cells of the present invention, the N-linked glycan exhibits a variant glycosylation pattern characterized by a change in the level of one or more sugar moieties selected from the group consisting of glucose, galactose, mannose, and glucosamine. In some embodiments, the variant glycosylation pattern is characterized by a reduction in the level of galactose. In some embodiments, the variant glycosylation pattern is characterized by a reduction in the level of D-glucosamine. In some embodiments, the variant glycosylation pattern is characterized by an increase in the level of mannose. In some embodiments, the variant glycosylation pattern is characterized by an increase in the level of glucose. In some embodiments, the N-linked glycan has a structure of Formula I or II, in which a fucose moiety can optionally be linked to the first 4GlcNAc from the right:

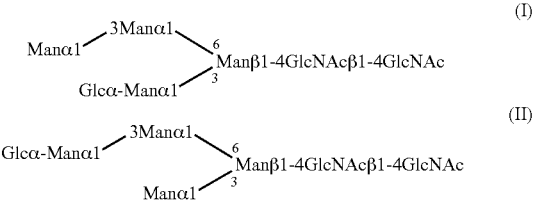

In some embodiments, the host cell produces antibodies that exhibit an increased ADCC activity against effector cells expressing a high affinity Fc receptor, FcγRIIIa 158V/V, and an increased ADCC activity against cells expressing a low affinity Fc receptor, FcγRIIIa 158F/F or FcγRIIIa 158F/V, as compared to a corresponding antibody produced by a corresponding unmodified host cell. In some embodiments, the host cell produces antibodies that exhibit an increased binding affinity to an Fc gamma receptor IIIa (FcγRIIIa), and/or decreased binding affinity to an Fc gamma receptor IIb (FcγRIIb), as compared to a corresponding antibody produced by an unmodified host cell, thereby enhancing ADCC activity against effector cells expressing FcγRIIIa and/or FcγRIIb. In some embodiments, the antibody binds to a cancer antigen. The cancer antigen can include but are not limited to HER2, Immunoglobulin epsilon Fc receptor II, Alk-1, CD20, EGF receptor, VEGF receptor, FGF receptor, NGF receptor, PDGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha and beta Integrins. In some embodiments, the host cell is a Chinese Hamster Ovarian (CHO) cell. The host cell can include but are not limited to NS0, SP2/0, HEK293, PER.C6 and YB2/0 cell. The host cell can also be a myeloma cell. In some embodiments, the cell maintains the variant glycosylation pattern after at least approximately 60 passages. In some embodiments, the modified host cell grows in a serum-free medium. In some embodiments, the modified host cell grows in suspension. In some embodiments, the modified host cell comprises a heterologuous sequence encoding a heterologous glycoprotein.

Also provided by the present invention is a method of preventing or treating a disorder, the method comprising administering to a subject in need thereof an effective amount of a subject antibody disclosed herein. In some embodiments, the disorder is selected from the group consisting of cancer, allergies, cardiovascular diseases, inflammatory diseases, metabolic diseases, neurological diseases, viral infections and/or bacterial infections. For example, the disorder can be a cancer or an allergy. In some embodiments, the subject is a mammal, for example, a human. In some embodiments, the administration of the subject antibody is via parenteral injection, infusion, oral administration or inhalation. The present invention also provides a method of producing a modified antibody comprising: (a) providing a heterologous polynucleotide sequence that encodes the modified antibody; and (b) causing the modified antibody to be expressed in a subject host cell disclosed herein. In some embodiments, the modified antibody is secreted by the host cell. In some embodiments, the host cell is maintained in a serum free medium. In some embodiments, the host cell is maintained in a suspension culture. The present invention also encompasses a culture medium comprising a subject host cell and a culture fermentor comprising a plurality of the subject host cells in a culture medium. In some embodiments, the culture medium is serum free.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

LCA binding to the surface of cells with high fucose will bring the saporin within close proximity of the cell membrane, which results in cell killing.

Figure 2:
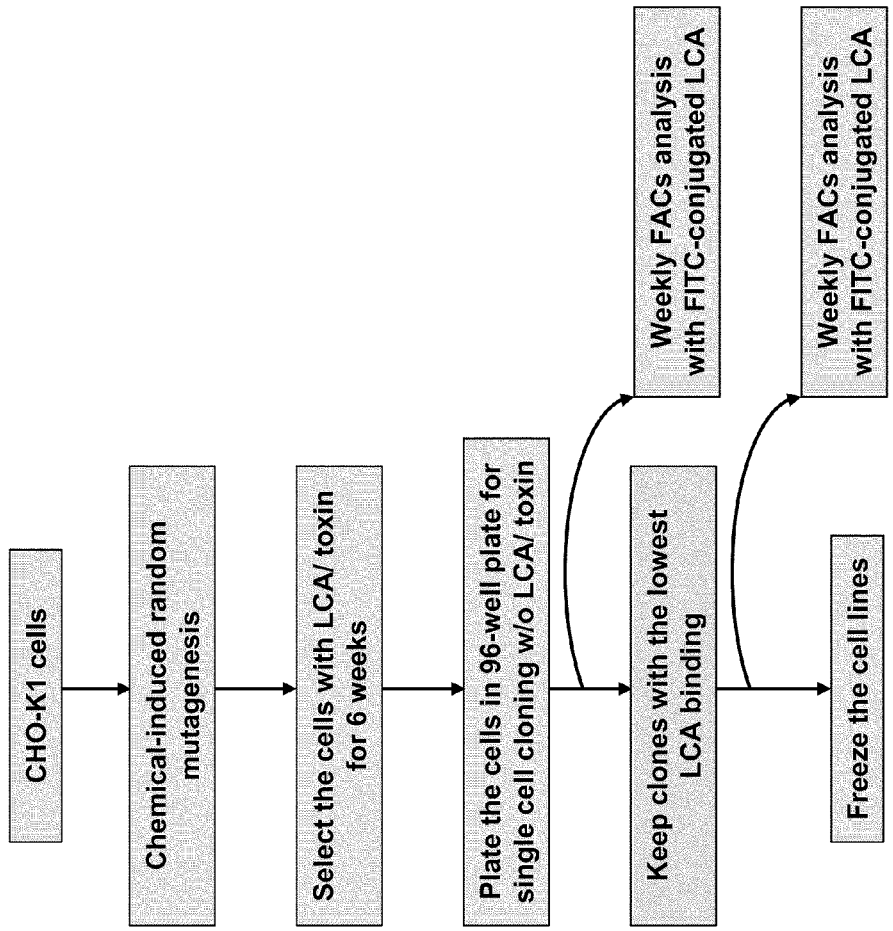

FIG. 2 is a flow chart of selecting low-fucose CHO-K1 mutant cells after chemical-induced random mutagenesis.

Figure 3:
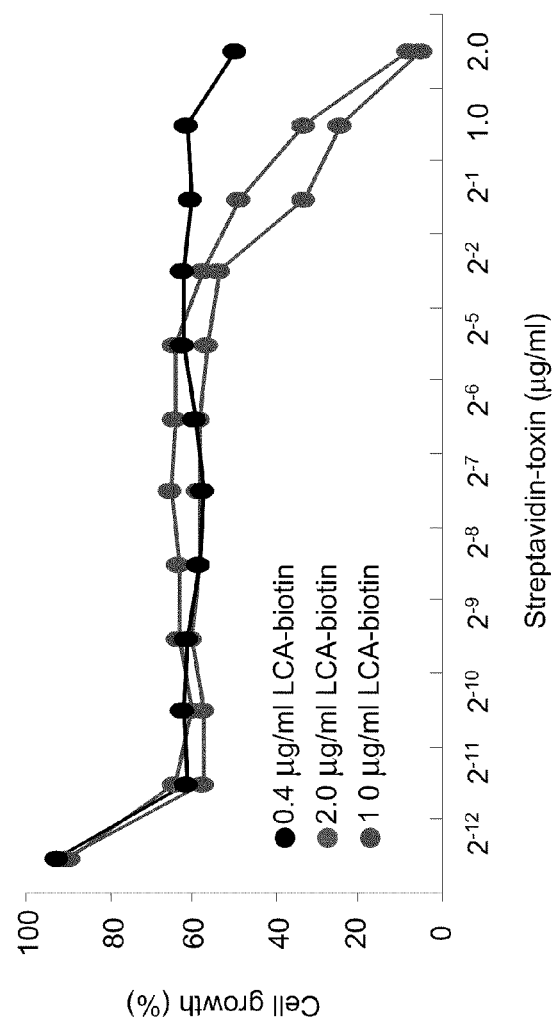

FIG. 3 is a graph illustrating determination of the optimal concentrations of LCA-biotin and streptavidin-toxin to kill CHO-K1 cells with high fucose. $10^5$ CHO-K1 cells per well were plated into 96-well plates. LCA-biotin and stretavidin-saporin were mixed in the medium at different concentration as indicated and added to the cells. Cell growth was measured by MTT assay 10 days later. The cell grown in the medium without the toxin was used as the control.

Figure 4B:
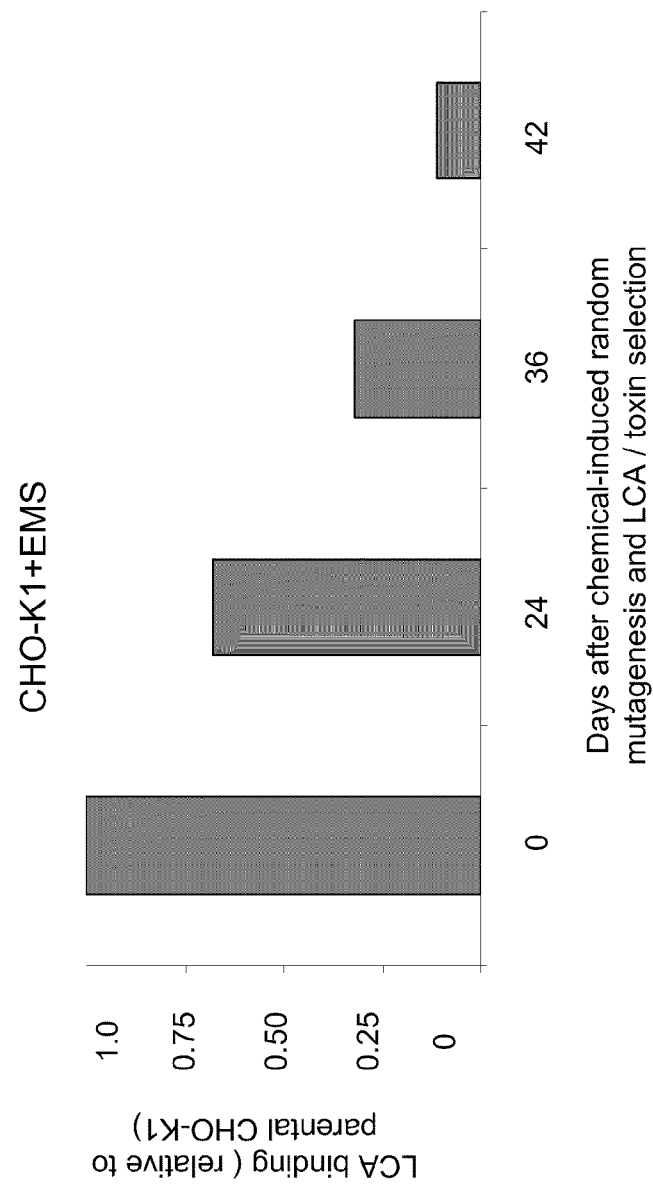

FIG. 4 shows LCA/toxin selection gradually enriches the cell population with low fucose after chemical-induced random mutagenesis. A) Random mutation(s) were induced by ICR-191 in CHO-K1 cells and the cells were treated with LCA-biotin and stretavidin-saporin for 70 days. The cellular fucosylation status was examined by FITC-conjugated LCA labeling and FACs analysis every week. Parental CHO-K1 cells were used as positive control. B) Ethyl Methane Sulfonate (EMS) was used to induce random mutagenesis in CHO-K1 cells. The selection and fucosylation monitoring were as described in A).

FIG. 5 shows graphs illustrating that low fucose content in LCA/toxin-resistant cells is genetically stable. One of the clones with low fucosylation was grown and expanded in LCA-biotin and stretavidin-saporin-free medium for three months. The cellular fucosylation status was examined by FITC-conjugated LCA labeling and FACS analysis weekly.

Figure 6:
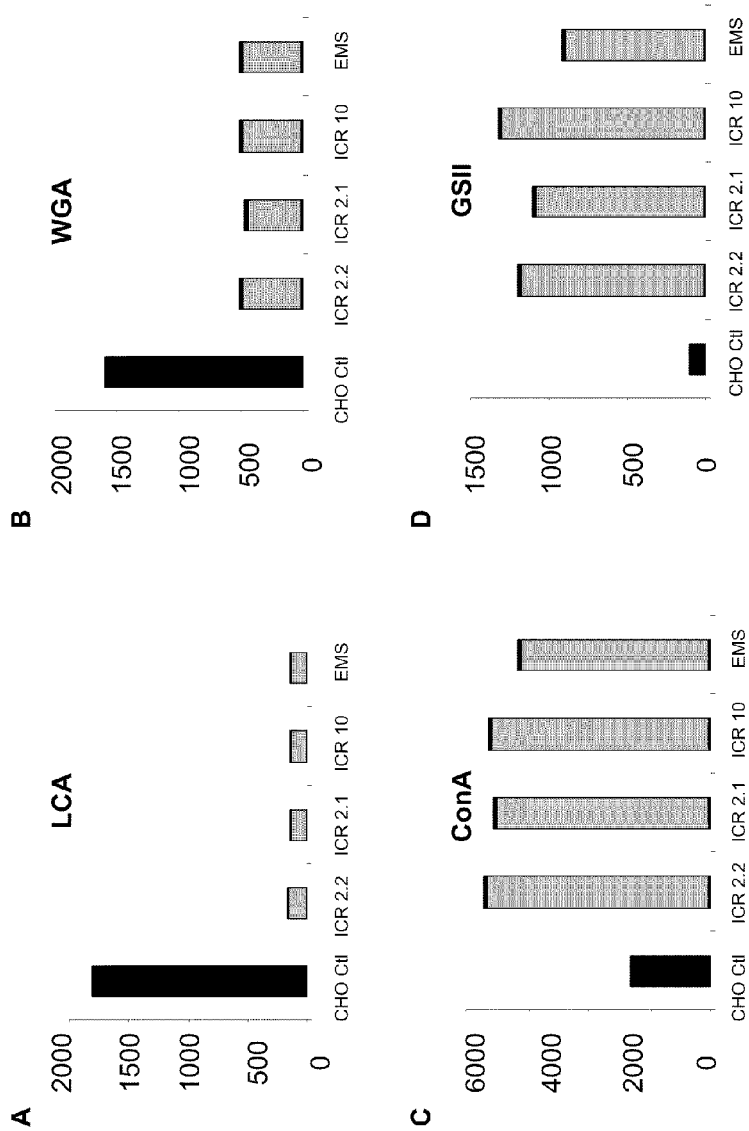

FIG. 6 depicts the N-glycan profile of low LCA-binding mutant CHO-K1 cells. The stable cell populations after LCA-biotin and stretavidin-saporin selection were labeled with FITC-conjugated lectins (LCA, WGA, ConA and GS-II) and analyzed by FACS.

Figure 7:
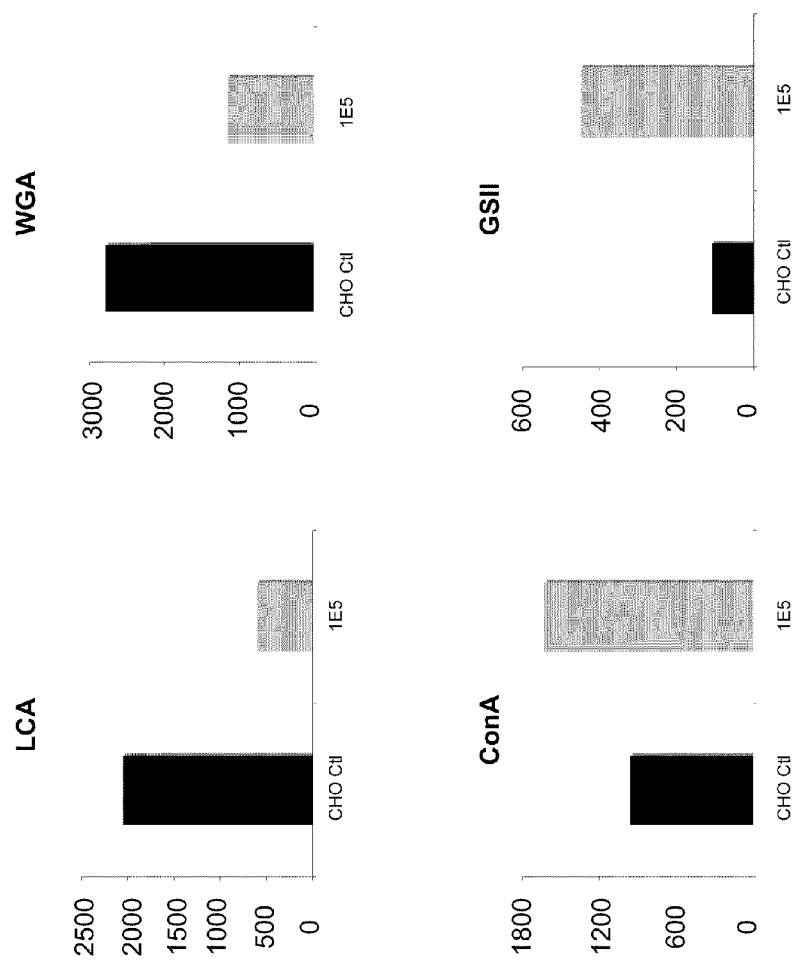

FIG. 7 depicts the N-glycan profile of one of the mutant CHO-K1 clones adapted to serum-free culture medium in suspension. The mutant clones were isolated by single cell cloning by limiting dilution. The clones were adapted to serum-free suspension and the mutant clone was labeled with FITC-conjugated lectins (LCA, WGA, ConA and GS-II) and analyzed by FACS. The profile of one of the clones is shown.

Figure 8:
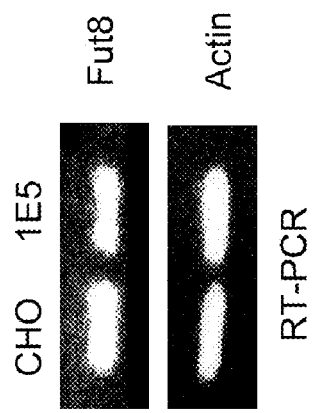

FIG. 8 illustrates the expression of Fut8 is not altered in a mutant CHO-K1 clone.

Figure 9:
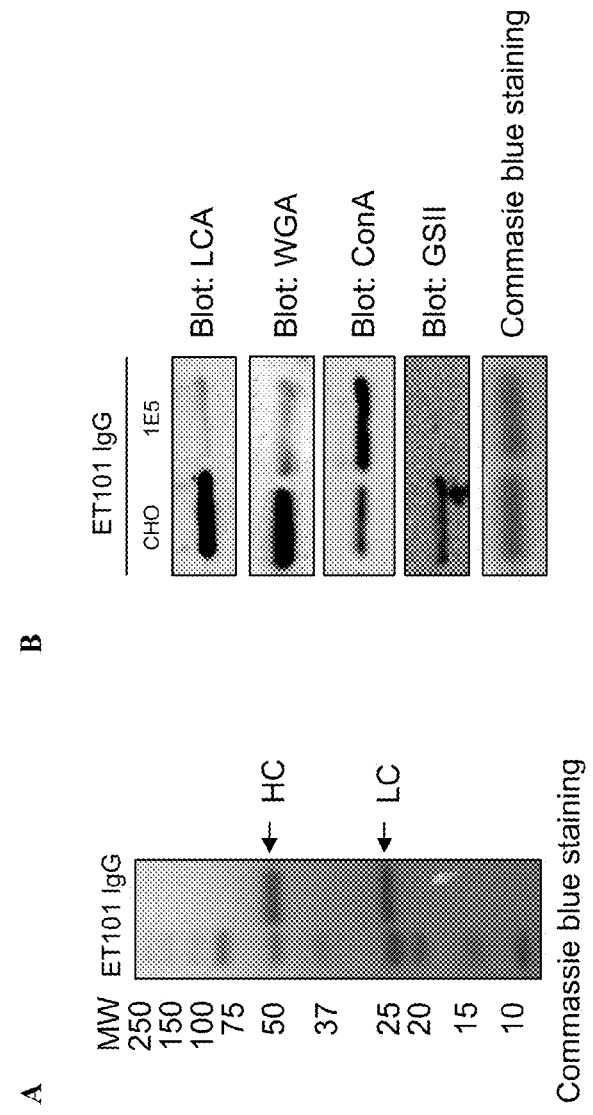

FIG. 9 depicts a unique N-glycan profile of an antibody produced by a mutant clone grown in serum-free medium in suspension. The expressed antibody ET101 was separated by SDS-PAGE gel, stained with A) Coomassie Blue, or B) transferred to nitrocellulose membrane and blotted with LCA, WGA, ConA and GS-II conjugated with biotin followed by incubation with HRP-conjugated Streptavidin.

FIG. 10 depicts a unique profile of monosaccharide composition in the antibodies produced by the mutant clones adapted to grow in serum-free medium in suspension. A) Quantification of monosaccharides in antibody ET101 produced by parental CHO cells, mutant CHO-1E5 clone, mutant CHO-3F clone, or mutant CHO-2.6 clone. All the CHO clones were adapted to serum-free medium cultured in suspension. B) Monosaccharide composition of human IgG1 (ET101 and ET201) produced by parental CHO cells, mutant CHO-1E5 clone, mutant CHO-3F clone, or mutant CHO-2.6 clone. C) Monosaccharide composition analysis of human IgG1 produced by Fut8−/− knockout CHO cells, from Yamane-Ohnuki et al, *Biotechnol. Biogeng.* 87:614-622 (2004).

Figure 11:
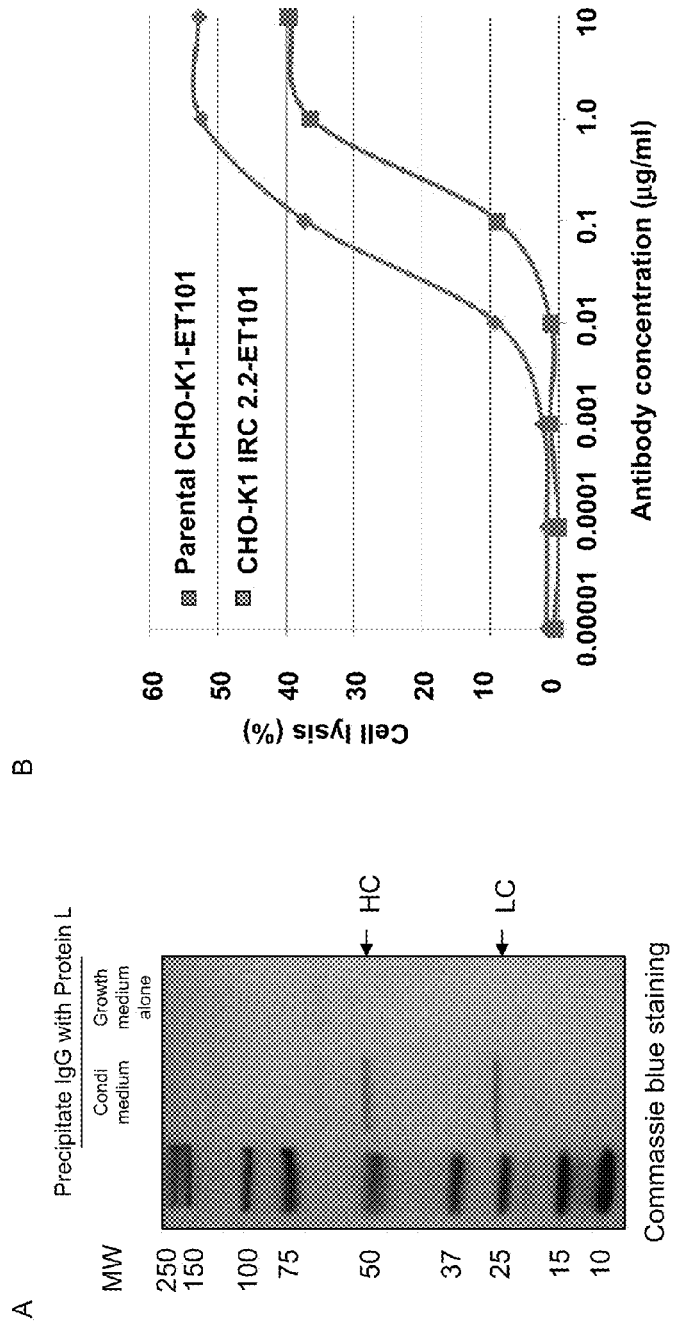

FIG. 11 depicts enhanced ADCC activity shown by ErbB2-blocking human IgG1 (ET101) produced by the mutant cell population grown in serum-containing culture medium. A) Expressed antibody ET101 from 1 milliliter of conditioned media containing 10% FBS was precipitated by protein L beads, separated by a reducing SDS-PAGE gel and stained with Coomassie blue. The blank growth medium was used as negative control. B) ET101 antibody expressed in mutant clone (IRC 2.2) or wild type CHO (parental) in ADCC assay with SKBR3 cells.

Figure 12:
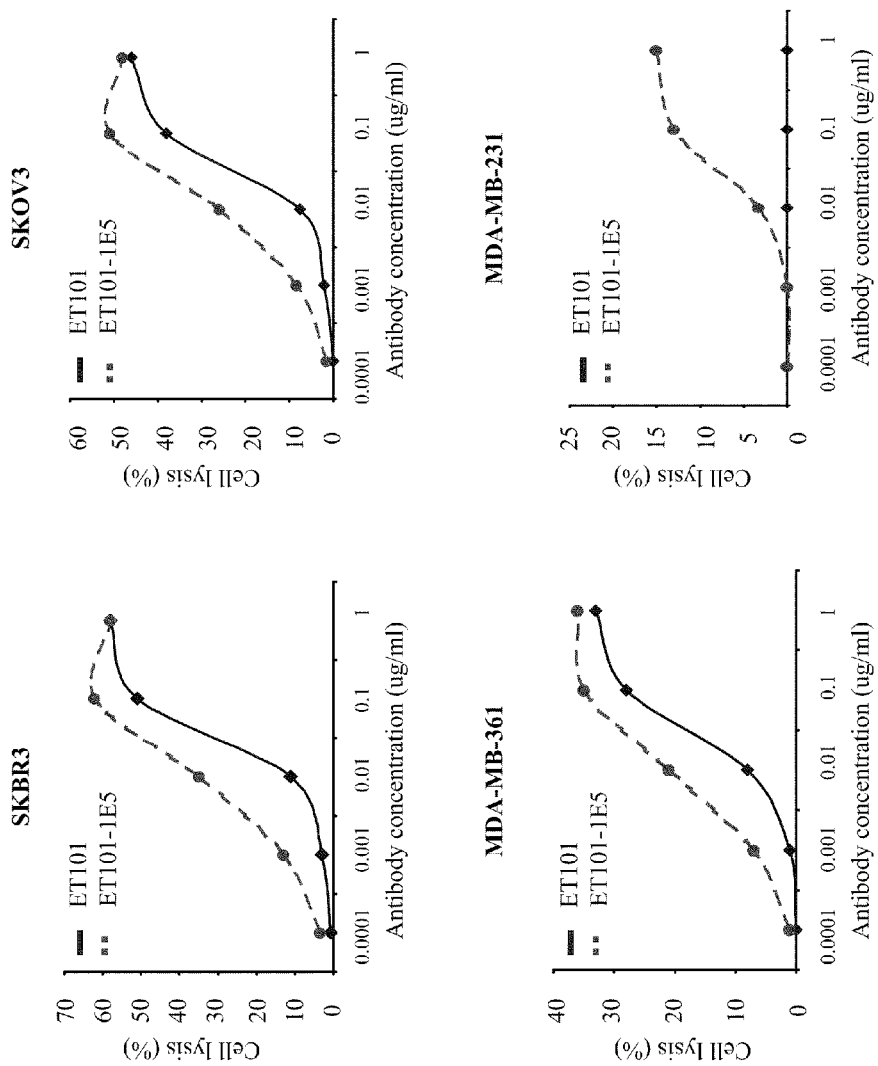

FIG. 12 depicts enhanced ADCC activity against multiple cancer cell lines (SKBR3, SKOV3, MDA-MB-361, and MDA-MB-231) by ErbB2-blocking antibody human IgG1 (ET101) produced by a mutant CHO-K1 cell clone, denoted by ET101-1E5, adapted to serum-free medium, as compared to ET101 produced by parental cell line, denoted ET101 on the graph.

Figure 13:
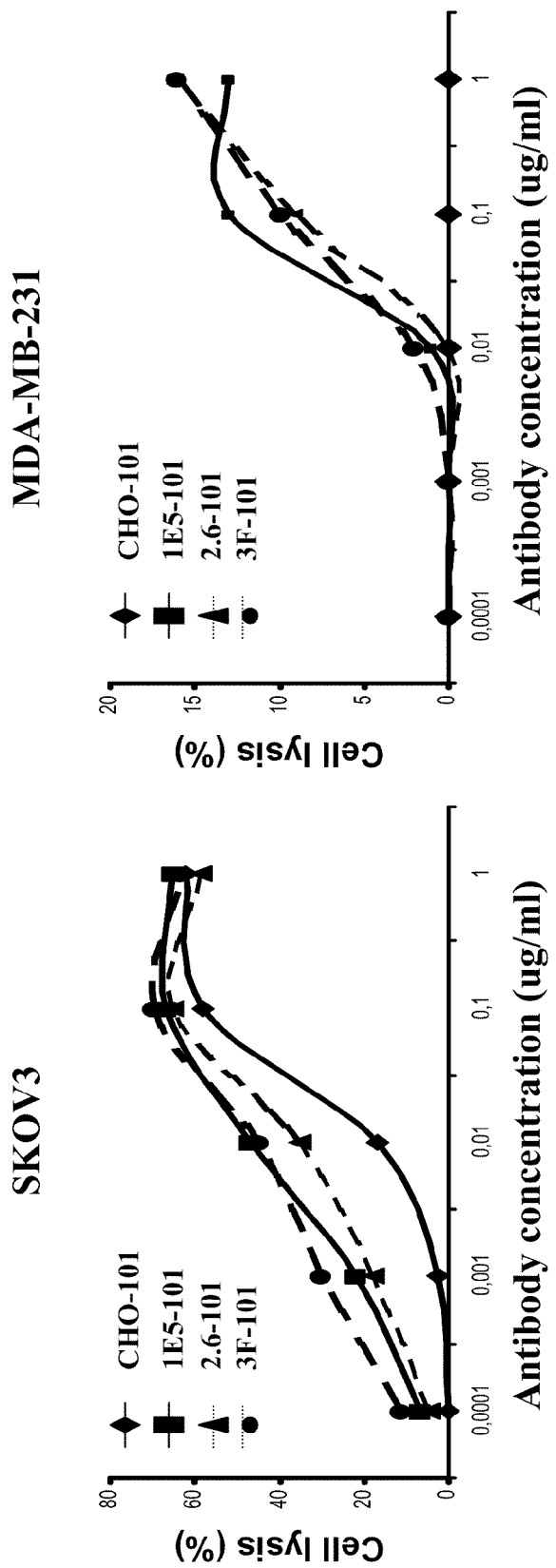

FIG. 13 depicts enhanced ADCC activity against cancer cell lines SKOV3 and MDA-MB-231 by ErbB2-blocking antibody human IgG1 (ET101) produced by multiple individual mutant CHO-K1 cell clones (1E5, 2.6, and 3F) adapted to serum-free medium, as compared to ET101 produced by the wild type CHO line (CHO). PBS or nonspecific antibody was used as negative control.

Figure 14:
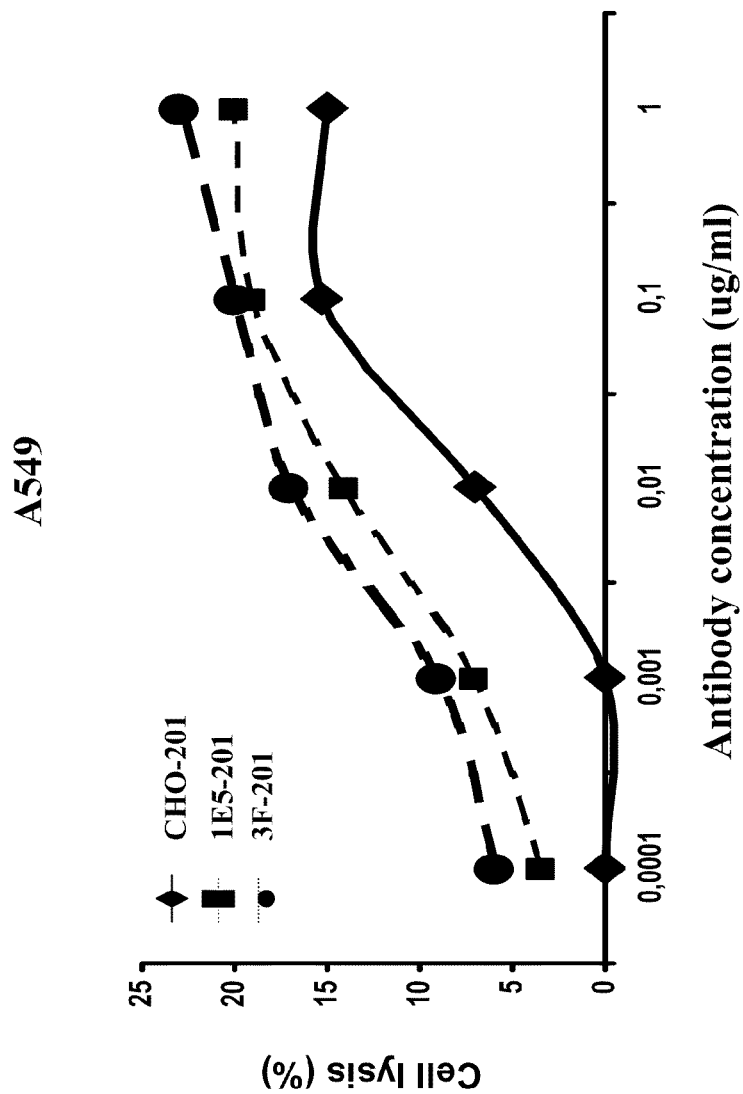

FIG. 14 depicts enhanced ADCC activity cancer cell line A549 by another blocking antibody human IgG1 (ET201) targeting EGFR. Depicted are ET201 produced by 2 individual mutant CHO-K1 cell clones (1E5 and 3F) adapted to serum-free medium, as compared to ET201 produced by wild type CHO line (CHO). PBS or nonspecific antibody was used as negative control.

FIG. 15a and b represent a schematic showing of the composition and structure of N-linked oligosaccharide synthesized by a modified host cell of the present invention, designated as CHO-1E5. The structure shown here is determined by the analysis of monosaccharide profile, MALDI-TOF MS spectra of the glycan, and mannosidase digestion of the antibody produced by CHO-1E5 cells.

Figure 16:
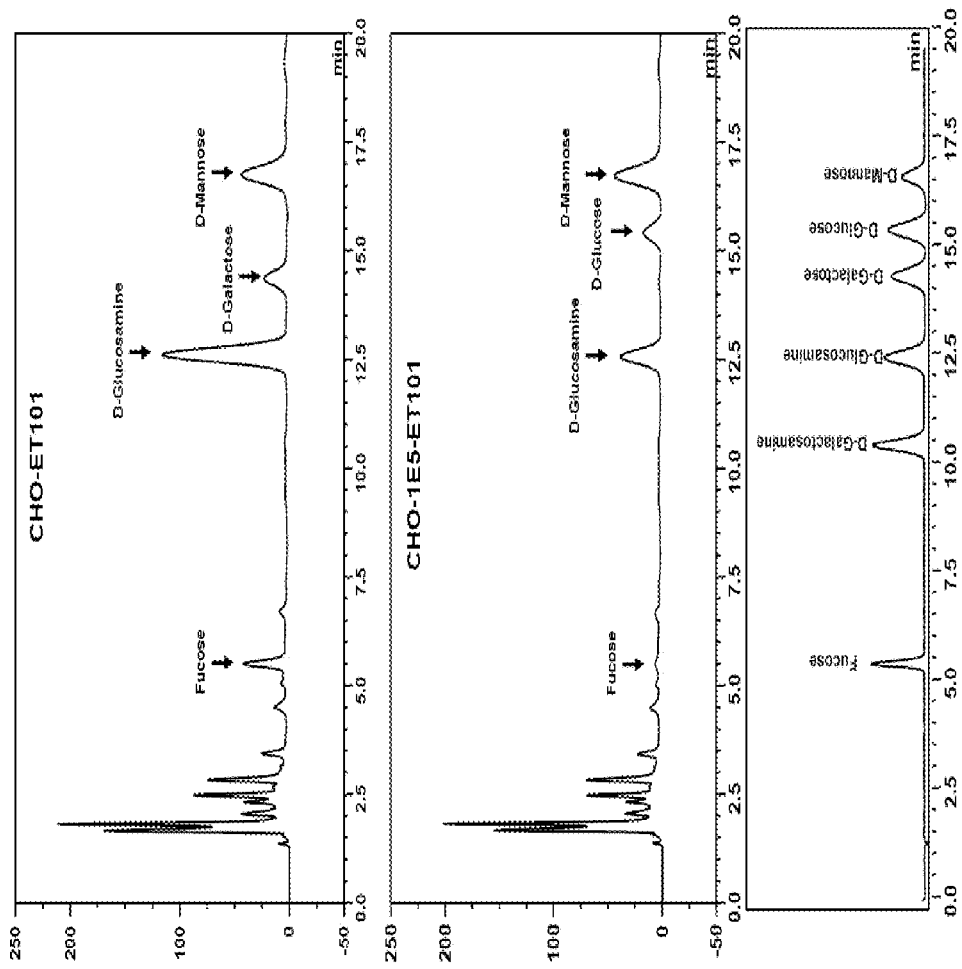

FIG. 16 shows the profiles of monosaccharides in the antibody produced by wild type CHO parental host cells (top panel) and CHO-1E5 cells (middle panel) and the corresponding monosaccharide standard (bottom panel) in serum-free suspension.

Figure 17:
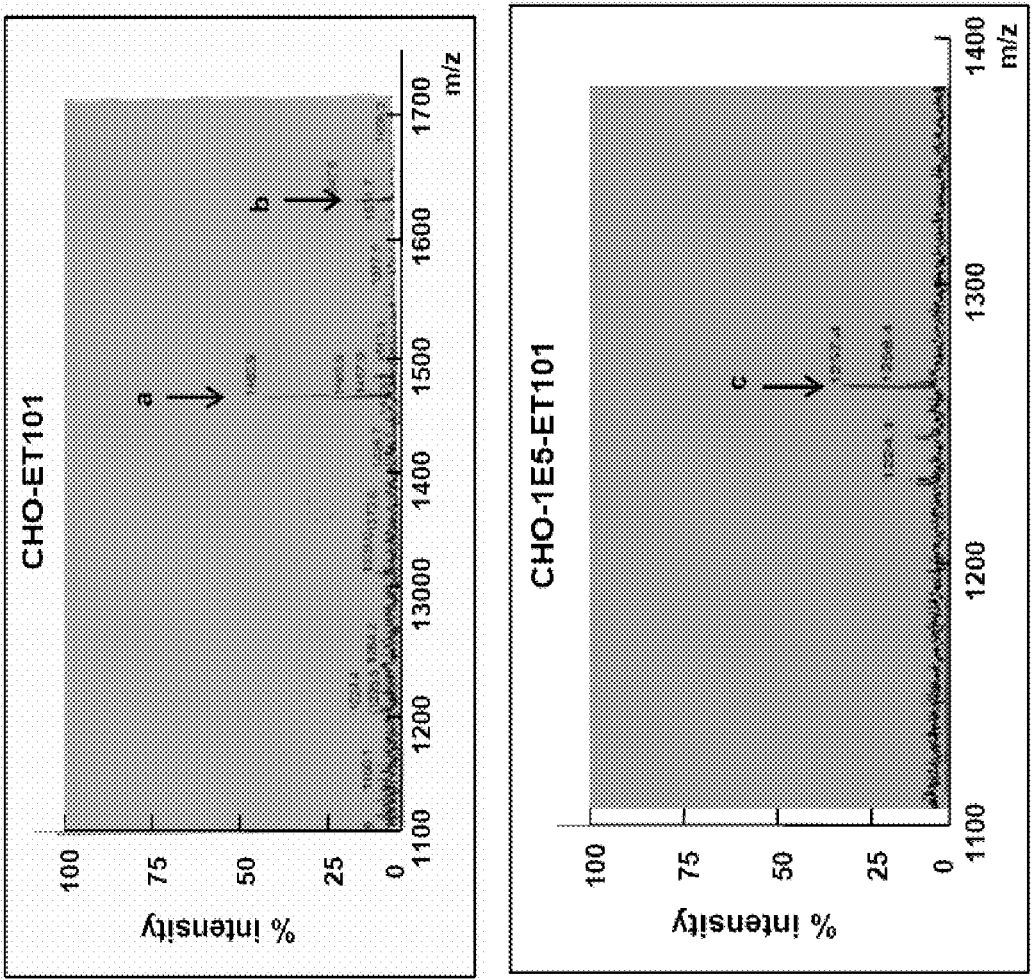

FIG. 17 shows the MALDI-TOF MS spectra of N-linked oligosaccharides from the antibody produced by the wild type parental CHO cells (top panel) and CHO-1E5 cells (bottom panel).

Figure 18:
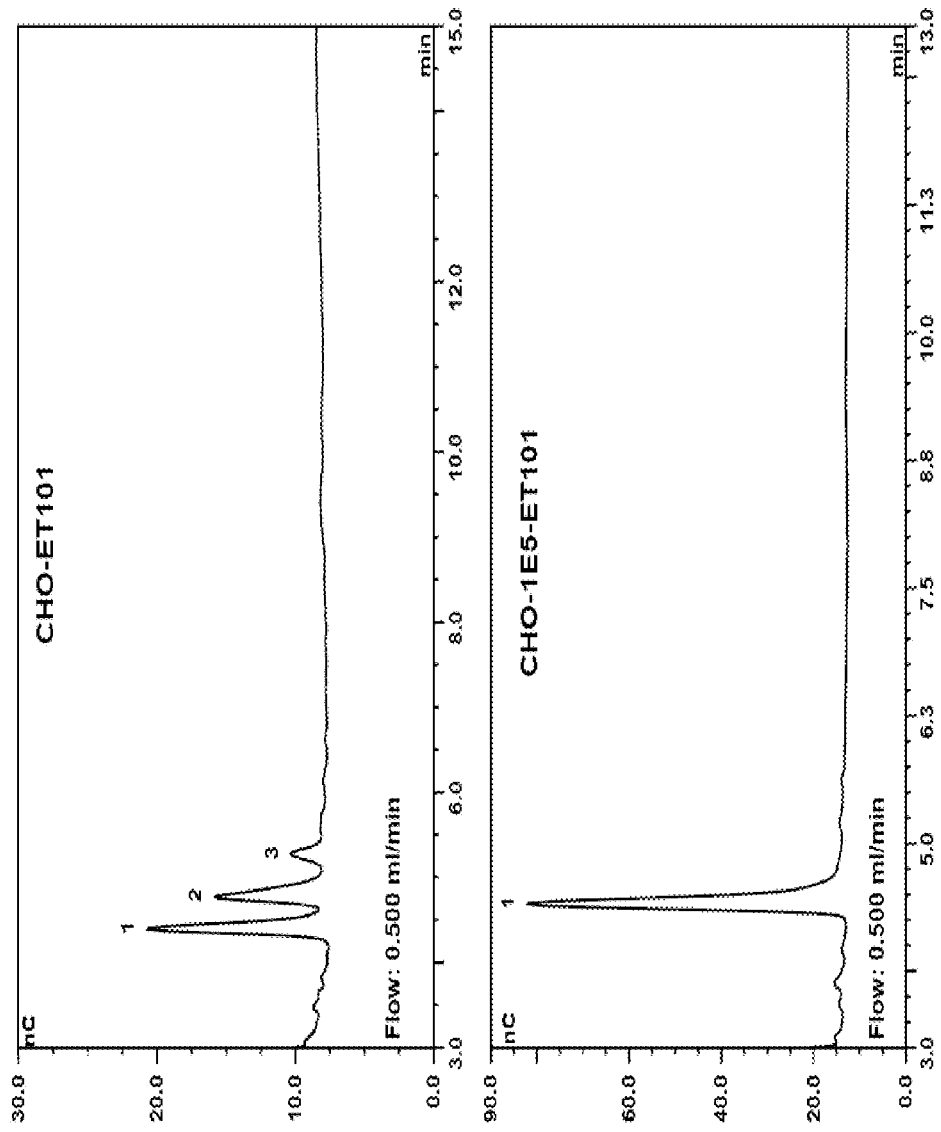

FIG. 18 shows the elution profile of N-linked glycan released from antibodies produced by the wild type parental CHO cells (top panel) and CHO-1E5 cells (bottom panel). The results show that the antibody produced by CHO-1E5 cells has a single population of N-linked oligosaccharide, as compared to the mixed population in antibody produced by the wild type CHO cells. N-glycan was released by digesting 200 μg of antibody with PNGase F for 72 hours at 37° C. The protein was precipitated by 70% ethanol at −20° C. overnight and removed by centrifugation. The supernatants were dried under vacuum and resuspended in 200 μl of deionized water. The samples were loaded onto the microcolumns packed with C18, AG50WX8 and AG4x4. The columns were then washed with 300 μl of deionozed water. The flowthrough was collected and the oligosaccharide was analyzed by PA200 column and Dionex ICS-3000.

Figure 19:
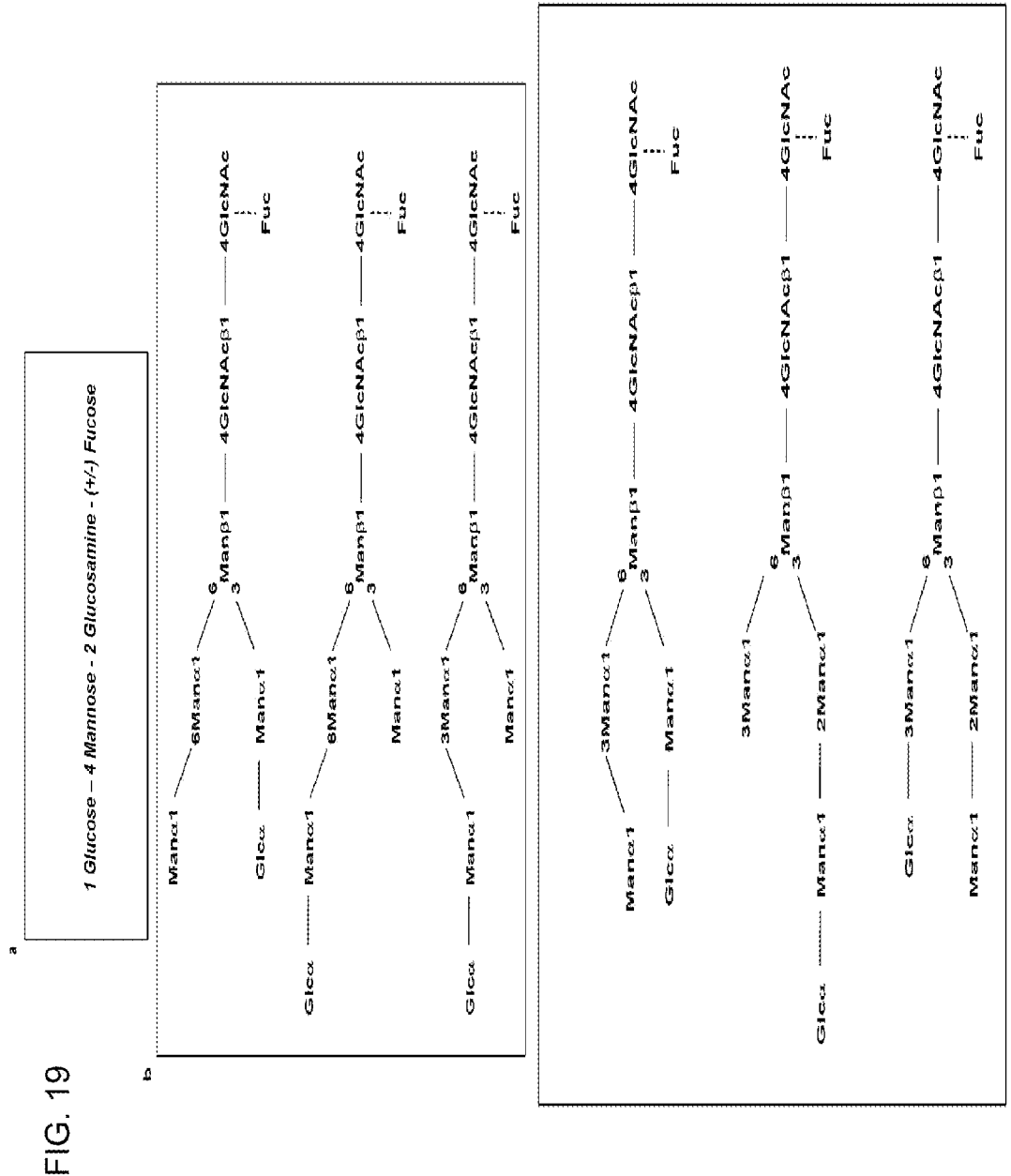

FIG. 19 shows the composition and putative structures of oligosaccharides produced by CHO-1E5. 19A. the monosaccharide composition of the N-glycan produced by CHO-1E5 was determined by PA1 column/Dionex ICS-3000 system and MALDI-TOF MS as described in FIGS. 16 and 17. 19B.

the putative structures of the N-glycan were deduced from the results of monosaccharide analysis and MALDI-TOF MS.

Figure 20:
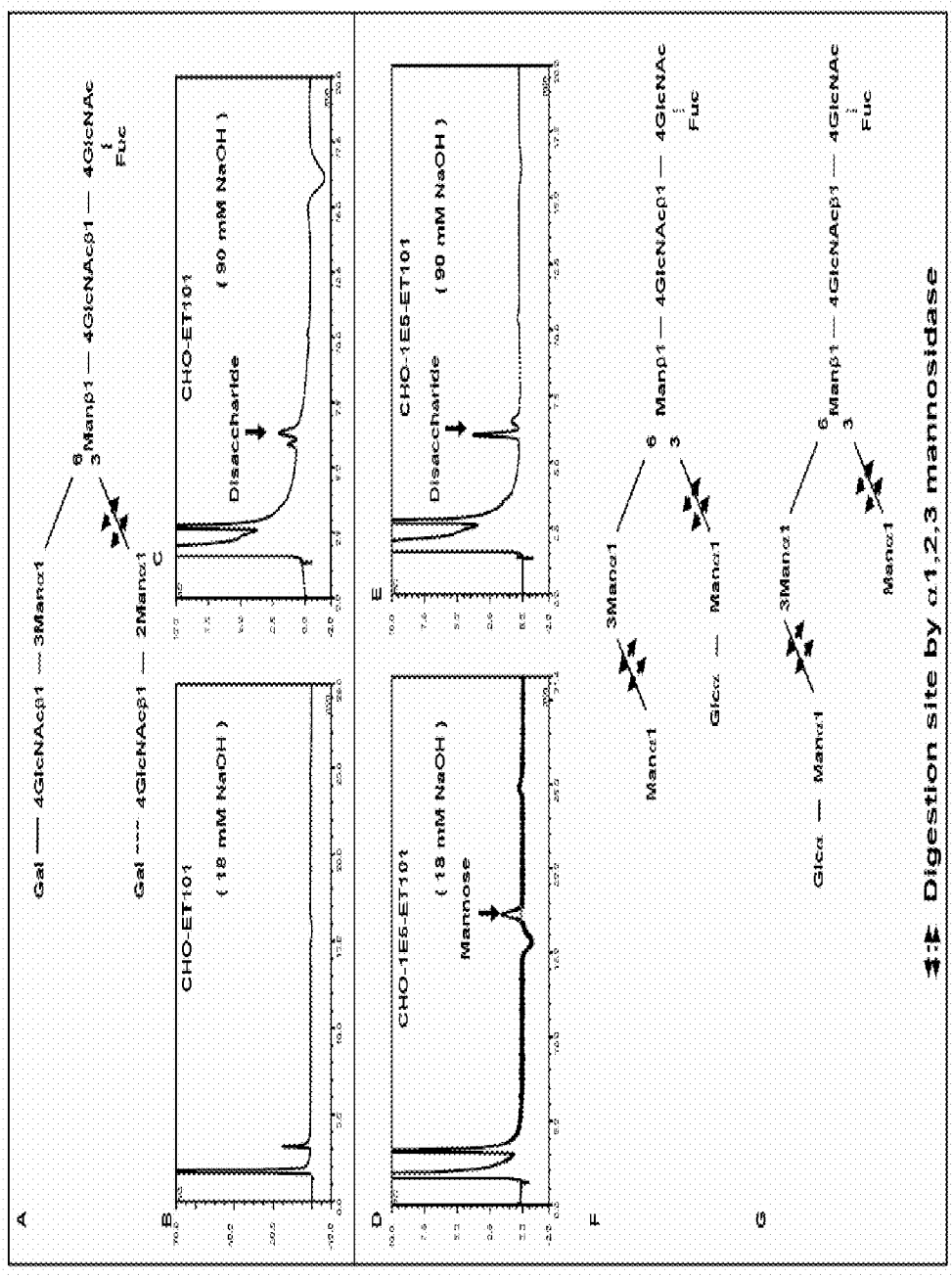

FIG. 20 shows the structural determination of the oligosaccharides produced by CHO-1E5 through the digestion of α1,2,3 mannosidase. The antibodies (ET101) synthesized by CHO-1E5 and parental host cells were incubated with α1,2,3 mannosidase at 37° C. for 24 hours. To remove the antibody and the enzyme, the digested antibody solution was first passed through MicroCon YM10 (Millipore, Billerica, Mass.) and then MicroCon YM100 (Millipore, Billerica, Mass.). The sample was analyzed by PA1 column/Dionex ICS-3000 system. A. the α1,2,3 mannosidase digestion site of the N-glycan from the sample of parental host cells. Band C. the saccharide profile eluted by 18 mM NaOH (B) and by 90 mM NaOH (C) from the sample of the parental host cells. D and E. the saccharide profile eluted by 18 mM NaOH (D) and by 90 mM NaOH (E) from the sample of CHO-1E5. F and G. the structures of N-glycan synthesized by CHO-1E5 is deduced by the analysis.

Figure 21:
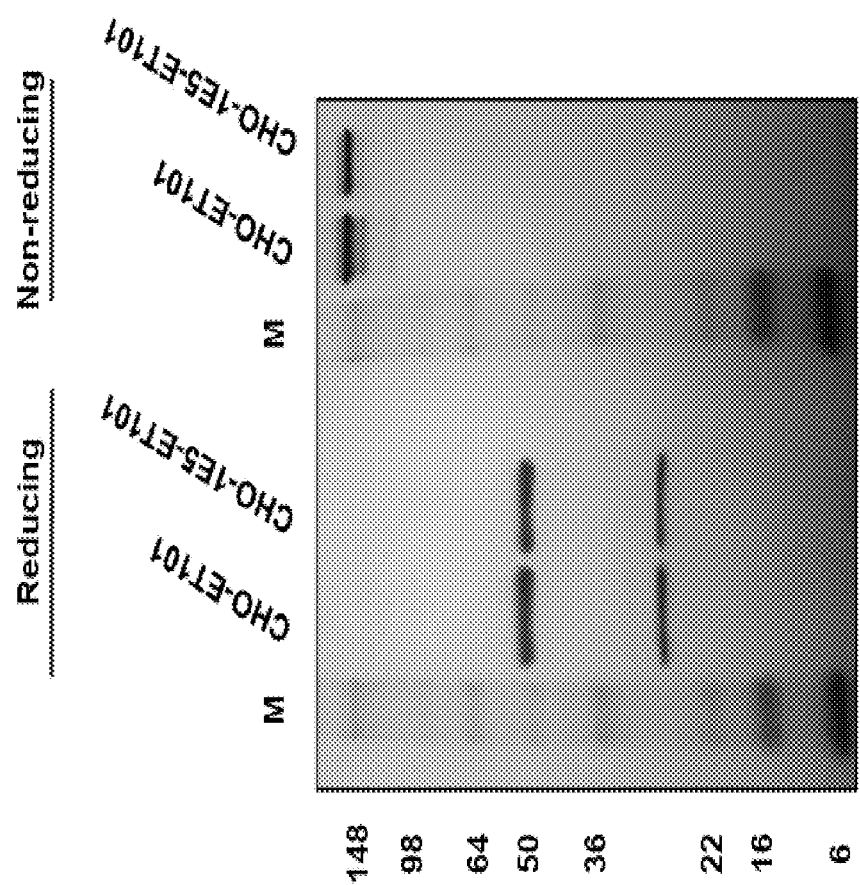

FIG. 21 is a reproduction of an electrophoresis gel showing the bands corresponding to an antibody heavy chain (approximately 50 KD) and a light chain (approximately 25 KD) produced by the wild type parental CHO cells and CHO-1E5 cells under a reducing condition, and the bands corresponding to an antibody (approximately 150 KD) produced by the wild type parental CHO cells and CHO-1E5 cells under a non-reducing condition. The results show that the oligosaccharide exhibiting the glycosylation pattern does not alter the protein structure and assembly of antibody produced by CHO-1E5 cells.

FIG. 22 shows the results of a cell lysis assay indicative of enhanced ADCC activity by the antibody exhibiting the glycosylation pattern produced by CHO-1E5 cells. 8A. Enhanced ADCC activity against multiple cancer cell lines (SKOV3 and MDA-MB-231) by ErbB2-blocking antibody human IgG1 (ET101) produced by CHO-1E5 cell clone adapted to serum-free medium. ET101 antibody expressed in CHO-1E5 cells was purified from the conditioned medium by Protein A chromatography; and quantified by UV280. Parental ET101 was expressed in the wild type CHO cells and purified in the same way. For ADCC assay, 100 μl of target cell suspension were pre-incubated with 50 μl of the expressed ErbB2-blocking antibody ET101 in 96-well plate at 37° C. for half hour. 50 μl of PBMCs were then added at the effector/target cell ratio of 20:1. After incubated for 16 hours, the plate was spun down and 50 μl of cell-free supernatants were transferred to a new plate. The released LDH was measured by CytoTox96 Non-radioactive Cytotoxicity Assay (Promega, Madison, Wis.). The cell lysis was calculated by the formula (E−S)/(M−S) (E: experimental release, S: spontaneous release, M: maximal release). PBS or nonspecific antibody was used as negative control. 8B: Enhanced ADCC activity against lung cancer cell lines (A549) by EGFR-blocking antibody human IgG1 (ET201) produced by CHO-1E5 cell clone adapted to serum-free medium. ET201 antibody expressed in CHO-1E5 cells was purified from the conditioned medium by Protein A chromatography; and quantified by UV280.

Figure 23:
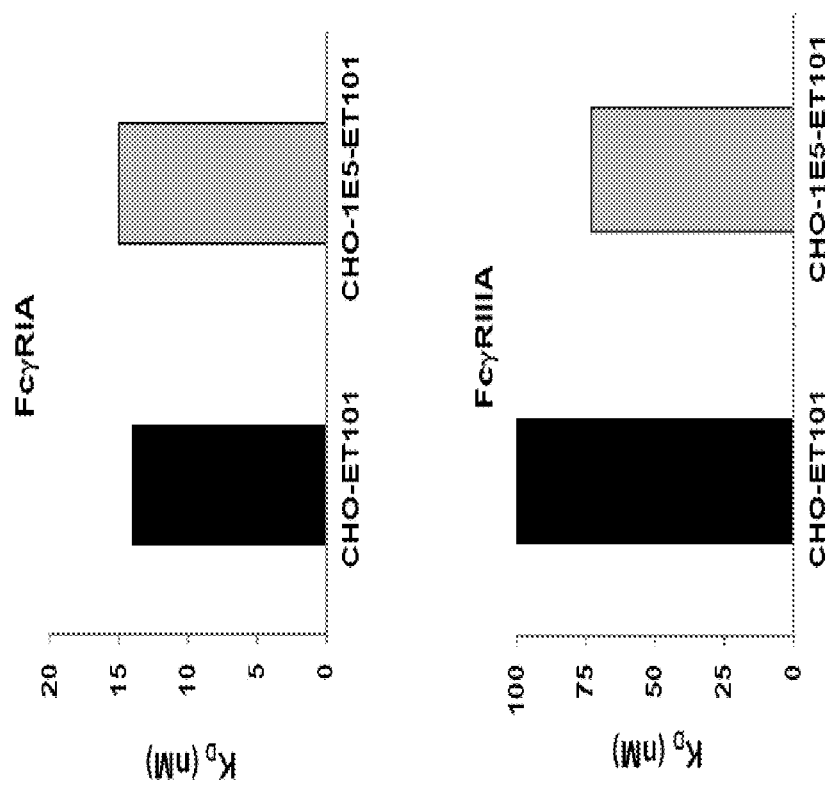

FIG. 23 shows the results of antibody/Fc receptor binding affinity. The results show that the N-glycan exhibited by CHO-1E5 cells improves antibody binding to FcγRIIIA receptor. The antibodies were first biotinylated and loaded onto the streptavidin-coated biosensor (ForteBio, Menlo Park, Calif.). Recombinant FcγRI and FcγRIIIb proteins were suspended at the concentration of 100-400 nM (R&D Systems, Minneapolis, Minn.). The binding affinity ($K_D$, nM) was assessed according to ForteBio's standard kinetics protocol.

Figure 24:
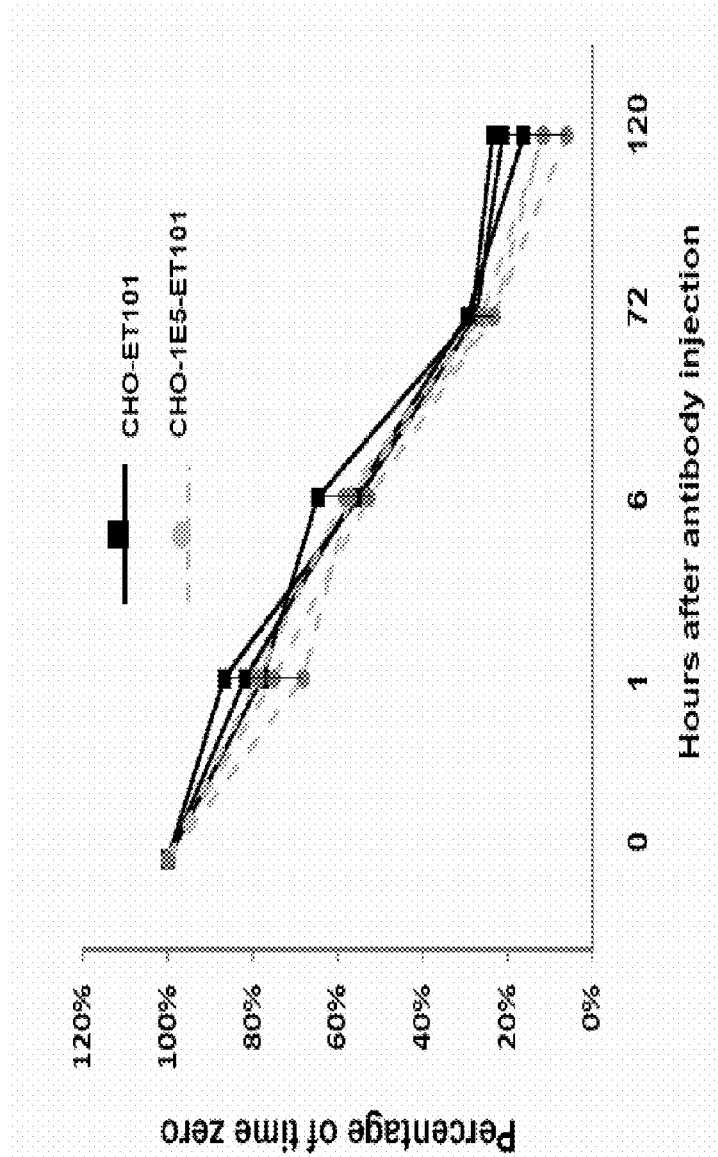

FIG. 24 shows the in vivo pharmacokinetic profile of the antibody produced by CHO-1E5 cells. The results show that the pharmacokinetics of the antibody produced by CHO-1E5 cells is substantially identical to that produced by the wild type parental CHO cells.

Figure 25:
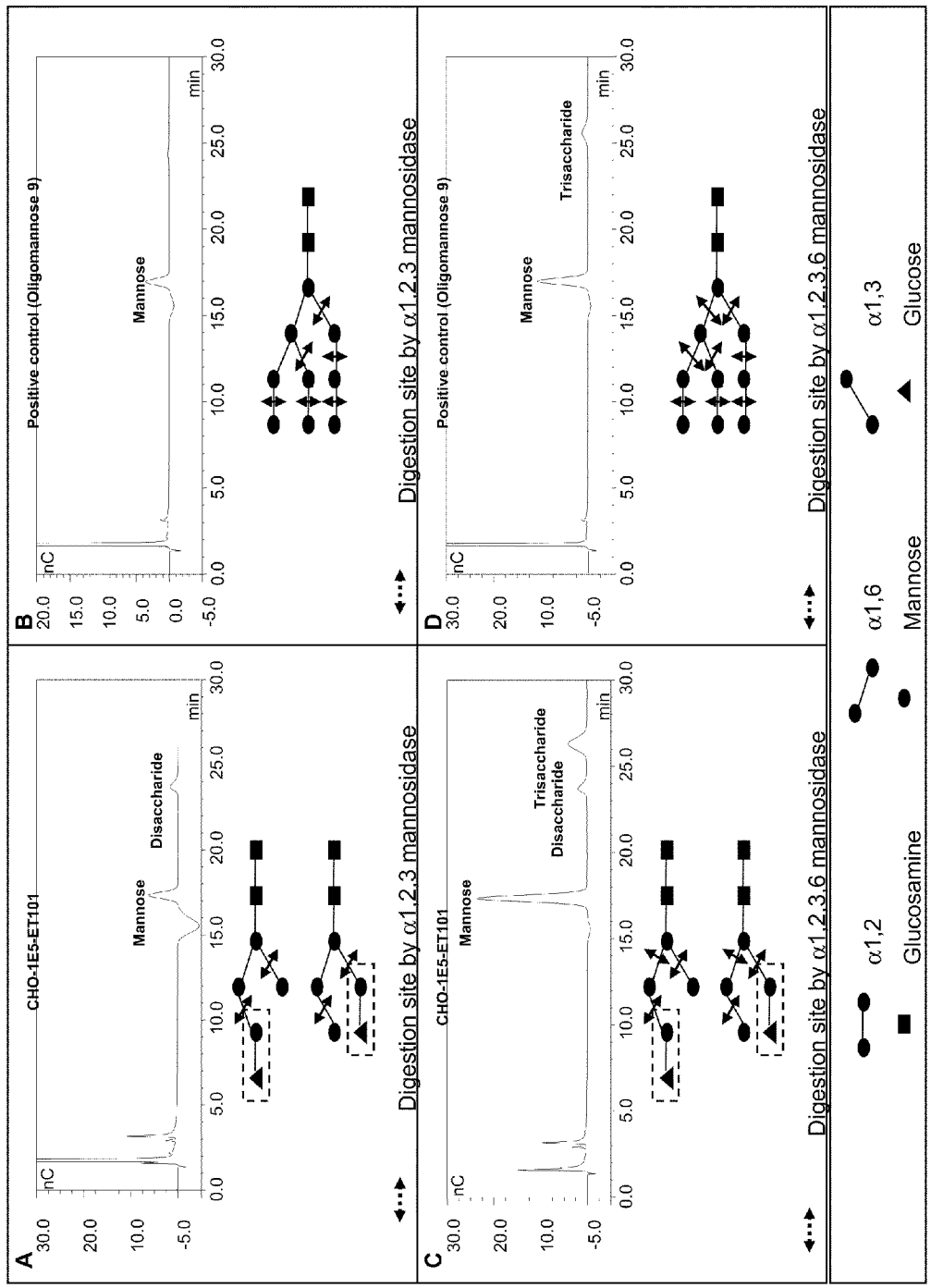

FIG. 25 shows the structural determination of the oligosaccharides produced by CHO-1E5 through the digestion of α1,2,3 mannosidase and α1,2,3,6 mannosidase. (A) the sacharides eluted by 18 mM NaOH and the α1,2,3 mannosidase digestion site of the N-glycan from the sample of 1E5 cells or a positive control (B). (C) the sacharides eluted by 18 mM NaOH and the α1,2,3,6 mannosidase digestion site of the N-glycan from the sample of 1E5 cells or a positive control (D).

Figure 26B:
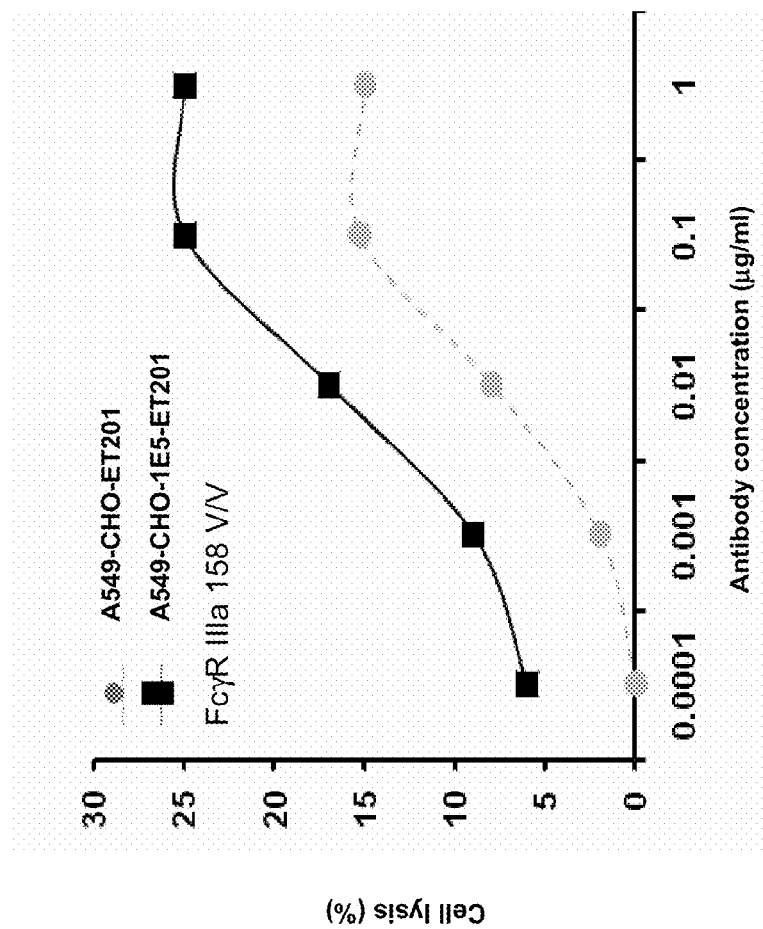

FIG. 26 shows cell lysis assays for determining antibody binding affinity to various FcγR IIIa receptors. FIG. 26a shows that the antibody with the unique glycosylation has enhanced ADCC activity when human PBMCs expressing the low binding affinity FcγR IIIa 158F/F were used as the effector cells. FIG. 26b shows binding of the antibody with the unique glycosylation to human PBMCs expressing the high affinity FcγR IIIa 158V/V.

Figure 27:
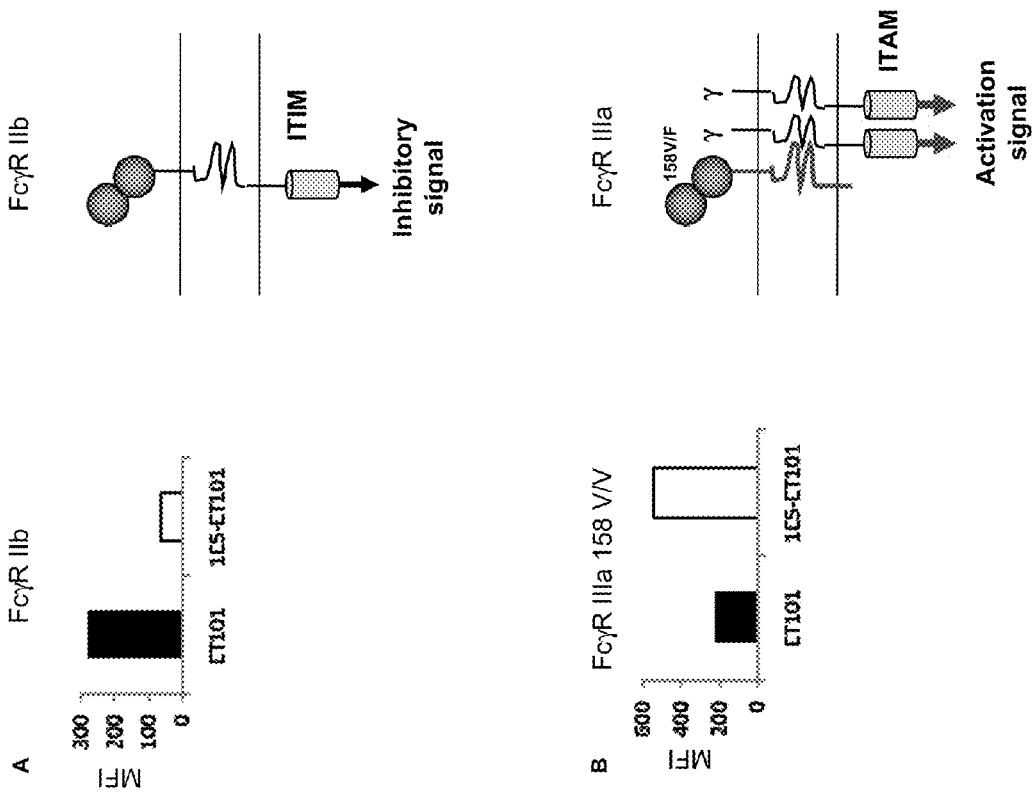

FIG. 27 shows flow cytometric measurements of the binding affinity of the antibodies produced by the parental CHO cells and the antibodies with the unique structure of the N-glycan to human FcγRs. FIG. 27A shows that the antibody with the unique structure of the N-glycan improves binding affinity to the activating FcγRIIIa receptor, and FIG. 27B shows that the antibody with the unique structure of the N-glycan reduces binding affinity to the inhibitory receptor FcγRIIb.

Figure 28:
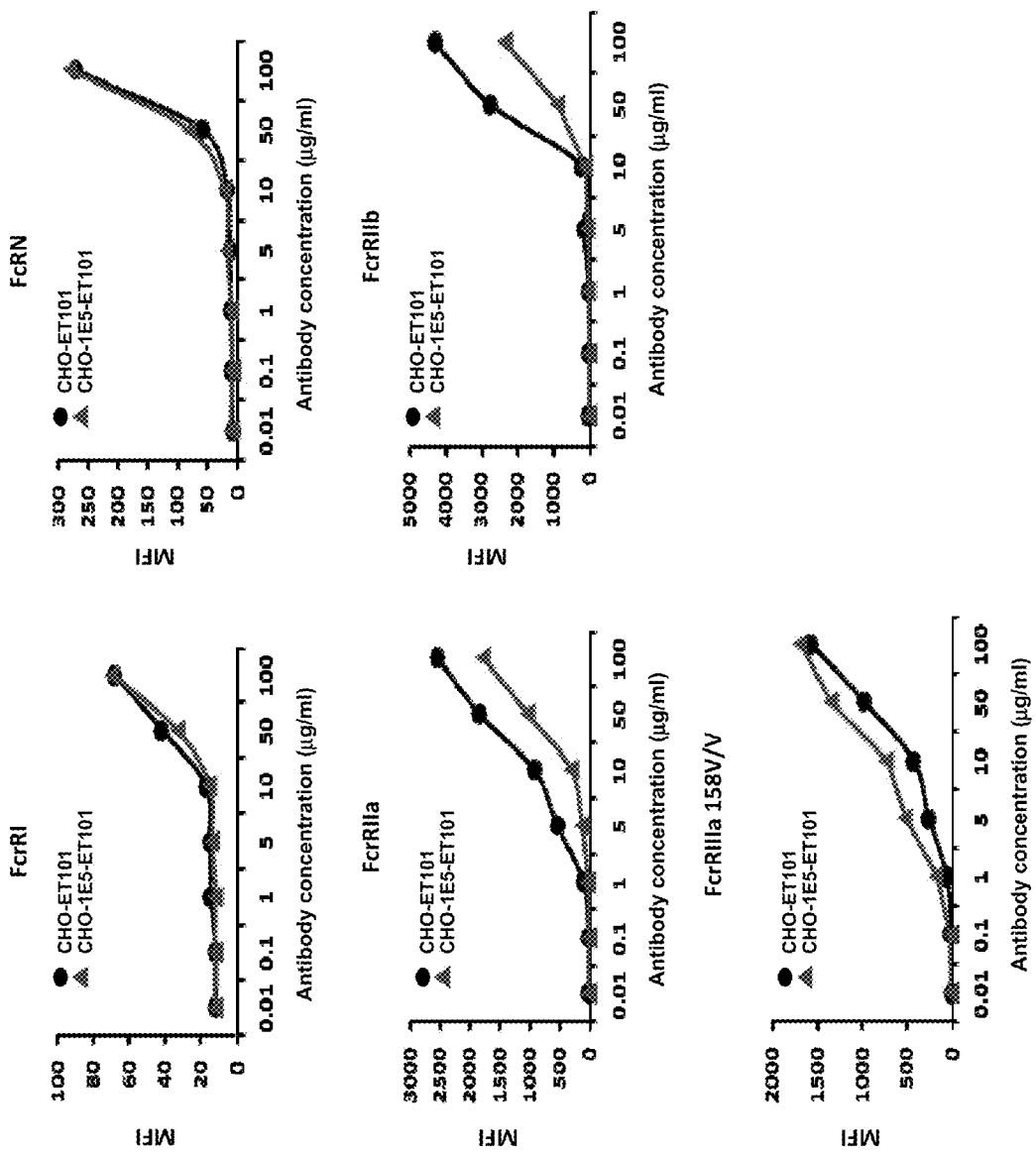

FIG. 28 shows that the antibody produced by CHO-K1-1E5 has reduced binding affinity to the inhibitory receptor FcγRIIb and has increased binding affinity to the activating receptor FcγRIIIa. CHO-K1 cells stably expressing the exogenous Fcγ receptors were detached by 20 mM EDTA/PBS and dispersed into single cells. The cells were incubated with biotinylated antibodies produced by CHO (CHO-ET101) or CHO-K1-1E5 (CHO-1E5-ET101) on ice for 1 hour. After being washed with PBS, cells were incubated with streptavidin-FITC and analyzed by FACS analysis. The geometric mean of fluorescence intensity was acquired and plotted.

Figure 29:
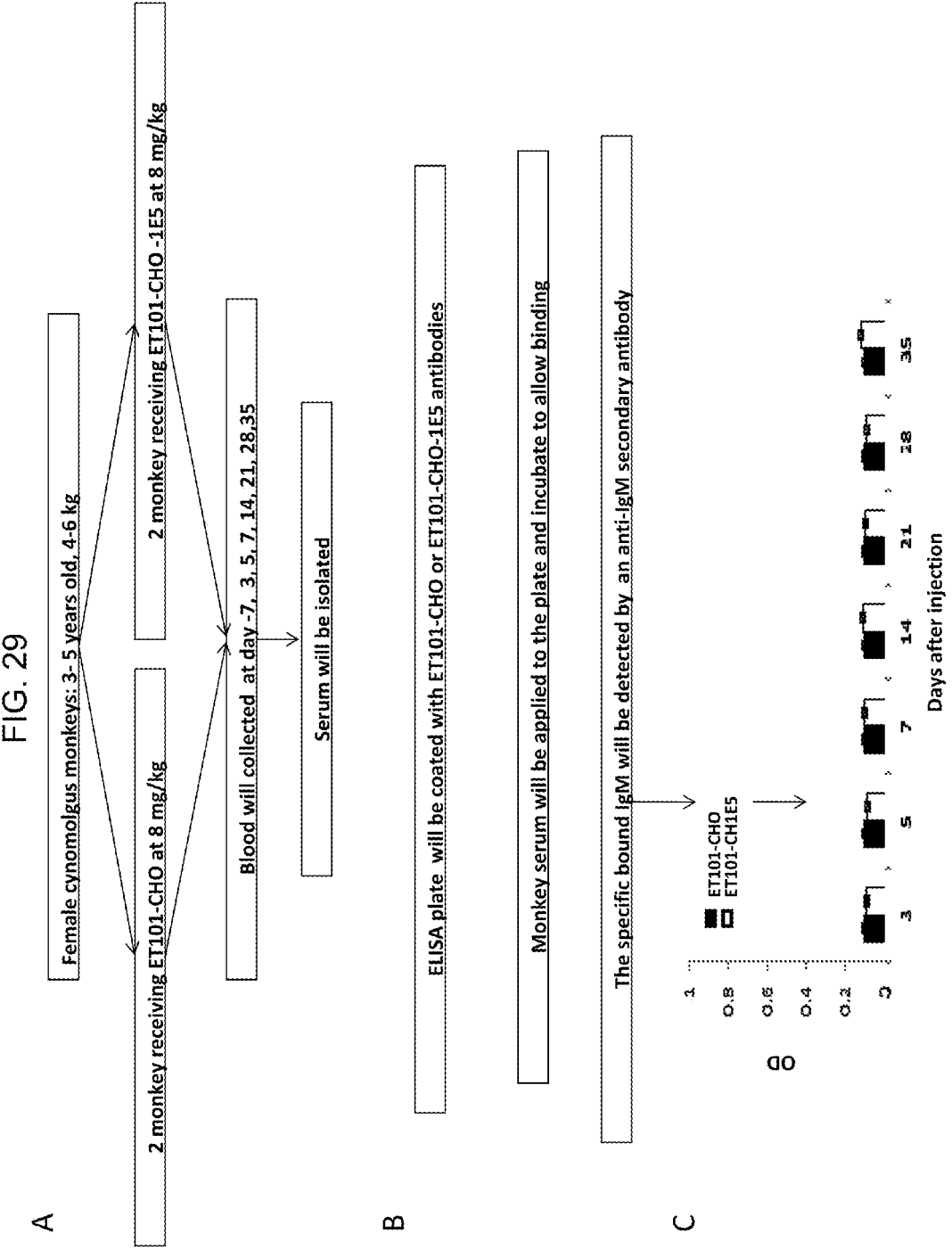

FIG. 29 shows the experimental procedure by which immunogenicity or the lack thereof of a given antibody (e.g., antibodies produced by CHO-1E5 clone) is assessed in a test animal such as primate. A) female cynomolgus monkeys receive antibody ET101 produced by wild type CHO cells, or ET101 antibody produced by CHO-1E5 cells at a dose of 8 mg/ml/kg. 0.5 ml of blood is collected 7 days before the injection and on days 3, 5, 7, 14, 21, 28, 35 after the injection. Serum samples are isolated and frozen at −80° C. B) ELISA assay is used to determine the immunogenicity of ET101-CHO-1E5 antibody in cynomolgus monkeys. The assay detects the presence of IgM in the monkey serum specific for the administered ET-101 antibodies. An ELISA plate is coated with ET101-CHO or ET101-CHO-1E5 antibodies. The isolated monkey serum samples at different dilution are applied to the plate to allow binding to coated target antibodies. The bound IgM is detected by anti-IgM secondary antibody. C) Expected ELISA results show no significant difference in immunogenicity (ET101-specific IgM levels in monkey serum) between ET101-CHO and ET101-CHO-1E5.

DETAILED DESCRIPTION

The compositions and methods of the present disclosure provide cell lines that are modified to have variant glycosylation patterns. Such cell lines can be used to produce proteins, such as antibodies with enhanced effector functions, such as increased antibody-dependent cellular cytotoxicity (ADCC) activity. The proteins typically also have variant glycosylation patterns.

Host Cells

The host cell of the present disclosure is modified to yield a variant glycosylation pattern as compared to an unmodified parental host cell. A host cell includes an individual cell, cell culture, and/or cell line. Host cells include progeny of a single host cell. A host cell can be transfected with a heterologous sequence of the present disclosure. Host cells may be prokaryotic or eukaryotic, such as bacterial cells, fungal cells, animal cells, insect cells, plant cells and the like that are capable of glycosylation.

Examples of bacterial host cells include microorganisms belonging to the genus *Escherichia, Serratia, Bacillus, Brevibacterium, Cornebacterium, Microbacterium, Pseudomonas* and the like. For example, bacterial host cells may include, but not be limited to, *Escherichia coli* XL1-Blue, XL2-Blue, DH1, MC1000, KY3276, W1485, JM109, HB101, No. 49, i W3110, NY49, G1698, or TB1. Other bacterial host cells may include, but not be limited to, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 13869, *Corynebacterium acetoacidophilum* ATCC 13870, *Microbacterium ammoniaphilum* ATCC 15354, *Pseudomonas putida, Pseudomonas* sp. D-0110 and the like.

Yeast host cells may include microorganisms belonging to the genus *Saccharomyces, Schizosaccharomyces, Kluyveromyces, Trichosporon, Schwanniomyces, Pichia, Candida* and the like, such as *Saccharomyces cerevisiae, Schizosaccharomyces pombe, Kluyveromyces lactis, Trichosporon pullulans, Schwanniomyces alluvius, Candida utilis* and the like.

Other examples of eukaryotic cells include animal cells such as mammalian cells. For example, host cells preferably include, but are not limited to, Chinese hamster ovary cells (CHO) or monkey cells, such as COS cells. The CHO cells may include, but not be limited to, CHO/dhfr⁻ or CHO/DG44 cells. The Chinese hamster ovary tissue-derived CHO cell includes any cell which is a cell line established from an ovary tissue of Chinese hamster (*Cricetulus griseus*). Examples include CHO cells described in documents such as *Journal of Experimental Medicine*, 108, 945 (1958); *Proc. Natl. Acad. Sci. USA*, 60, 1275 (1968); *Genetics*, 55, 513 (1968); *Chromosoma*, 41, 129 (1973); *Methods in Cell Science*, 18, 115 (1996); *Radiation Research*, 148, 260 (1997); *Proc. Natl. Acad. Sci. USA*, 77, 4216 (1980); *Proc. Natl. Acad. Sci.*, 60, 1275 (1968); *Cell*, 6, 121 (1975); *Molecular Cell Genetics*, Appendix I, II (pp. 883-900); and the like. In addition, CHO-K1 (ATCC CCL-61), DUXB11 (ATCC CCL-9096) and Pro-5 (ATCC CCL-1781) registered in ATCC (The American Type Culture Collection) and a commercially available CHO-S (Life Technologies, Cat #11619) or sub-cell lines obtained by adapting the cell lines using various media can also be exemplified.

In an alternative embodiment the parent cell line is derived from a lymphocytic lineage cell line, such as a B cell line. The host cell may be from cell lines used in hybridoma production. They can be myeloma cells, such as from murine myeloma lines, such as, but not limited to, MOPC-21, MPC-11, NS0, SP-2, Sp2/0, S 194, and X63-Ag8-653 cells; human myeloma cell lines, such as, but not limited to, Namalwa, Karpas 707H, RPMI 8226, 8226 AR/NIP4-1, KM-2R, and U-266; or rat myeloma cell lines, such as, but not limited to, YB2/0, YB2/3.0.Ag.20, Y3-Ag1.2.3, IR983F. Cell lines, such as HeLa, HEK-293, NIH3T3, COS, CHO, NS0, PER.C6, K562, L1.2, JY, BHK, K562, 293F, 3T3, and Jurkat may also be used in the present disclosure. For example, in some embodiments, the host cell is a CHO-1E5, CHO-3F, or CHO-2.6 clone.

Examples of insect host cells include *Spodoptera frugiperda* ovary cells, such as Sf9 and Sf21 (*Baculovirus Expression Vectors, A Laboratory Manual*, W. H. Freeman and Company, New York (1992)); a *Trichoplusia ni* ovary cell such as High 5 (manufactured by Invitrogen); and the like. Examples of plant host cells include plant cells of tobacco, potato, tomato, carrot, soybean, rape, alfalfa, rice, wheat, barley and the like.

The modified host cells of the present disclosure may be grown in cultures, and in any apparatus that may be used to grow cultures, including fermetors. They may be grown as monolayers or attached to a surface. Alternatively, the host cells may be grown in suspension. The cells can be grown in a culture medium that is serum-free. The media can be a commercially available media, such as, but not limited to, Opti-CHO (Invitrogen, Catalogue #12681) supplemented with glutamine, such as 8 mM L-glutamine. The modified host cells can maintain its variant glycosylation pattern for a number of passages in culture. For example, the modified host cell can maintain its variant glycosylation pattern after at least approximately 20, 30, 40, or 50 passages. In some embodiments, the modified host cell can maintain its variant glycosylation pattern after at least approximately 60 passages. In yet other embodiments, the modified host cell can maintain its variant glycosylation pattern after at least approximately 100, 150, 200, 500, or 1000 or more passages.

In some embodiments, the host cell is a non-lymphocytic cell. A lymphocyte is a type of white blood cell in the vertebrate immune system. Lymphocytes typically include T cells, B cells and natural killer (NK) cells. A non-lymphocytic cell encompasses any type of cell that is not a lymphocyte. The host cell of the invention may have a species origin selected from the group consisting of human, mouse, rat, fruit fly, worm, yeast and bacterium. The host cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids. The host cells producing the N-glycan may be derived from any developmental stage including embryo and adult stages, as well as developmental origin such as ecotodermal, mesodermal, and ectodermal origin. In some embodiments, the host cells are CHO, NS0, SP2/0, HEK293, PER.C6 or YB2/0 cells.

Generating Modified Cell Lines

The present disclosure provides methods for generating and selecting host cells that are modified to yield a variant glycosylation pattern. The method of selecting a host cell with a modified glycosylation pattern can comprise providing a plurality of host cells; introducing random genetic mutation (s) to the plurality of host cells; and selecting from the plurality of cells at least one cell that exhibits a variant glycosylation pattern characterized by a change in the level of at least one type of sugar molecules as compared to a corresponding parental cell that has not been subject to the random genetic mutation. The host cell may be any of those described herein, including eukaryotic cells such as CHO cells or YB2.0 cells.

The genetic mutation(s) can be induced by mutagens. The mutagens may be, but are not limited to, genetic, chemical or radiation agents. For example, the mutagen may be ionizing radiation, such as, but not limited to, ultraviolet light, gamma rays or alpha particles. Other mutagens may include, but not be limited to, base analogs, which can cause copying errors; deaminating agents, such as nitrous acid; intercalating agents, such as ethidium bromide; alkylating agents, such as bromouracil; transposons; natural and synthetic alkaloids; bromine and derivatives thereof; sodium azide; psoralen (for example, combined with ultraviolet radiation). The mutagen may be a chemical mutagen such as, but not limited to, ICR191, 1,2,7, 8-diepoxy-octane (DEO) or ethyl methane sulfonate (EMS). Different mutagens may be combined, either sequentially or concurrently, when introduced into a host cell.

Figure 1:
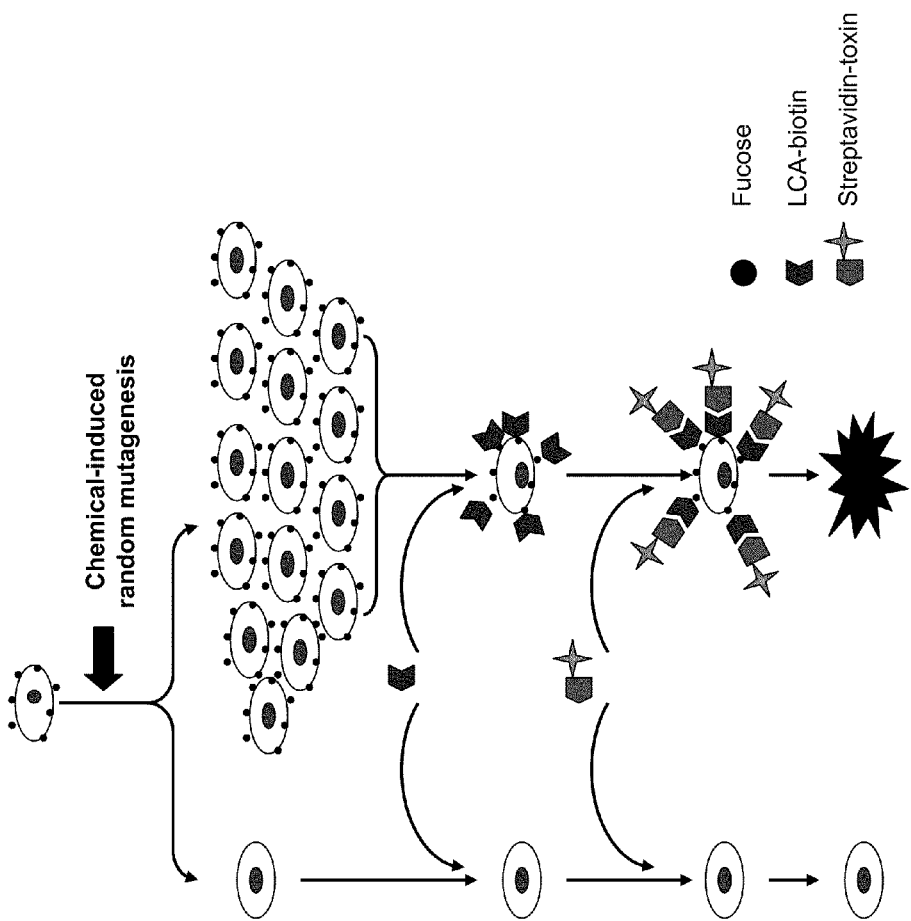
FIG. 1 is a schematic of a strategy to enrich CHO-K1 cells with low fucose after chemical-induced random mutagenesis. CHO-K1 cells are treated with chemicals to induce random mutations. As the chance to generate fucosylation-silencing mutation is rare, a unique process to deplete the cells with high fucose by using LCA-biotin and stretavidin-saporin is used. These two reagents are first mixed to form biotin-streptavidin complex in culture medium. After the chemical-induced mutagenesis, the complex was added to the cells.

Methods may include those as shown in FIGS. 1 and 2, or as described in Example 2. For example, to modify a host cell population to acquire modified host cells with a variant glycosylation pattern, one or more mutagen, such as chemical mutagens, can be applied to cells to cause random genetic mutations. Chemical-induced random mutagenesis can lead to mutations of genes that control or regulate sugar biogenesis and protein glycosylation processes, such as, but not limited to, fucosylation, mannosylation, and/or N-acetylglucosaminylation. The chemical mutagen may also selectively kill host cells with a particular glycosylation pattern, such as one with high fucosylation. Thus, stable clones with reduced levels of fucosylation after mutagenesis can be enriched and isolated by selecting the cells with LCA-toxin, which specifically targets and eliminates cells with high fucosylation (see FIGS. 1 and 2, Example 2). The host cells that have been genetically modified to have a variant glycosylation pattern can be selected to be maintained in a serum free medium, grown in suspension, and/or grown in a fermentor. The modified host cells may also produce glycoproteins that can be harvested or collected. The glycoproteins may be secreted, exhibit a variant glycosylation pattern, and/or have a therapeutic use, as further described herein. The glycoproteins may be encoded by a heterologous sequence and/or be an antibody, such as an antibody with increased ADCC activity as compared to a corresponding antibody produced in an unmodified parental host cell, as further described herein.

The glycosylation patterns of the parental host cell can be compared to the variant glycosylation pattern of a modified host cell, and can be evidenced by a change in the level of one or more types of sugar molecules. For example, the variant glycosylation pattern can be characterized by a change in at least two types of glycosylation selected from the group consisting of: fucosylation, mannosylation, and N-acetylglucosaminylation, as further described below. Furthermore, the variant glycosylation pattern can be evidenced by a change in level of glucose and/or galactose, such as an increase in glucose and a decrease in galactose. Additional variations are described as follows.

Glycosylation Patterns

The host cell of the present disclosure is modified to yield a variant glycosylation pattern characterized by, e.g., a change in levels of at least two types of sugar molecules present on a surface of the host cell as compared to the unmodified parental host cell. The host cells of the present disclosure may also be used to produce proteins or glycoproteins. The proteins may be antibodies or enzymes, and may be used as therapeutics. Furthermore, the glycoproteins may be secreted. The proteins may be heterologous proteins, such as proteins produced from the introduction of heterologous sequences into the modified host cell exhibiting a variant glycosylation pattern. Heterologous means derived from a genotypically distinct entity from the rest of the entity to which it is being compared and can be applied to a polynucleotide, such as a nucleic acid sequence, or a polypeptide, which means that the polynucleotide or polypeptide or protein.

The proteins or glycoproteins of the present disclosure can be endogenous or heterologous, and are produced in a host cell that has been modified to exhibit a variant glycosylation pattern. The glycoproteins may also exhibit a variant glycosylation pattern, which may be characterized by a change in levels of at least two types of sugar molecules as compared to a corresponding wildtype glycoprotein (ie. a glycoprotein produced in an unmodified host cell). The sugar molecules may be directly attached to the glycoprotein (for example, N- or O-linked to the glycoprotein), or indirectly (for example, linked through other sugars that are N- or O-linked to the glycoprotein). Sugar chain structure variations, or variant glycosylation patterns, due to various sugar molecule content in such chains play an important role in the effector function of glycoproteins. For example, variant glycosylation patterns of a glycoprotein can increase the effector function of the glycoprotein, such as increase the antibody-dependent cellular cytotoxicity (ADCC) activity of an antibody.

The glycosylation pattern of a host cell may be N- or O-glycosylation of any proteineous moiety, wherein the addition of one or more sugar molecules may be at the amide nitrogen of asparagine or the hydroxyl oxygen of hydroxylysine, hydroxyproline, serine, or threonine, respectively. The glycosylation pattern may be characterized by a change the levels of at least two or more sugar molecules or saccharides, such as monosaccharides, disaccharides, polysaccharides or oligosaccarhides. For example, the sugar molecules may be trioses, tetrososes, pentoses, hexoses, heptoses, octoses, nonoses, or derivatives thereof, such as deoxy sugars, such as deoxyhexoses; N- or O-substituted derivatives, such as sialic acid; or sugars with amino groups. The sugar molecules may include, but not be limited to, galactose (Gal), glucose (Glc), mannose (Man), N-acetylneuraminic acid (NeuAc), fucose (Fuc), N-Acetylgalactoseamine (GalNAc), N-Acetylglucosamine (GlcNAc); and Xylose (Xyl). The sugar molecules may be linked to other sugar molecules via α or β linkage.

The variant glycosylation pattern of the present disclosure may be evidenced by a change in level of at least two types of sugar molecules and can be evidenced by the change of different types of glycosylation of the host cell or glycoprotein. For example, the level of fucosylation, mannosylation, N-acetylglucosaminylation and/or combinations thereof may be used as evidence of a variant glycosylation pattern. For example, the level of fucosylation, mannosylation, and/or N-acetylglucosaminylation can be reduced or increased in a modified host cell as compared to an unmodified parental cell. The level of fucosylation, mannosylation, and/or N-acetylglucosaminylation of a glycoprotein can be reduced or increased as compared to a corresponding wildtype glycoprotein (ie. produced in an unmodified parental host cell). For example, the heterologous glycoprotein may exhibit a reduced level of fucose, mannose, and/or of N-acetylglucosamine content as compared to a corresponding wildtype glycoprotein produced by said unmodified host cell. The glycosylation can involve α- or β-linked sugars, such as α- or β-linked mannose or α- or β-linked N-acetylglucosamine. Furthermore, the host cell with a variant glycosylation pattern may still contain the 1,6-fucosyltransferase gene activity and/or maintain it; as compared to that of the unmodified parental host cell.

Figure 10A:
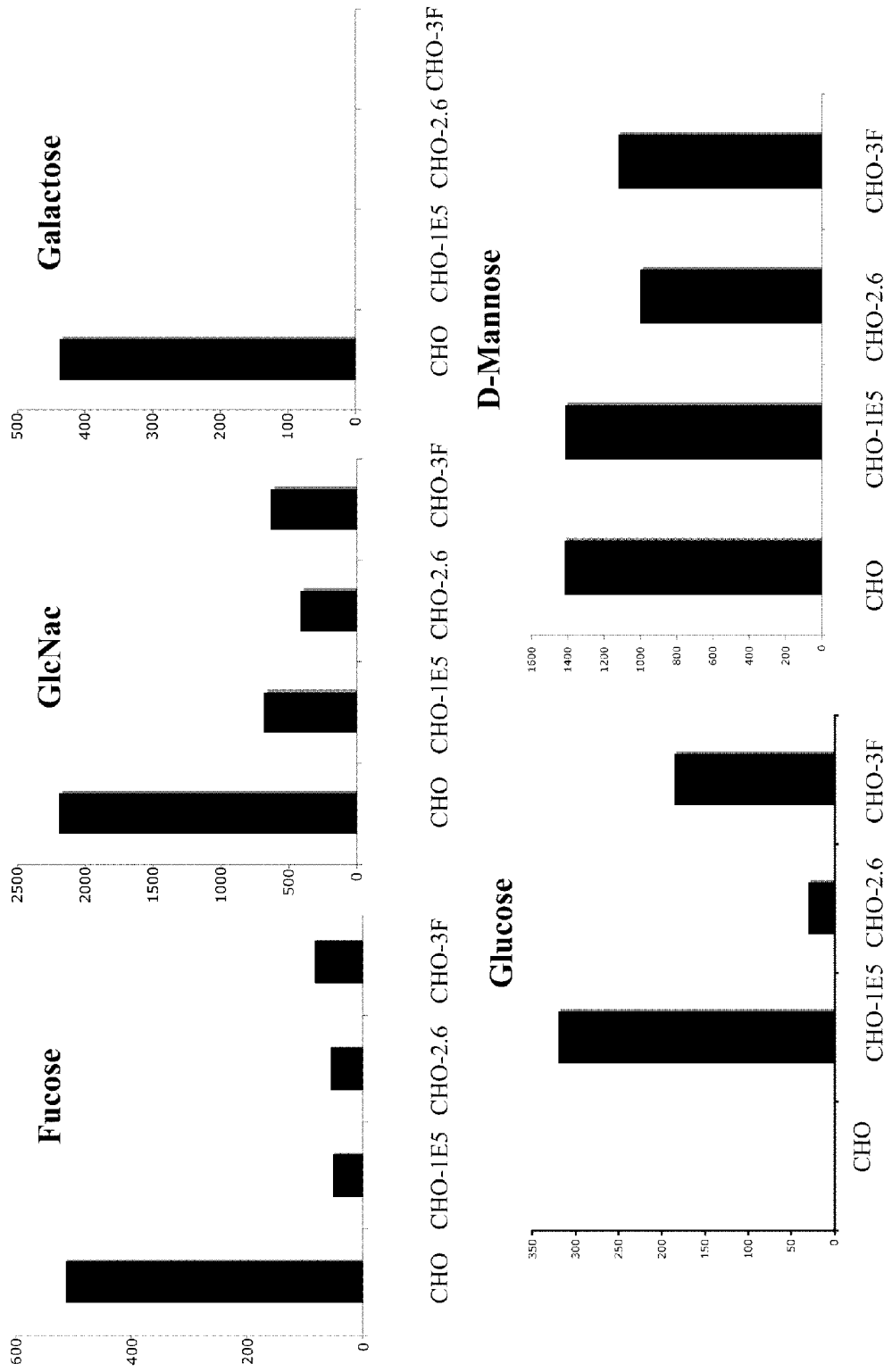

The variant glycosylation pattern of the present disclosure can also be evidenced by a change in level of glucose, galactose, or both, as compared to an unmodified parental cell. For example, the change can be an increase or decrease in galactose levels. The change can also be an increase or decrease in glucose levels. In some embodiments, the change can be an increase in glucose levels, a decrease in galactose levels, or an increase in glucose levels and a decrease in galactose levels, such as shown in FIG. 10A, B. The variant glycosylation pattern can comprise a change in glucose and/or galacatose, with changes in levels of other monosaccharides, such as, but not limited to, fucose, glucuse, mannose, and N-acetylglucosamine, such as shown in FIGS. 16 and 20. Different combinations of sugars and varying levels of such sugars, for example, an increase or decrease in levels as compared to a parental cell, is contemplated herein.

The variant glycosylation pattern may be evidenced by a change in level of at least two types of sugar molecules, wherein the change in level of at least one type of sugar molecule is at least approximately two fold. Alternatively the change in level is at least approximately two fold for at least two types of sugars. The change may be an increase or decrease in the level of sugar molecules. The change in level may be at least approximately 3, 4, 5, 6, 7, 8, 9, 10, 15, 20, 25, 30, 50, 75, 100, 500, 1000 fold, or even higher.

In some embodiments, the present invention provides compositions comprising a subject N-linked glycan, when exhibited on an antibody, results in an enhanced antibody-dependent-cell-cytotoxicity (ADCC) activity of the antibody. N-linked glycans are attached to the amide nitrogen of asparagine side chains of a protein. There are three major types of N-linked saccharides: high-mannose oligosaccharides, complex oligosaccharides and hybrid oligosaccharides. High-mannose N-linked glycan typically comprises two N-acetylglucosamines with many mannose residues. Complex oligosaccharides typically contain almost any number of the other types of saccharides. Proteins can be glycosylated by both types of oligos on different portions of the protein. N-linked glycans can be modified with a variety of different monosaccharides including glucose, mannose, galactose, N-acetylglucosamine, N-acetylgalactosamine, fucose and sialic acid.

Figure 15:
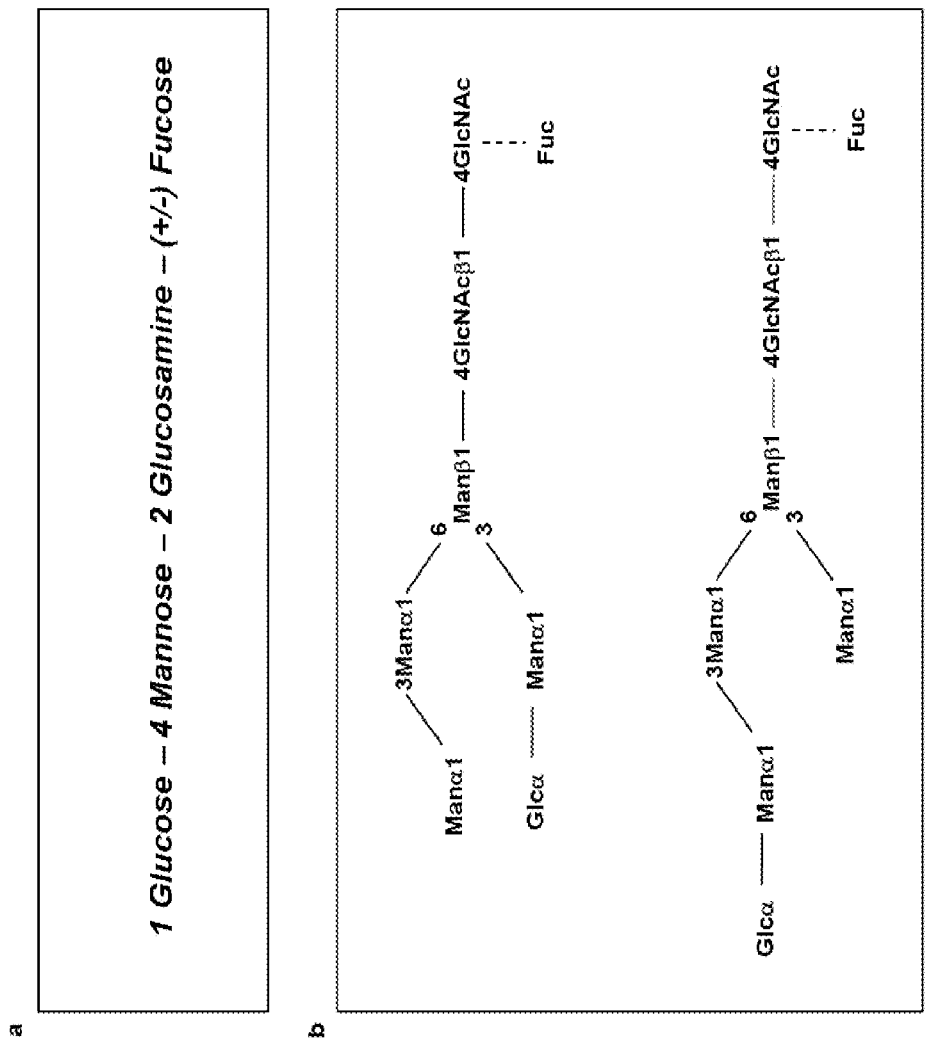

The subject N-linked glycan composition and structure of the N-linked oligosaccharide can be produced by an exemplary modified CHO cell clone designated as CHO-1E5. A single N-glycan structure on antibody is produced by CHO-1E5. The CHO-1E5 has altered N-glycan biosynthesis and the antibodies produced by this host cell clone exhibit a glycosylation profile consisting of glucose, mannose, and N-acetylglucosamine with or without fucose. The structural formula of the N-glycan has been demonstrated as Glu-GlcNAC$_2$-Man$_4$ (+/−Fuc). This glycan has the basic structure of core N-linked oligosaccharide: 3Man-2 GluNAc with or without fucose but lacks two outside acetylglucosamine. There is a glucose molecule and an extra mannose molecule attached to one of the side chains of the core oligosaccharide (FIG. 15). In some embodiments, the glycosylation pattern represents a composition of structural formula (I), in which a fucose moiety can optionally be linked to the first 4GlcNAc from the right:

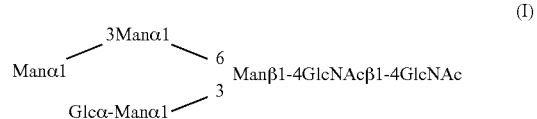
(I)

In some embodiments, the glycosylation pattern represents a composition of structural formula (II), in which a fucose moiety can optionally be linked to the first 4GlcNAc from the right.

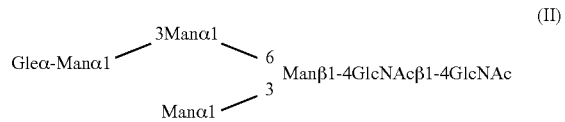
(II)

The structural formulae (I) and (II) depicted hereinabove and in FIG. 15 show that a fucose molecule can be present or absent from the subject N-linked glycan. In some embodiments, the subject N-linked glycan comprises one glucose molecule. In some embodiments, the glucose molecule is at a terminus (i.e. terminal glucose) of the subject N-linked glycan. In some embodiments, the subject N-linked glycan comprises one or more terminal glucose molecules. In some embodiments, the subject N-linked glycan comprises four mannose molecules. In some embodiments, the subject N-linked glycan comprises two N-acetylglucosamine molecules.

In some embodiments, the glycosylation pattern represents a mixed composition of structural formulas (I) and (II). In some embodiments, the N-glycan synthesized by a modified host cell of the present invention designated as CHO-1E5 lacks galactose, has reduced levels of fucose and N-acetylglucosamine, and contains a terminal glucose as compared to the N-glycan produced by the wild type parental host cells (FIG. 16). In some embodiments, the N-glycan exhibited by CHO-1E5 clone is characterized as a single peak by MALDI-TOF MS analysis, suggesting a substantially homogeneous population of oligosaccharides.

The glycosylation pattern of a host cell or glycoprotein can be detected using agents that specifically, or preferentially recognizes or binds specific sugar molecules or the proteinaceous moieties that are associated or modified with the specific sugar molecules. Agents may include, but not be limited to, *Lens culimaris* agglutinin-A (LCA) is a chemical that specifically binds to proteins modified with fucose; wheat germ agglutinin (WGA), which has preferential binding to N-acetylglucosamine; concanavalin A (Con A), which recognizes α-linked mannose; and *Griffonia* (Bandeiraea) *Simplicifolia* Lectin II (GS-II), which binds to α- or β-linked N-acetylglucosamine residues.

The agents may be detected directly or indirectly. For example, the agents may be conjugated to a label. Any detectable label can be used, such as a fluorescent label. Detections methods known in the arts, such as flow cytometry may be used to detect and/or separate labeled cells. For example, detection and/or separation may be by fluorescence activate cell sorting (FACS). Labels may include fluorescein or its derivatives, such as fluorescein isothiocyanate (FITC), Oregon Green, Tokyo Green, SNAFL, carboxynaphthofluorescein (CFSE), Carboxyfluorescein diacetate succinimidyl ester (CFDA-SE), DyLight 488, Alexa Fluor 488, green fluorescent protein (GFP), phycoerythrin (PE), Peridinin Chlorophyll protein (PerCP), PE-Alexa Fluor 700, PE-Cy5 (TRI-COLOR), PE-Cy5.5, PE-Alexa Fluor 750, PE-Cy7, allophycocyanin (APC), APC-Cy7, and derivatives thereof. The aforementioned labels may also be used to analyze the glycosylation patterns of glycoproteins. Alternatively, the agents may be detected directly, for example, by using antibodies to detect the agents, such as by Western blotting and other methods well known in the arts.

Other methods to analyze the glycosylation pattern may include compositional analysis of different types of sugars, such as neutral sugars and sugars with amino groups. For example, neutral sugars, such as galactose, mannose, fucose or the like, and sugars with amino groups, such as N-acetylglucosamine or the like, and an acidic sugar, such as sialic acid or the like can be analyzed. The compositional ratio can be analyzed by releasing neutral sugars or amino sugars by acid hydrolysis of the sugar chain. Methods man include, but not be limited to, a method using a sugar composition analyzer (BioLC) manufactured by Dionex. The BioLC is an apparatus for analyzing sugar composition by HPAEC-PAD (high performance anion-exchange chromatography-pulsed amperometric detection) method (Rocklin et al., *J. Lig. Chromatogr.* 6(9), 1577-1590 (1983)). The compositional ratio can also be analyzed by a fluorescence labeling method using 2-aminopyridine (PA). Specifically, the compositional ratio can be calculated by fluorescence-labeling an acid-hydrolyzed sample with 2-aminopyridine in accordance with a known method (Kondo et al., *Agric. Biol. Chem.*, 55(1), 283-284 (1991)) and carrying out HPLC analysis.

The glycosylation pattern can also be analyzed by a two-dimensional sugar chain mapping method (Tomiya et al., *Anal Biochem.*, 171, 73-80 (1988); *Biochemical Experimentation Method 23—Method for Studying Glycoprotein Sugar Chains* (*Gakkai Shuppan Center*), edited by Reiko Takahashi (1989)). The two-dimensional sugar chain mapping method is a method in which the sugar chain structure is estimated, for example, by plotting the retention time or eluting position of the sugar chain by reverse phase chromatography as the X axis and the retention time or eluting position of the sugar chain by a normal phase chromatography as the Y axis, and comparing the results with those of known sugar chains.

The sugar chain can be released by hydrazinolysis and then fluorescence labeling of the sugar chain with 2-aminopyridine (Hase et al, *J. Biochem.*, 95, 1973203 (1984)) is carried out. The sugar chain is separated from an excess PA reagent and the like by gel filtration and subjected to reverse phase chromatography. Subsequently, each peak of the fractionated sugar chain is analyzed by normal phase chromatography. Based on these results, the sugar chain structure can be estimated by plotting the spots on a two-dimensional sugar chain map and comparing them with those of sugar chain standards (manufactured by Takara Shuzo) or a reference (Tomiya et al., *Anal Biochem.*, 171, 73-80 (1988)).

In addition, the glycosylation pattern can be analyzed by mass spectrometry, such as MALDI-TOF-MS or the like, of each sugar chain.

Heterologous Sequences

The host cells of the present disclosure modified to yield variant glycosylation patterns may comprise a heterologous sequence. The heterologous sequence may comprise a nucleic acid sequence. As used herein, nucleic acid sequence is used interchangeably with polynucleotide, nucleotide, nucleotide sequence, nucleic acid and oligonucleotide. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The heterologous sequence of the present disclosure can encode a proteinaceous moiety, which refers to proteins, polypeptides, peptides, amino acid sequences, which encompasses polymers of amino acids of any length. The polymer may be linear or branched, it may comprise modified amino acids, and it may be interrupted by non-amino acids. The proteinaceous moiety encompasses an amino acid polymer that has been modified, for example, disulfide bond formation, glycosylation, lipidation, acetylation, phosphorylation, or any other manipulation, such as conjugation with a labeling component. Furthermore, amino acid refers to either natural and/or unnatural or synthetic amino acids, including but not limited to glycine and both the D or L optical isomers, and amino acid analogs and peptidomimetics. Standard single or three letter codes are used to designate amino acids.

The proteins encoded by the heterologous sequences of the present disclosure are typically glycoproteins, and may include, but not be limited to, enzymes or immunologically functional molecules, such as antibodies. A modified cell line yielding a variant glycosylation pattern may express a heterologous sequence that produces an antibody (humanized or chimeric), antibody fragment, cytokine, hormone or any other protein of interest. The protein produced by the cell line may be secreted by the cells and harvested. Alternatively, the cells may be harvested and protein extracted from the cells. The proteins, or glycoproteins, may be used therapeutically, to effect beneficial or desired results.

The heterologous sequence may comprise a vector, which is a nucleic acid molecule, preferably self-replicating, which transfers an inserted nucleic acid molecule into and/or between host cells. Vectors may include those that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An expression vector is a polynucleotide which, when introduced into an appropriate host cell, can be transcribed and translated into a polypeptide(s).

The heterologous sequence encoding a protein can be expressed by a single or multiple vectors. The nucleic acid sequences can be arranged in any order in a single operon, or in separate operons that are placed in one or multiple vectors. Where desired, two or more expression vectors can be employed, each of which contains one or more heterologous sequences operably linked in a single operon. Linked refers to the joining together of two more chemical elements or components, by whatever means including chemical conjugation or recombinant means. Operably-linked refers to a juxtaposition wherein the components so described are in a relationship permitting them to function in their intended manner. For instance, a promoter sequence is linked, or operably linked, to a coding sequence if the promoter sequence promotes transcription of the coding sequence.

While the choice of single or multiple vectors and the use of single or multiple promoters may depend on the size of the heterologous sequences and the capacity of the vectors, it will largely dependent on the overall yield of a given glycoprotein that the vector is able to provide when expressed in a selected host cell. In some instances, two-operon expression system provides a higher yield of glycoproteins. The subject vectors can stay replicable episomally, or as an integral part of the host cell genome.

The heterologous sequences of the present disclosure can be under the control of a single regulatory element. In some cases, the heterologous nucleic acid sequences are regulated by a single promoter. In other cases, the heterologous nucleic acid sequences are placed within a single operon. In still other cases, the heterologous nucleic acid sequences are placed within a single reading frame.

Preparation of the subject nucleic acids can be carried out by a variety of routine recombinant techniques and synthetic procedures. Standard recombinant DNA and molecular cloning techniques are well known in the art and are described by Sambrook, J., Fritsch, E. F. and Maniatis, *T. Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N. Y. (1984) and by Ausubel, F. M. et al, *Current Protocols in Molecular Biology*, pub. by Greene Publishing Assoc. and Wiley-Interscience (1987). Briefly, the subject nucleic acids can be prepared genomic DNA fragments, cDNAs, and RNAs, all of which can be extracted directly from a cell or recombinantly produced by various amplification processes including but not limited to PCR and rt-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (for example, Matteuci et al, *Tet. Lett.* 521:719 (1980); U.S. Pat. No. 4,500,707 to Caruthers et al.; and U.S. Pat. Nos. 5,436,327 and 5,700,637 to Southern et al.).

Regulatory elements include, for example, promoters and operators, which can also be engineered to increase the expression of one or more heterologous sequences encoding a glycoprotein. A promoter is a sequence of nucleotides that initiates and controls the transcription of a nucleic acid sequence by an RNA polymerase enzyme. An operator is a sequence of nucleotides adjacent to the promoter that functions to control transcription of the desired nucleic acid sequence. The operator contains a protein-binding domain where a specific repressor protein can bind. In the absence of a suitable repressor protein, transcription initiates through the promoter. In the presence of a suitable repressor protein, the repressor protein binds to the operator and thereby inhibits transcription from the promoter.

In some embodiments of the present disclosure, promoters used in expression vectors are inducible. In other embodiments, the promoters used in expression vectors are constitutive. In some embodiments, one or more nucleic acid sequences are operably linked to an inducible promoter, and one or more other nucleic acid sequences are operably linked to a constitutive promoter. Non-limiting examples of suitable promoters for use in eukaryotic host cells include, but are not limited to, a CMV immediate early promoter, an HSV thymidine kinase promoter, an early or late SV40 promoter, LTRs from retroviruses, and a mouse metallothionein-I promoter.

The genes in the expression vector typically will also encode a ribosome binding site to direct translation (that is, synthesis) of any encoded mRNA gene product. Other regulatory elements that may be used in an expression vector include transcription enhancer elements and transcription terminators. See, for example, Bitter et al, *Methods in Enzymology*, 153:516-544 (1987).

An expression vector may be suitable for use in particular types of host cells and not others. One of ordinary skill in the art, however, can readily determine through routine experimentation whether a particular expression vector is suited for a given host cell. For example, the expression vector can be introduced into the host organism, which is then monitored for viability and expression of any genes contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other transformation methods include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector. Those of ordinary skill can identify genetically modified host cells using these or other methods available in the art.

For example, the introduction of various heterologous sequences of the disclosure into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reveres-transcription coupled PCR, Northern blot hybridization, or by immunoassays using antibodies reactive with the encoded gene product. Exemplary immunoassays include but are not limited to ELISA, radioimmunoassays, and sandwich immunoassays.

Furthermore, the introduction of various heterologous sequences of the disclosure into a host cell can be confirmed by the enzymatic activity of an enzyme that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

Antibody Production

In one aspect, the present disclosure provides host cells, modified to yield a variant glycosylation pattern, that produce antibodies. Antibody, as used herein, includes all forms of antibodies such as recombinant antibodies, humanized antibodies, chimeric antibodies, single chain antibodies, fusion antibodies, monoclonal antibodies, polyclonal antibodies and the like. The antibodies may be fragments. The antibodies may also be conjugated with drugs, toxins or therapeutic radioisotopes. Bispecific antibody fusion proteins can also be produced by the host cells of the present disclosure, including hybrid antibodies which bind to more than one antigen. Therefore, antibody encompasses naked antibodies and conjugated antibodies and antibody fragments, which may be monospecific or multispecific.

The antibodies can also have a variant glycosylation pattern, which may be characterized by a change in levels of at least two types of sugar molecules as compared to a corresponding wildtype antibody (ie. an antibody produced in an unmodified parental host cell). The sugar molecules may be directly attached to the glycoprotein (for example, N- or O-linked to the glycoprotein), or indirectly (for example, linked through other sugars that are N- or O-linked to the glycoprotein). Sugar chain structure variations, or variant glycosylation patterns, due to various sugar molecule content in such chains, play an important role in the effector function of glycoproteins. For example, variant glycosylation patterns, such as described above, of an antibody can increase the effector function of the antibody, such as increase the antibody-dependent cellular cytotoxicity (ADCC) activity of an antibody. The variant glycosylation pattern can be evidenced by a change in levels of at least two types of sugar molecules that are attached through an Fc region of the antibody, as compared to a corresponding antibody produced in an unmodified parental host cell.

In some embodiments, the antibodies exhibit an N-glycan that has the structural formula Glu-GlcNAC$_2$-Man$_4$ (+/−Fuc). In some embodiments, the antibody exhibits a glycosylation pattern that has the structural formula (I), in which a fucose moiety can optionally be linked to the first 4GlcNAc from the right:

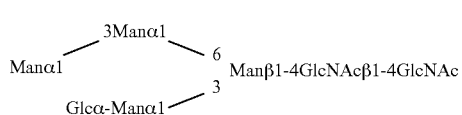

(I)

In some embodiments, the antibody exhibits a glycosylation pattern that has the structural formula (II), in which a fucose moiety can optionally be linked to the first 4GlcNAc from the right:

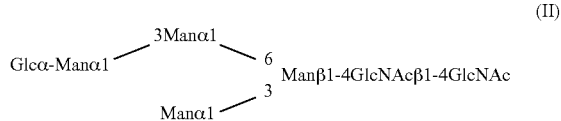

(II)

The structural formulae (I) and (II) encompass both scenarios, in which one or more fucose molecules are present or absent in the subject N-glycan. In some embodiments, fucose is present in the N-glycan. In other embodiments, fucose is absent in the N-glycan.

The antibodies produced can be from one of the five major classes of intact antibodies: e.g., IgA, IgD, IgE, IgG, and IgM. The antibody produced is a member of one of the subclasses selected from IgG1, IgG2, IgG3, IgG4, IaA, and IgA2.

The antibodies of the present disclosure may be monoclonal, which refers to an antibody from a population of substantially homogeneous antibodies, i e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones.

It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler et al, *Nature,* 256:495 (1975); Harlow et al, *Antibodies: A Laboratory Manual,* (Cold Spring Harbor Laboratory Press, 2nd ed. 1988); Hammerling et al., in: *Monoclonal Antibodies and T-Cell Hybridomas* 563-681, (Elsevier, N.Y, 1981)), recombinant DNA methods (see, e.g., U.S. Pat. No. 4,816,567), phage display technologies (see, e.g., Clackson et al., *Nature,* 352:624-628 (1991); Marks et al., *J. Mol. Biol.,* 222:581-597 (1991); Sidhu et al., *J. Mol. Biol.* 338(2):299-310 (2004); Lee et al., *J. Mol. Biol.* 340(5): 1073-1093 (2004); Fellouse, *Proc. Nat. Acad. Sci. USA* 101 (34):12467-12472 (2004); and Lee et al. *J. Immunol. Methods* 284(1-2):119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al, *Proc. Natl. Acad Sci. USA,* 90:2551 (1993); Jakobovits et al, *Nature,* 362:255-258 (1993); Bruggemann et al., *Year in Immuno.,* 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); and Lonberg and Huszar, *Intern. Rev. Immunol.,* 13: 65-93 (1995)).

Monoclonal antibodies herein include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

The host cells of the present disclosure can also be used to make hybridomas for the production of antibodies. A mouse or other appropriate host animal, (such as a hamster, goat, sheep, dog, horse, pig, rat, rabbit, dog, cat, or gerbil, amongst others) can be immunized as to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In one embodiment, myeloma cells are used that fuse efficiently, support stable high-level production of antibody by the selected antibody-producing cells, and are sensitive to a medium such as HAT medium. In some embodiments the myeloma cell lines are murine myeloma lines, (including, but not limited to, MOPC-21, MPC-11, SP-2 or X63-Ag8-653 cells), human myeloma cell lines (including, but not limited to, Karpas 707H, RPMI 8226, 8226 AR/NIP4-1, KM-2R, or U-266), or rat myeloma cell lines (including, but not limited to, YB2/3.0.Ag.20, YB2/0, Y3-Agl.2.3, IR983F).

Culture medium in which hybridoma cells are growing is assayed for production of monoclonal antibodies directed against the antigen. The binding specificity of monoclonal antibodies produced by hybridoma cells can be determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis. (see for example, Munson et al, *Anal. Biochem.* 107:220 (1980)).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones can then be suitably separated from the culture medium, ascites fluid, or serum by conventional antibody purification procedures such as, for example, protein A-Sepharose, hydroxylapatite chromatography, gel electrophoresis, dialysis, or affinity chromatography.

In some embodiments, the monoclonal antibody can be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

In an alternative embodiment, the cell population produced by the method of the present disclosure is used for the production of antibodies by recombinant DNA methods (U.S. Pat. No. 4,816,567, which is herein incorporated by reference in its entirety). The modified host cell exhibiting a variant glycosylation pattern can be produced from a parent cell line such as HeLa, HEK-293, NIH3T3, COS, CHO, NS0, PER.C6, K562, L1.2, JY, BHK, K562, 293F, 3T3, or Jurkat. In an alternative embodiment, modified host cell is derived from a parent cell line derived from a lymphocytic lineage cell line, such as a B cell line.

In one embodiment, messenger RNA (mRNA) coding for heavy or light chain is isolated from a suitable source, such as mature B cells or a hybridoma culture, is obtained by employing standard techniques of RNA isolation purification and optionally size based isolation. cDNAs corresponding to mRNAs coding for heavy or light chain are then produced and isolated using techniques known in the art, such as cDNA library construction, phage library construction and screening or RT-PCR using specific relevant primers. In some embodiments, the cDNA sequence may be one that is wholly or partially manufactured using known in vitro DNA manipulation techniques to produce a specific desired cDNA. The cDNA sequence can then be positioned in a vector which contains a promoter in reading frame with the gene and compatible with the low-modified host cell. Numerous plasmids that contain appropriate promoters, control sequences, ribosome binding sites, and transcription termination sites, and optionally convenient markers are known in the art, these include but are not limited to, vectors described in U.S. Pat. Nos. 4,663,283 and 4,456,748. In one embodiment, the cDNA coding for the light chain and that coding for the heavy chain may be inserted into separate expression plasmids. In an alternative embodiment, the cDNA coding for the light chain and that coding for the heavy chain may be inserted together in the same plasmid, so long as each is under suitable promoter and translation control.

The expression vectors constructed above can then be used to transform the modified host cells of the present disclosure. In one embodiment, the light and heavy chains may be transformed into separate modified host cell cultures, either of the same or of differing species. In an alternative embodiment, separate plasmids for light and heavy chain may be used to co-transform a single modified host cell culture. In another embodiment, a single expression plasmid containing both genes and capable of expressing the genes for both light and heavy chain may be transformed into a single modified host cell culture.

When heavy and light chains are coexpressed in the same host, the isolation procedure is designed so as to recover reconstituted antibody. This can be accomplished by conventional antibody purification procedures such as, for example, protein A-Sepharose, hydroxylapatite chromatography, gel electrophoresis, dialysis, or affinity chromatography.

In some embodiments, the monoclonal antibody purified by recombinant methods can be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The antibody produced by the recombinant method set forth above can be a humanized antibody, such as a human chimeric antibody, or a human complementary determining region (CDR) grafted antibody. Humanized forms of non-human (e.g., mouse, rat, hamster, goat, sheep, horse, cattle or rabbit) antibodies are chimeric antibodies that contain minimal sequence derived from non-human immunoglobulin. Humanized antibodies are typically human immunoglobulins (recipient antibody) in which residues from a hypervariable region of the recipient are replaced by residues from a hypervariable region of a non-human species (donor antibody) such as mouse, rat, goat, sheep, horse, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody comprises substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al, *Nature* 321:522-525 (1986); Riechmann et al, *Nature* 332: 323-329 (1988); and Presta, *Curr. Op. Struct. Biol.* 2:593-596 (1992).

The term variable refers to certain portions of the variable domains differing extensively in sequence among antibodies and are used in the binding and specificity of each particular antibody for its particular antigen. However, the variability is typically not evenly distributed throughout the variable domains of antibodies. It is usually concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al, *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term hypervariable region when used herein refers to the amino acid residues of an antibody which are responsible for antigen-binding. The hypervariable region generally comprises amino acid residues from a CDR (e.g residues 24-34 (L1), 50-56 (L2) and 89-97 (L3) in the light chain variable domain and 31-35 (H1), 50-65 (H2) and 95-102 (H3) in the heavy chain variable domain; Kabat et al, *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

A human chimeric antibody is an antibody which comprises an antibody heavy chain variable region (hereinafter referred to as "HV" or "VH", the heavy chain being "H chain") and an antibody light chain variable region (hereinafter referred to as "LV" or "VL", the light chain being "L chain"), both of an animal other than human, a human antibody heavy chain constant region (hereinafter also referred to as "CH") and a human antibody light chain constant region (hereinafter also referred to as "CL"). As the animal other than human, any animal such as mouse, rat, hamster, rabbit or the like can be used, so long as a hybridoma can be prepared there from.

A human chimeric antibody can be produced by obtaining cDNA's encoding heavy chain variable region (VH) and light chain variable region (VL) from a monoclonal antibody-producing hybridoma, inserting them into an expression vector for a host cell having genes encoding human antibody CH and human antibody CL to thereby construct a human chimeric antibody expression vector, and then introducing the vector into a low-fucosylation cell to express the antibody.

In regards to the heavy chain constant region (CH) of a human chimeric antibody, any CH can be used, so long as it is in the human immunoglobulin (hereinafter referred to as "hIg") class. In some embodiments, the CH belongs to the hIgG class or one of the subclasses belonging to the hIgG class, such as hIgG1, hIgG2, hIgG3 and hIgG4. Likewise, in regards to the light chain constant region (CL) of human chimeric antibody, any CL can be used, so long as it belongs to the hIg class. In some embodiments, the light chain constant region (CL) of human chimeric antibody belongs to the keppa class or lambda class.

A human CDR-grafted antibody can be produced by constructing cDNA's encoding variable regions in which CDR's of VH and VL of an antibody derived from an animal other than human are grafted into CDR's of VH and VL of a human antibody, inserting them into an expression vector for host cell having genes encoding human antibody CH and human antibody CL to thereby construct a human CDR-grafted antibody expression vector, and then introducing the expression vector into a modified host cell of the present disclosure to express the human CDR-grafted antibody.

Preferably the antibody of the present invention essentially retains the ability to bind antigen compared to the parental antibody. In some embodiments, the antibody of the present invention exhibits higher binding affinity to an antigen, for example, at least 1.1, 1.2, 1.3. 1.4, 1.5, 2, 3, 4, or 5 fold higher than a parental antibody. In other embodiments, the antibody of the present invention exhibits lower binding affinity to an antigen, for example, no less than 5%, 10%, 20%, 30%, 40%, or 50% of the binding affinity of a parental antibody to the antigen. The binding capability of the antibody of the present invention may be determined using techniques such as fluorescence activated cell sorting (FACS) analysis or radioimmunoprecipitation (RIA), for example.

The antibody with variant glycosylation patterns and/or produced by modified host cells of the present disclosure may bind an antigen such as a cancer antigen. The antigen may be selected from the group consisting of The glycoprotein of claim 9 wherein the cancer antigen is selected from the group consisting of HER2, Immunoglobulin epsilon Fc receptor II, Alk-1, CD20, EGF receptor, VEGF receptor, FGF receptor, NGF receptor, PDGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha and beta integrins.

In some embodiments, humanized HER2 antibodies are produced in a modified host cell that exhibits a variant glycosylation pattern. Humanized HER2 antibodies include, but are not limited to, huMAb4D5-1, huMAb4D5-2, huMAb4D5-3, huMAb4D5-4, huMAb4D5-5, huMAb4D5-6, huMAb4D5-7 and huMAb4D5-8 or trastuzumab (HERCEPTIN®) as described in Table 3 of U.S. Pat. No. 5,821,337 expressly incorporated herein by reference; humanized 520C9 (WO93/21319); and humanized 2C4 antibodies such as pertuzumab. Such humanized antibodies produced by the modified host cells of the present disclosure can themselves have variant glycosylation patterns, as compared to the antibodies if produced in an unmodified parental cell.

In another embodiment, a vector encoding a HER inhibitor such as an EGFR, HER2, HER3 or HER4 antibody is introduced into the modified host cell line of the present disclosure. HER inhibitor antibodies include trastuzumab, pertuzumab, cetuximab, ABX-EGF, ABX0303, EMD7200, C11033, IMC-11F8, and IMC-11F5. The HER inhibitor produced in a modified host cell can exhibit a variant glycosylation pattern, such as a change in levels of at least 2 sugar molecules as described above, in comparison to a HER inhibitor produced in an unmodified parental host cell.

The HER antibodies or inhibitors of the present disclosure can be used to treat cancer cells which display HER expression, amplification, or activation. HER activation refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

HER inhibitors include dimerization inhibitors which are agents that inhibit formation of a HER dimer. The HER dimerization inhibitor can be an antibody, for example an antibody which binds to HER2 at the heterodimeric binding site thereof. The antibody may be those described herein, such as those exhibiting a variant glycosylation pattern. A dimerization inhibitor contemplated herein is pertuzumab or monoclonal antibody 2C4 (MAb 2C4). Other examples of HER dimerization inhibitors include antibodies which bind to EGFR and inhibit dimerization thereof with one or more other HER receptors (for example EGFR monoclonal antibody 806, MAb 806, which binds to activated or untethered EGFR; see Johns et al, *J. Biol. Chem.* 279(29):30375-30384 (2004)); antibodies which bind to HER3 and inhibit dimerization thereof with one or more other HER receptors; antibodies which bind to HER4 and inhibit dimerization thereof with one or more other HER receptors; peptide dimerization inhibitors. See, U.S. Pat. No. 6,417,168 hereby incorporated by reference in its entirety. Antibodies that inhibit HER dimerization, such as pertuzumab, may be used to treat cancer cells, which does not over express or amplify HER2 receptor.

The modified host cell can also be used to produce a recombinant protein other than a full-length antibody, with a variant glycosylation pattern. A vector encoding a recombinant protein (such as a plasmid, or virus) using techniques standard in the art can be introduced into a modified host cell and the recombinant protein may be any protein of interest, including hormones, cytokines and antibody fragments, such as Fv, Fab, scFV or diabody fragments.

The Fv fragment is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

Single-chain Fv (scFv) antibody fragments comprise the VH and VL domains of antibody, wherein these domains are present in a single polypeptide chain. In some embodiments the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol 113, Rosenburg and Moore eds., Springer-Verlag, New York, pp. 269-315 (1994). HER2 antibody scFv fragments are described in WO93/16185; U.S. Pat. No. 5,571,894; and U.S. Pat. No. 5,587,458, which are hereby incorporated by reference in their entirety, and may be produced by the modified host cells of the present disclosure.

The term diabodies refers to small antibody fragments with two antigen-binding sites, which fragments comprise a VH domain connected to a VL domain in the same polypeptide chain (VH-VL). By using a linker that is too short to allow pairing between the two domains on the same chain, the domains are forced to pair with the complementary domains of another chain and create two antigen-binding sites. Diabodies are described more fully in, EP 404,097; WO 93/11161; and Hollinger et al, *Proc. Natl. Acad. Sci USA*, 90:6444-6448 (1993), which are hereby incorporated by reference in their entirety.

In some embodiments, the antibody is an inhibitory antibody. Inhibitory antibody may inhibit one or more biological activities of the antigen to which the antibody binds. For example, an inhibitory antibody can downregulate signal transduction of the corresponding antigen by inhibiting the activity of the antigen or inhibit expression of the antigen. In some embodiments, the antibody is a neutralizing antibody. A neutralizing antibody reduces or abolishes some biological activity of a soluble antigen or of a living microorganism, such as an infectious agent. Neutralizing antibodies may compete with the natural ligand or receptor for its antigen. In some embodiments, the antibody is a stimulatory or activating antibody. A stimulatory or activating antibody may be an agonist antibody which may activate signal transduction of the corresponding antigen upon binding of the antigen thereby activating or upregulating the activity of the antigen, or upregulate the expression of the antigen to which the antibody binds.

Antibodies that may comprise the N-glycan of the invention include, but are not limited to, abciximab (ReoPro®), adalimumab (Humira®), alemtuzumab (Campath®), basiliximab (Simulect®), bevacizumab (Avastin®), cetuximab (Erbitux®), daclizumab (Zenapax®), dacetuzumab, eculizumab (Soliris®), efalizumab (Raptiva®), Edrecolomab (Panorex®), epratuzumab, ibritumomab (Zevalin®), tiuxetan, infliximab (Remicade®), muromonab-CD3 (OKT3), natalizumab (Tysabri®), omalizumab (Xolair®), palivizumab (Synagis®), panitumumab (Vectibix®), ranibizumab (Lucentis®), gemtuzumab ozogamicin (Mylotarg®), oregovomab (OvaRex®), rituximab (Rituxan®), tositumomab (Bexxar®), trastuzumab (Herceptin®), MetMAb, ocrelizumab, pertuzumab, Raptiva® (efalizumab), hu M195Mab, MDX-210, BEC2, anti-Abeta, anti-CD4, anti-IL-13, anti-oxLDL, trastuzumab-DM1, apomab, rhuMAb beta7, rhuMAb IFNalpha, GA101, anti-OX40L, ipilimumab, Valortim, ustekinumab, golimumab, ofatumumab, zalutumumab, tremelimumab, motavizumab, mitumomab, ecromeximab, ABX-EGF, MDX010, XTL 002, H11 SCFV, 4B5, XTL001, MDX-070, TNX-901, IDEC-114, and any antibody fragments specific for antigens including but not limited to complement C5, CBL, CD147, gp 120, VLA4, CD11a, CD18, VEGF, CD40L, anti-Id, ICAM1, CD2, EGFR, TGF-β2, TNF-α, TNF receptor, E-selectin, FactII, Her2/neu, F gp, CD11/18, CD14, CD80, ICAM3, CD4, CD23, β2-integrin, α4β7, CD52, CD22, OX40L, IL-5 receptor, GM-CSF receptor, GM-CSF, HLA-DR, oxLDL, CD64 (FcR), TCR α β, CD3, Hep B, CD125, DR5, EpCAM, gpIIbIIIa, IgE, beta 7 integrin, CD20, IL1β, IL-2, IL-4, IL-5, IL-6, IL-8, IL-9, IL-10, IL-13, IL-12/IL-23, IL-15, IFN-α, VEGFR-1, platelet-derived growth factor receptor α (PDGFRα), vascular adhesion protein 1 (VAP1), connective tissue growth factor (CTGF), Apo2/TRAIL, CD25, CD33, HLA, F gp, IgE, CTLA-4, IP-10, anti-*C. difficile* Toxin A and Toxin B, *B. anthracis* PA, respiratory syncytial virus (RSV), mannose receptor/hCGβ, integrin receptors, PD1, PDL-1, CD19, CD70, and VNR integrin.

Antibodies comprising the N-glycan of the present invention have a good half-life comparable to that of native antibodies or antibodies produced by unmodified host cells. Antibody half-life typically refers to a measure of the mean survival time of antibody molecules following their formation, usually expressed as the time required to eliminate 50% of a known quantity of immunoglobulin from the animal body. Half-life varies from one immunoglobulin class to another, and also can vary from species to species. In some embodiments, the antibody expressing the subject N-glycan produced by CHO-1E5 cells has a comparable terminal half-life in vivo as that of an antibody produced by the parental CHO cells. In some embodiment, the subject antibodies have a terminal half-life in a test animal for at least 4, 8, 12, 24, 48, 72 hours, or even longer. Terminal half-life can be assessed by quantitating the amount of antibodies remained in the subject's biological fluid (e.g., blood or serum) after the initial administration and over a course of defined period of time. Initial administration can be carried out intravenously, subcutaneously or any other suitable route known in the art or disclosed herein.

In some embodiments, the subject antibodies comprising the N-glycan of the present invention having enhanced ADCC activity but do not elicit substantially higher immunogenicity as compared to a parental antibody produced by an unmodified host cell or antibodies lacking the unique N-glycan of the present invention. Immunogenicity typically refers to the ability of a particular substance, such as an antigen or epitope, to provoke an immune response, humoral and/or cell-mediated immune responses. Proteins and polysaccharides can be immunogenic. In one embodiment, the antibody comprising the subject N-glycan exhibits comparable immunogenicity or the lack thereof in vivo as that of an antibody produced by the parental CHO cells. Methods for assessing immunogenicity or the lack thereof are known in the art. For example, a conventional approach is to measure its capacity to induce antibody responses, such as serum antibody titer. As described in Example 14 and FIG. 29, the in vivo immunogenicity is measured by antibody titer against the subject antibodies of the present invention. Specifically in one example, the subject ET101 antibody produced by wild type CHO cells or ET101 produced by CHO-1E5 cells are separately injected into two groups of non-human primates. Serum IgM production in response to the injected subject antibody is measured by ELISA. The serum IgM titer reflects the level of immunogenicity induced by the subject antibodies in vivo. Antibody titers can be measured in the range of 1:1-1:1,000,000 dilutions of the serum. In some embodiments, the IgM titer against the subject antibodies produced by CHO cells or CHO-1E5 cells is in the range of no more than 100,000 ng/ml of serum, no more than 10,000 ng/ml, no more than 1,000 ng/ml, no more than 100 ng/ml or even no more than 10 ng/ml. In some embodiments, the IgM titer is about 0.1 optical densities (OD) at 405 nm with a 1:100 serum dilution, which corresponds to about 500 ng-1000 ng/IgM/ml of serum. As shown in FIG. 29, the IgM titer does not increase over more than 7 days, 14 days, 20 days, 24 days, 30 days, 35 days or even longer post antibody injection.

Assays suitable for measuring IgM or other antibody isotype titers for assessing the immunogenicity of the subject antibodies include but are not limited to direct binding assays, bridging assays, capture (sandwich) assays and competitive immunoassays using radioligand, enzymatic, fluorescent, chemiluminescent or electrochemical luminescence detection systems. One alternative method for assessing in vivo immunogenicity of a target antibody is a magnetic bead based immunoprecipitation method followed by quantitative liquid chromatography-mass spectrometry (LC/MS) to determine anti-drug antibodies (ADA) in human and cynomolgus monkey serum in the presence of high circulating concentrations of the target antibody, i.e. the ET101-CHO-1E5 antibody.

Available ADA binding sites are saturated by the addition of excess target antibody followed by magnetic bead based protein G isolation of IgG antibodies and their bound antigens before elution and digestion. Peptides of the target antibodies are then quantified by LC/MS using stable isotope labeled standards inferring the presence of total ADA. This approach complements established methodologies for the assessment of immunogenicity response (Hendrik N. et al. Analytical chemistry, 2008 vol. 80, n° 18, pp. 6907-6914).

Unwanted immunogenicity induced by target antibodies can comprise humoral and cellular immune responses. Where desired, one can measure both humoral and cellular immune responses. In most cases, development of a mature IgG response implies underlying antigen specific helper T-cell involvement. Examples of assays for detecting/assessing cell-mediated responses upon administration of the subject antibodies of the present invention include but are not limited to T-cell stimulation/proliferation assays, cytokine (e.g. IL2, IL4, IFN-gamma) production/release methods, measurement of receptor phosphorylation status, or modulation of one or more T cell or B cell intracellular markers. These involve the use of T-cell preparations sometimes co-cultured with preparations of other cell types, e.g. dendritic cells. Elispot and flow cytometry procedures are commonly used for these assays. Memory B-cell (and sometimes memory T-cell) assays can provide useful information regarding the nature of the immune response and may contribute to prediction of development of immunogenicity. Studies using peptides or full-length target protein, e.g. ET101-CHO-1E5 antibody (depending on the assays and purpose of the assays) and Elispot methodologies can be used (See "GUIDELINE ON IMMUNOGENICITY ASSESSMENT OF BIOTECHNOLOGY-DERIVED THERAPEUTIC PROTEINS", 2007).

Fc Receptor (FcR) Binding

In one aspect, the present invention provides an antibody produced by a modified host cell, wherein the antibody has increased binding affinity to an Fc receptor, FcγIIIa, and/or decreased binding affinity to another Fc receptor, FcγIIb, as compared to a corresponding antibody produced by an unmodified host cell, thereby enhancing antibody-dependent cell-mediated cytotoxicity against effector cells expressing such Fc receptors. In another aspect, the present invention provides a modified host cell characterized in its ability to produce a modified antibody, wherein the antibody exhibits increased binding affinity to FcγIIIa, and/or decreased binding affinity to FcγIIb, as compared to a corresponding antibody produced by an unmodified host cell.

The interaction of antibodies and antibody-antigen complexes with cells of the immune system effects a variety of responses, including antibody-dependent cell-mediated cytotoxicity (ADCC) (reviewed in Daeron, Annu. Rev. Immunol. 15:203-234 (1997); Ward and Ghetie, Therapeutic Immunol. 2:77-94 (1995); as well as Ravetch and Kinet, Annu. Rev. Immunol. 9:457-492 (1991)).

The term "Fc receptor" or "FcR" is used to describe a receptor that binds to the Fc region of an antibody. An exemplary FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino add sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future are encompassed by the term "FcR" herein. The term also includes the neonatal receptor, FcRn, which is responsible for the transfer of material IgGs to the fetus (Guyer et al., J. Immunol. 117:587 (1976) and Kim et al., J. Immunol. 24:249 (1994)).

Several antibody effector functions are mediated by Fc receptors (FcRs), which bind the Fc region of an antibody. FcRs are defined by their specificity for immunoglobulin isotypes; Fc receptors for IgG antibodies are referred to as Fc γR, for IgE as Fc εR, for IgA as Fc αR and so on. Three subclasses of Fc γR have been identified: Fc γRI (CD64), Fc γRII (CD32) and Fc γRIII (CD 16). Because each Fc γR subclass is encoded by two or three genes, and alternative RNA splicing leads to multiple transcripts, a broad diversity in Fc γR isoforms exists. The three genes encoding the Fc γRI subclass (Fc γRIA, Fc γRIB and Fc γRIC) are clustered in region 1q21.1 of the long arm of chromosome 1; the genes encoding Fc γRII isoforms (Fc γRIIA, Fc γRIB and Fc γRIIC) and the two genes encoding Fc γRIII (Fc γRIIIA and Fc γRIIIB) are all clustered in region 1q22. These different FcR subtypes are expressed on different cell types (reviewed in Ravetch and Kinet, Annu. Rev. Immunol. 9:457-492 (1991)). For example, in humans, Fc γRIIIB is found only on neutrophils, whereas Fc γRIIIA is found on macrophages, monocytes, natural killer (NK) cells, and a subpopulation of T-cells. Notably, Fc γRIIIA is the only FcR present on NK cells, one of the cell types implicated in ADCC. Fc γ RIIIA is an activating transmembrane receptor expressed on macrophages and NK cells. It is also a neutrophil opsonin receptor (Ravetch, J. and L. Lanier, 2000, Science 290:84). Fcγ RIA is transmembrane protein with three extracellular Ig-like domains. Fcγ RI is expressed constitutively on monocytes and macrophages and can be induced on neutrophils and eosinophils. FcR expression on hematopoietic cells is reviewed in Ravetch and Kinet, *Annu. Rev. Immunol* 9:457-92 (1991), which is herein incorporated by reference in its entirety.

In one embodiment, the present invention provides an antibody with altered FcR binding affinity. An antibody with "altered" FcR binding affinity is one which has either enhanced or diminished FcR binding activity and/or ADCC activity compared to a parent antibody or to an antibody comprising a native sequence Fc region. The antibody of the present invention which "displays increased binding" to an FcR binds at least one FcR with better affinity than the parent antibody. The antibody of the present invention which "displays decreased binding" to an FcR, binds at least one FcR with lower affinity than a parent antibody. Such variants which display decreased binding to an FcR may possess little or no appreciable binding to an FcR, e.g., 0-20% binding to the FcR compared to a native sequence IgG Fc region.

The antibody of the present invention which binds an FcR with higher affinity than a parent antibody is one which binds any one or more of the above identified FcRs with substantially higher binding affinity than the parent antibody, when the antibody having the unique N-linked glycan and the parent antibody are applied in comparable amounts. For example, the antibody with improved FcR binding affinity may display from about 1.1 fold to about 10,000 fold, for example, 1.15 fold, 1.5, 2, 3, 4, 5, 6, 7, 8, 9, 10, 15, 20, 30, 40, 50, 60, 70, 80, 90, 100, 500, 1,000, 10,000 fold or more in FcR binding affinity as compared to the parent antibody, where FcR binding affinity is determined, for example, as disclosed in the Examples herein.

The phrase "low affinity receptor" denotes a receptor that has a weak binding affinity for a ligand of interest, e.g. having a binding constant of about 50 nM or worse affinity. Exemplary low affinity receptors include but are not limited to Fc γRIIIa 158 F/F and Fc γRIIIa 158 F/V.

In some embodiments, the antibody produced by CHO 1E5 cells displays increased binding to Fc γRIIIa, an activating Fc γR, and may further display decreased binding to Fc γRIIb, an inhibitory Fc γR.

Antibody-Dependent Cellular Cytotoxicity (ADCC) Activity

The modified host cells of the present disclosure can be used to produce antibodies or functional antibody fragments as described above. The antibodies or functional antibody fragments produced by these cells can also exhibit a variant glycosylation as described herein, such as a change in levels of at least 2 sugar molecules as compared to the corresponding antibodies or functional antibody fragments produced in an unmodified parental host cells. Furthermore, these antibodies or fragments with a variant glycosylation pattern can have improved antibody-dependent cellular cytotoxicity (ADCC) or other antibody effector functions in comparison to the corresponding antibodies or antibody fragments produced in unmodified parental host cells. Alternatively, the antibody or antibody fragments with variant glycosylation patterns exhibits increased ADCC as compared to a corresponding antibody lacking said variant glycosylation pattern. The antibody or antibody fragments with improved or increased ADCC activity may also have a variant glycosylation pattern.

For example, a parental CHO cell line can be modified to yield a modified CHO cell line with a variant glycosylation pattern. The modified CHO cell line can then produce an antibody having higher ADCC activity than that of an antibody produced by the parental CHO cell. The antibody produced by modified CHO cell line can also have a variant glycosylation pattern.

"Antibody-dependent cell-mediated cytotoxicity" (ADCC) refers to a cell-mediated reaction in which effector cells that express FcRs (e.g. Natural Killer (NK) cells, neutrophils, and macrophages) recognize bound antibody on a target cell and subsequently cause lysis of the target cell. The primary cells for mediating ADCC comprise NK cells, monocytes, and macrophages. NK cells typically express FcγRIII predominantly, whereas monocytes express Fc γRI, Fc γRII and Fc γRIII. FcR expression on hematopoietic cells is summarized in Ravetch and Kinet, *Annu. Rev. Immunol* 9:457-92 (1991).

"Effector cells" are leukocytes which express one or more FcRs and perform effector function(s). Preferably, the cells express at least Fc γRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein, or may propagate in vitro using known methods in the art.

In one embodiment, the antibody of the present invention mediates antibody-dependent cell-mediated cytotoxicity (ADCC) in the presence of human effector cells more effectively than a corresponding antibody produced by parental host cells, when the subject antibodies are applied in comparable amounts. Generally, ADCC activity can be ascertained using assays disclosed herein, but other assays or methods for determining ADCC activity, e.g. in an animal model etc, are contemplated. The antibody of the present invention is from about 1.1 fold to about 10,000 fold, e.g., 1.15, 1.5, 2, 3, 4, 5, 6, 7, 8, 9, 10, 15, 20, 30, 40, 50, 60, 70, 80, 90, 100, 500, 1,000, 10,000 fold or more, more effective at mediating ADCC than the parent antibody, e.g. in the in vitro assay disclosed herein.

In some embodiments, the antibody of the present invention having the unique N-linked glycan exhibits increased ADCC against effector cells expressing Fc γRIIIa of different genotypes, as compared with the parental antibody. In one example, the antibody having the unique N-linked glycan exhibits increased ADCC, as compared to the parental antibody, against effector cells expressing Fc γRIIIa 158V/V (when the amino acid 158 is valine at the two alleles), which has high affinity to Fc fragment of IgG. In another example, the antibody having the unique N-linked glycan exhibits increased ADCC, as compared to the parental antibody, against effector cells expressing Fc γRIII 158F/F or Fc γRIII 158F/V (when the amino acid 158 is phenylalanine at both or one of the alleles), which has low affinity to Fc fragment of IgG. It is known that the genomic polymorphism corresponding to the phenotype of valine (V) or phenylalanine (F) at amino acid 158 on the Fc γRIIIa greatly influences the affinity of IgG1 to the Fc γR (Koene H R, et al. *Blood* 90:1109-1114, 1997). In addition, immune effector cells bearing the Fc γRIIIa V allele mediate ADCC of anti-HER-2/neu IgG 1 variants better than cells bearing the F allele (Shields R L, et al. *J Biol Chem* 9:6591-6604, 2001). The anti-HER-2/neu monoclonal antibody trastuzumab has been shown to engage both activatory (fragment C receptor (Fc γRIIIa; Fc γRIIa) and inhibitory (Fc γRIIb) antibody receptors and Fc γR polymorphisms have been identified that may affect the antibody-dependent cell-mediated cytotoxicity (ADCC) of natural-killer cells/monocytes. Studies have investigated whether Fc γR polymorphisms are associated with clinical outcome of patients with breast cancer who received trastuzumab. It was found that Fc γRIIIa-158 V/V genotype was significantly correlated with objective response rate (ORR) and progression-free survival (PFS). Also, there was trend significance in ORR and PFS for the Fc γRIIa-131 H/H genotype. The combination of the two favorable genotypes (VV and/or H/H) was independently associated with better ORR and PFS compared with the other combinations. The ADCC analysis showed that V/V and/or H/H PBMCs had a significantly higher trastuzumab-mediated cytotoxicity than PBMCs harboring different genotypes. The PFS estimate of patients with Fc γRIIIa 158 V/V was significantly longer than for patients with 158 V/F, 158 F/F, or F carriers (V/F+F/F combined) (Antonino Musolino, et al. *Journal of Clinical Oncology*, Volume 26, No. 11, Apr. 10 2008). Thus, the antibody of the present invention, having increased ADCC activity against cells expressing Fc γRIII 158V/V and cells expressing Fc γRIII 158F/F, as compared to an unmodified antibody, can be very useful in enhancing the clinical outcome of patients with various disorders including cancer treated with antibody-based therapy.

ADCC activity as used herein also encompasses an activity to injure a cell, for example, a tumor cell, by activating an effector cell via the binding of the Fc region of an antibody to an Fc receptor existing on the surface of an effector cell such as a killer cell, a natural killer cell, an activated macrophage or the like (*Monoclonal Antibodies: Principles and Applications*, Wiley-Liss, Inc., Chapter 2.1 (1995)). For example, the ADCC activity can be a cytotoxic activity in which an antibody bound to a cell surface antigen on a tumor cell in the living body activates an effector cell that express Fc receptors (FcRs) (e.g. peripheral blood mononuclear cells (PBMC), monocytes, cytotoxic T cells Natural Killer (NK) cells, neutrophils, and macrophages), leading to recognition of the bound antibody on a target cell and subsequently cause lysis of the target cell. (*Monoclonal Antibodies: Principles and Applications*, Wiley-Liss, Inc., Chapter 2.1 (1995)). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo e.g., in an animal model such as that disclosed in Clynes et al, *Proc. Natl. Acad. Sci. USA* 95:652-656 (1998).

Antibody effector functions also include, but are not limited to, C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Complement dependent cytotoxicity (CDC) refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g as described in Gazzano-Santoro et al, *J. Immunol. Methods* 202:163 (1996), may be performed.

The antibody of the present invention may be subjected to one or more assays to evaluate any change in biological activity compared to the parental antibody.

The ability of the antibody of the present invention to bind an FcR may be evaluated. Where the FcR is a high affinity Fc receptor, such as Fc γRIIIA-158 V/V, binding can be measured by titrating the subject antibody and measuring bound antibody using an antibody which specifically binds to the antibody of the present invention in a standard ELISA format.

To assess ADCC activity of the antibody of the present invention, an in vitro ADCC assay, such as that described in Example 12 may be performed using varying effector:target ratios. Useful "effector cells" for such assays include peripheral blood mononuclear cells (PBMC) and natural killer (NK) cells. Alternatively, or additionally, ADCC activity of the antibody of the present invention may be assessed in vivo, e.g., in an animal model such as that disclosed in Clynes et al. PNAS (USA) 95:652-656 (1998).

Formulation, Administration and Treatment

An antibody of the present invention which has increased ADCC activity can be useful in the prevention and treatment of various disorders.

A "disorder" as used herein refers to any condition that would benefit from treatment with the antibody produced by the modified host cells of the present invention. This includes chronic and acute disorders or diseases including those pathological conditions which predispose the mammal to the disorder in question. Examples of disorders include but are not limited to cancer, allergies, cardiovascular diseases, inflammatory diseases, metabolic diseases, neurological diseases, viral infections and/or bacterial infections. In one embodiment, the disorder is cancer. Examples of cancer include, but are not limited to, carcinoma, lymphoma, blastoma, sarcoma, and leukemia. More particular examples of such cancers include but are not limited to adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's Disease, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine cancer (e.g. uterine sarcoma), vaginal cancer, vulvar cancer, and Waldenstrom's macroglobulinemia. One example of a cancer can be a "HER2-expressing cancer", which comprises cells having HER2 receptor protein (Semba et al., PNAS (USA) 82:6497-6501 (1985) and Yamamoto et al. Nature 319:230-234 (1986) (Genebank accession number X03363)) present on their cell surface, such that an anti-HER2 antibody is able to bind to the cancer.

For example, in cancer, such as a malignant tumor, an antibody having high ADCC activity can treat cancers by injuring proliferation of the cancer cells through its cytotoxic effect. Antitumor effect of the antibody on various tumor cells can be analyzed by methods described above. For example, in vitro tests such as, but not limited to, CDC activity measuring method, ADCC activity measuring methods and the like, and in vivo tests, such as an antitumor experiment using a tumor system in an experimental animal such as a mouse or the like may be performed. CDC activity and ADCC activity measurements and antitumor experiments can be carried out in accordance with the methods as described in Shitara et al, *Cancer Immunology Immunotherapy*, 36, 373-380 (1993); Nakamura et al, *Cancer Research*, 54, 1511-1516 (1994) and the like.

For treatment of allergies, where an allergic reaction is typically induced by the release of a mediator molecule from immune cells, the allergic reaction can be inhibited by removing the immune cells using an antibody having high ADCC activity. Cardiovascular diseases can be prevented and treated by inhibiting proliferation of arterial cells in re-stricture after the treatment, by using an antibody having high ADCC activity. Various diseases including viral or bacterial infections can be prevented and treated by inhibiting proliferation of the virus- or bacterium-infected cells using an antibody having high ADCC activity.

In some embodiments, the antibody exhibiting the glycosylation pattern Glu-GlcNAC$_2$-Man$_4$ (+/−Fuc) has increased ADCC activity against various cancer cells including but not limited to breast cancer cells, ovarian cancer cells, and lung cancer cells, as compared to a corresponding antibody produced by the unmodified parental host cell. In some embodiments, the antibody exhibiting the glycosylation pattern Glu-GlcNAC$_2$-Man$_4$ (+/−Fuc) has increased binding affinity to Fc γRIIIA receptor as compared to a corresponding antibody produced by the unmodified parental host cell. The antibody exhibiting Glu-GlcNAC$_2$-Man$_4$ (+/−Fuc) has similar in vivo pharmacokinetic characteristics as a corresponding antibody produced by the unmodified parental host cell.

The subject antibody having an N-linked glycosylation pattern disclosed herein exhibits a pharmacokinetic profile that is comparable to that of antibody produced by wild-type parental host cells. The pharmacokinetic profile describes parameters of how a drug is absorbed, distributed, metabolized, and eliminated by the body. Pharmacokinetics is a study of the action of drugs in the body over a period of time, including the processes of absorption, distribution, localization in tissues, biotransformation, and excretion. Pharmacokinetic parameters include but are not limited to route of drug administration, first order kinetics including volume of distribution (Vd), clearance (Cl) of a drug, elimination constant (kel), elimination half life (t½), serum concentration, bioavailability, in vivo solubility, zero order elimination, dosing regimen, hepatic drug clearance, drug distribution, protein binding, and degree of ionization. Drug pharmacokinetics determines the onset, duration, and intensity of a drug's effect.

Therapeutic formulations of the antibody of the present invention are prepared for storage by mixing the antibody having the desired degree of purity with optional physiologically acceptable-carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, Pluronics™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes. Sustained-release preparations may be prepared. Suitable examples of sustained-release preparations include semipermeable matrices of solid hydrophobic polymers containing the antibody of the present invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

It is contemplated that the antibody produced by 1E5 cells of the present invention may be used to treat a mammal e.g. a patient suffering from, or predisposed to, a disease or disorder, who could benefit from administration of the antibody. The conditions which can be treated with the antibody of the present invention are many and include cancer (e.g. where the antibody of the present invention binds the HER2 receptor, CD20 or vascular endothelial growth factor (VEGF)); allergic conditions such as asthma (with an anti-IgE antibody); and LFA-1-mediated disorders (e.g. where the antibody of the present invention is an, anti-LFA-1 or anti-ICAM-1 antibody) etc.

Where the antibody binds the HER2 receptor, the disorder preferably is HER2-expressing cancer, e.g. a benign or malignant tumor characterized by overexpression of the HER2 receptor. Such cancers include, but are not limited to, breast cancer, squamous cell cancer, small-cell lung cancer, non-small cell lung cancer, gastrointestinal cancer, pancreatic cancer, glioblastoma, cervical cancer, ovarian cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. According to the teachings herein, one may prepare a polypeptide with a variant Fc region which has improved, or diminished, ADCC activity. Such molecules will find applications in the treatment of different disorders.

For example, the antibody with improved ADCC activity may be employed in the treatment of diseases or disorders where destruction or elimination of tissue or foreign microorganisms is desired. For example, the antibody of the present invention may be used to treat cancer; inflammatory disorders; infections (e.g. bacterial, viral, fungal or yeast infections); and other conditions (such as goiter) where removal of tissue is desired, etc.

Where the antibody has diminished ADCC activity, such antibodies may be used to treat diseases or disorders where an Fc region-containing polypeptide with long halt-life is desired, but the antibody of the present invention preferably does not have undesirable effector function(s). For example, the Fc region-containing polypeptide may be an anti-tissue factor (TF) antibody; anti-IgE antibody; and anti-integrin antibody (e.g. an anti-α4-β7 antibody). The desired mechanism of action of such Fc region-containing polypeptides may be to block ligand-receptor binding pairs. Moreover, the Fc-region containing polypeptide with diminished ADCC activity may be an agonist antibody.

The antibody of the present invention is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody of the present invention is suitably administered by pulse infusion, particularly with declining doses of the antibody of the present invention. Preferably the dosing is given by injections, most preferably intravenous or subcutaneous injections, depending in part on whether the administration is brief or chronic.

For the prevention or treatment of disease, the appropriate dosage of the antibody of the present invention will depend on the type of disease to be treated, the severity and course of the disease, whether the antibody of the present invention is administered for preventive or therapeutic purposes, previous therapy, the patient clinical history and response to the antibody of the present invention, and the discretion of the attending physician. The antibody of the present invention is suitably administered to the patient at one time or over a series of treatments.

Depending on the type and severity of the disease, about 1 μg/kg to 15 mg/kg (e.g., 0.1-20 mg/kg) of the antibody of the present invention is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of the antibody present in the formulation, the type of disorder or treatment, and other factors discussed above. These are generally used in the same dosages and with administration routes as used hereinbefore or about from 1 to 99% of the heretofore employed dosages.

In some embodiments, the antibody and/or host cell of the present invention may be used to prevent or treat a disorder in a mammal. The mammal selected from the group consisting of a human, non-human primate, rodent, dog, cat, horse, cow, pig, sheep, rabbit, guinea pig, or goat.

Fermentation and Method of Production

In one aspect, the present invention provides a method of producing a modified glycoprotein comprising providing a heterologous polynucleotide sequence that encodes the modified glycoprotein and causing the modified glycoprotein to be expressed in a host cell disclosed herein. In some embodiments, the present invention encompasses a culture medium comprising a host cell disclosed herein. In other embodiments, the present invention further includes a culture fermentor comprising a plurality of host cells of the invention in a culture medium.

Fermentation is a standard process well known in the relevant art for the breakdown and re-assembly of biochemicals and biological molecules including proteins for industry, often in aerobic growth conditions. A fermentor or a bioreactor as used herein refers to an apparatus that maintains optimal conditions for the growth of microorganisms, e.g. host cells of the present invention, used in large-scale or small-scale fermentation and in the commercial production of biological macromolecules including but not limited to glycoproteins, for example, antibodies.

The production of recombinant monoclonal antibodies involves technologies, referred to as "repertoire cloning" or "phage display/yeast display". Recombinant antibody engineering involves the use of viruses or yeast to create antibodies, rather than mice. These techniques rely on rapid cloning of immunoglobulin gene segments to create libraries of antibodies with slightly different amino acid sequences from which antibodies with desired specificities can be selected. These techniques can be used to enhance the specificity with which antibodies recognize antigens, their stability in various environmental conditions, their therapeutic efficacy, and their detectability in diagnostic applications. Fermentation chambers have been used to produce these antibodies on a large scale. In some embodiments, the antibody expressing the unique N-glycan of the present invention can be produced in a culture fermentor.

EXAMPLES

Example 1

Selection of Optimal Concentration of Killing Agent

To acquire a cell population with a variant glycosylation pattern, chemicals were applied to cells to cause random genomic mutations that would also select cells with a variant glycosylation pattern. Chemical-induced random mutagenesis can lead to mutations of genes that control or regulate sugar biogenesis and protein glycosylation processes, such as fucosylation. Stable clones with low fucosylation activity after mutagenesis can be enriched and isolated by targeting cells with LCA, which binds to fucosylation proteins on the cell surface, with a toxin (see FIGS. 1 and 2), such that cells with high fucosylation activity would be eliminated.

LCA-biotin was added to bind to the cell surface. Streptavidin-Saporin was then added to the medium. Biotin-streptavidin interaction brings Saporin to the proximity of the cell membrane so that the complex could be internalized into the cells. Once inside the cells, Saporin can break away from the targeting agent and inactivate the ribosomes, leading to death.

To determine the optimal concentrations of LCA-biotin and streptavidin-saporin, to kill cells with high fucosylation activity efficiently, reduce nonspecific killing, thus resulting in cells with a variant glycosylation patter, the effects of different combinations of LCA-biotin and streptavidin-saporin concentrations on the killing of parental CHO-K1 cells was performed. LCA-biotin at a concentration of approximately 10 μg/ml and streptavidin-saporin at approximately 2

μg/ml was the optimal combination to kill a majority of the parental CHO-K1 cells (FIG. 3).

Example 2

Stability of Cell Line with Variant Glycosylation Pattern

Two chemical mutagens, ICR191 and ethyl methane sulfonate (EMS), were used to introduce random genomic mutations. CHO-K1 cells were treated with ICR191 or EMS, which typically cause frame shift mutations and guanine alkylation respectively. The chemicals were washed after 16 hours. The cells were allowed to recover for 5 days. The survived cells were selected with LCA-biotin at a concentration of 10 μg/ml and streptavidin-Saporin at 2 μg/ml for 4 weeks. The cells were routinely stained with FITC-LCA followed by FACS analysis. The sorted cells were cultured at a high density to expand their population and to obtain cells for subsequent LCA labeling and FACS sorting.

The selection gradually enriched a low-fucosylation population after ICR191 or EMS-induced mutagenesis (FIG. 4). After 4-week selection, the cells were grown in LCA-biotin and streptavidin-Saporin-free medium for more than two months. The acquired populations maintained their low fucosylation status without the presence of LCA-biotin and streptavidin-Saporin in the medium (FIG. 4A). In order to obtain stable cell clones as production lines, limiting dilution was used to seed the cells in 96-well plate and expand the single clones in LCA-biotin and streptavidin-Saporin-free medium. Cellular fucosylation status was monitored by FACs analysis every week for more than three months. These obtained clones demonstrated very stable low fucosylation for a long period of time and these clones had a cell growth rate comparable to parental cells. The stability of low fucosylation status in one of the clones is shown in FIG. 5. These results indicate that our random mutagenesis and selection strategy specifically enrich the low-fucosylation cells.

Example 3

Glycosylation Profile of Cell Line with Variant Glycosylation Pattern

Low fucosylation cell clones have a unique and consistent profile of a glycosylation pattern that is varied in comparison to an unmodified or parental cell line. This profile was established by staining the parental cells and low fucosylation clones with FITC-conjugated wheat germ agglutinin (WGA), which has preferential binding to N-acetylglucosamine, concanavalin A (Con A), which recognizes α-linked mannose, and *Griffonia* (Bandeiraea) *Simplicifolia* Lectin II (GS-II), which binds to α- or β-linked N-acetylglucosamine residues). The labeled cells were analyzed by FACS. The low fucosylation clones also have low binding affinity to WGA, suggesting that these clones have low levels of N-acetylglucosamine (FIG. 6). In contrast, the binding to Con A and GS-II of these clones was significantly higher than that of the control, indicating that these clones have much higher content of α-linked mannose and α- or β-linked N-acetylglucosamine (FIG. 6). The stability of this unique profile of the glycosylation pattern was also tested. These clones maintained the same profile when grown in LCA-biotin-free medium for more than 8 weeks (FIG. 5). A CHO-K1 mutant clone was grown in serum-free culture medium in suspension and had a similar N-glycan profile (FIG. 7).

Example 4

Glycosylation Profile of Antibody

Antibodies expressed in the cell lines with a variant glycosylation pattern have low fucose content. They also have a variant glycosylation pattern as shown in FIG. 9B. Humanized anti-ErbB2 antibody ET101 was expressed in the mutant CHO-K1 clone 1E5, which exhibits a variant glycosylation pattern. The 1E5 mutant clone was grown in serum-free suspension and had a similar level of gene transcripts of 1,6-fucsotyltransferase (Fut8) as compared to unmodified host cells (FIG. 8). Transcript level was determined by isolating total RNA from cells. The transcripts were reverse transcripted into cDNA and the Fut8 transcripts were amplified by RT-PCR. The PCR products were separated by electrophoresis in agarose gel and the level of actin was used as loading control.

The antibody was obtained from the conditioned media of the mutant clone 1E5. The expression of the antibody was determined by SDS-PAGE and Coomassie blue staining (FIG. 9A). Aliquots of samples run on SDS-PAGE were transferred to nitrocellulose membranes and blotted with biotinylated LCA, WGA, ConA, and GS-II, which binds preferentially to fucose linked (α-1,6) to N-acetylglucosamine, N-acetylglucosamine, α-linked mannose, and α- or β-linked acetylglucosamine, respectively. The same antibody was expressed in parental CHO-K1 cells as a control, as indicated in FIG. 9B as "CHO".

The results show that the antibodies produced by clone 1E5 were modified to have a variant glycosylation pattern with significantly reduced binding affinity to LCA, WGA, GSII, and increased binding affinity to ConA, as compared to the control (FIG. 9B)/Results indicate that the fucose content of the antibodies was drastically decreased.

The monosaccharide profile of the antibodies ET101 and ET201 produced by different CHO lines was also determined, as shown in FIG. 10A, B. The antibody ET101 or ET201 was produced in parental CHO cells, mutant CHO-1E5 clone, mutant CHO-3F clone, or mutant CHO-2.6 clone. All the CHO clones were adapted to grow in serum-free medium cultured in suspension. Monosaccharides were released from 1 mg of antibodies ET101 and ET201 by heating with 4 M trifluoroacetic acid at 100° C. for 2 hours. The monosaccharides were then dried under vacuum and reconstituted with water. The monosaccharides were analyzed by high performance ion exchange chromatography using DX-ISC-3000 system (DIONEX, Sunnyvale, Calif.). A CarboPac-PA-1 column (DIONEX, Sunnyvale, Calif.) was used to resolve monosaccharide with a flow rate of 0.8 ml/min at 35° C. After injection of the sample, the monosaccharides were resolved with 18 mM NaOH for 20 minutes, and the column was regenerated by elution with 200 mM NaOH for 10 minutes. The column was held 18 mM NaOH for 30 minutes prior to the next injection. Quantification of monosaccharides in ET101 produced by parental CHO and mutant clones is shown in FIG. 10A. Monosaccharide composition of human IgG1 (ET101 and ET201) produced by parental CHO cells and mutant clones is shown in FIG. 10B, showing a decrease in galactose levels and an increase in glucose levels for IgG1 produced in the mutant clones as compared to those produced in the parental cells.

Figures 10B, 10C:
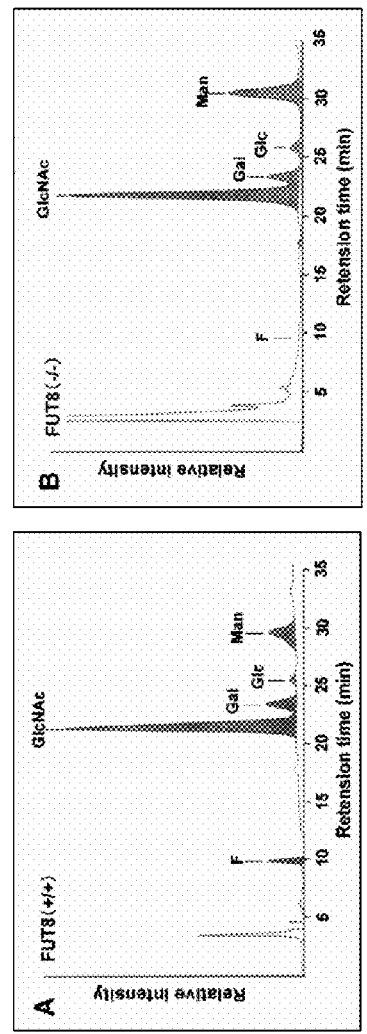

The monosaccharide composition analysis of human IgG1 produced by Fut8−/− knockout CHO cells as disclosed in Yamane-Ohnuki et al, *Biotechnol Biogeng.* 87:614-622 (2004) is shown in FIG. 10C, which shows galactose and glucose levels are relatively constant between the wild-type and Fut8−/− knockout CHO cells.

Example 5

Antibody with Enhanced ADCC Activity

Humanized anti-ErbB2 antibody was expressed in a mutant clone with a variant glycosylation pattern and compared to the antibody produced in a parental cell to demonstrate ErbB2-blocking antibody synthesized by cell lines possessed enhanced ADCC activity. To demonstrate enhanced ADCC activity, antibody-mediated lysis of A549, SKBR3, SKOV3, MDA-MB-361, and MDA-MB-231 cells were assessed to compare the efficiency of cytotoxcity. The target cells were pre-incubated with ErbB2-blocking antibodies (ET101 or ET201) produced from clone 1E5, 2.6, or 3F to allow the antibodies to bind with its target. Human PBMC were then incubated with the target cells. As shown in FIG. 11B, 12, 13, and 14, the control antibody could induce lysis of cells as expected, and variant glycosylation patterned cell-produced antibody significantly enhanced cell lysis, indicating that ADCC efficiency is enhanced by variant glycosylation patterned cell line-produced antibody.

Expressed antibody ET101 from 1 milliliter of conditioned media containing 10% FBS was precipitated by protein L beads, separated by a reducing SDS-PAGE gel and stained with Coomassie blue as shown in FIG. 11A. The blank growth medium was used as negative control. The ET101 antibody expressed in mutant clone was purified from the conditioned medium containing 10% FBS by Protein L chromatography, and quantified by UV280. Parental ET101 was expressed in wild type CHO and purified in the same way. Similar methods were used for obtaining ET201.

For ADCC assays as shown in FIGS. 1B, 12, 13, and 14, ET101 or ET201 antibody expressed in mutant clones was purified from the conditioned medium by Protein A chromatography and quantified by UV280. Parental ET101 or ET201 was expressed in wild type CHO and purified as the same way. 100 µl of target cell suspension was pre-incubated with 50 µl of the expressed ErbB2-blocking antibody ET101 in 96-well plate at 37° C. for half hour. 50 µl of PBMCs were then added at the effector/target cell ratio of 20:1. After incubation for 16 hours, the plate was spun down and 50 µl of cell-free supernatant was transferred to a new plate. The released lactate dehydrogenase (LDH) was measured by CytoTox96 Non-radioactive Cytotoxicity Assay (Promega, Madison, Wis.). The cell lysis was calculated by the formula (E−S)/(M−S) (E: experimental release, S: spontaneous release, M: maximal release). PBS or nonspecific antibody was used as negative control.

Example 6

Antibody Inhibits Cellular Proliferation

ErbB2-overexpressing breast cancer cell line SKBR3 is plated in 96-well plates for real time proliferation assay or in 24-well plates at a low density for colony formation assay. After allowing the cells to attach overnight, various concentrations of antibodies, control or various antibodies produced from cell clones with variant glycosylation patterns are added to the medium to test their inhibition on cell proliferation. The ErbB2 blocking antibodies produced from cell clones with variant glycosylation patterns inhibit cell proliferation comparable to, or to a greater extent than, control antibody (antibodies produced by parental cells). Cell proliferation inhibition is ascertained by methods such as colony formation assays, real time proliferation assays, or other methods known in the arts.

Example 7

Determination of Composition and Structure of the N-Glycan

To determine the components of the monosaccharides of the N-glycan, the antibody produced the CHO-1E5 cells and the antibody produced by the parental host cells in serum-free suspension were hydrolyzed with Trifluoroacetic Acid (TFA). The purified antibodies (100 µg) were mixed with Trifluoroacetic Acid (TFA) to the final concentration of TFA at 4M. The mixtures were boiled for two hours and the solutions were dried under vacuum. The pellets were dissolved in 200 µl of deionized water. 100 µl of the resuspended samples were injected into PA1 column to analyze the compositions of the monosaccharides by Dionex ICS-3000 system (Dionex, Sunnyvale, Calif.). As shown in FIG. 16, N-glycan synthesized by CHO-1E5 lacks galactose, has reduced fucose and N-acetylglucosamine, and possesses glucose molecule as compared to the N-glycan produced by the wild type parental host cells.

To further establish the composition of the N-glycan of the invention, the N-glycan was cleaved from the antibodies produced by CHO-1E5 and its parental host cells by PNGase F (New England Biolabs, Ipswich, Mass.). N-glycan was released by digesting 200 µg of antibody with PNGase F for 72 hours at 37° C. The protein was precipitated by 70% ethanol at −20° C. overnight and removed by centrifugation. The supernatants were dried under vacuum and resuspended in 200 µl of deionized water. The samples were loaded onto the microcolumns packed with C18 (Waters, Milford, Mass.), AG50WX8 and AG4x4 (BioRad Laboratories, Hercules, Calif.). The columns were then washed with 300 µl of deionozed water. The flowthrough was collected, dried under vacuum, and the N-glycan was then analyzed for MALDI-TOF MS using a MALDI-TOF MS spectrometer. The m/z value corresponds to the sodium-associated oligosaccharide ion. Each peak corresponds to [M+Na]$^+$. Two peaks were observed in the N-glycan from the antibody produced by the parental cells, which corresponds to the mass of G1 (Gal$_1$-Fuc$_1$-GlcNAC$_4$-Man$_3$) and G0 (Fuc$_1$-GlcNAC$_4$-Man$_3$) N-glycan (FIG. 17). In contrast, there is a single peak with the mass of 1257.4 in the N-glycan from the antibody synthesized by CHO-1E5 cells (FIG. 17). Combined with its composition of the monosaccharides (FIG. 16), the molecular composition of the N-glycan synthesized by CHO-1E5 was determined to be Glu-GlcNAC$_2$-Man$_4$ (+/−Fuc).

The single population of N-glycan synthesized by CHO-1E5 was further determined by oligosaccharide analysis. The N-glycan was released from the antibody and purified for MALDI-TOF MS analysis. Briefly, N-glycan was released by digesting 200 µg of antibody with PNGase F for 72 hours at 37° C. The protein was precipitated by 70% ethanol at −20° C. overnight and removed by centrifugation. The supernatants were dried under vacuum and resuspended in 200 µl of deionized water. The samples were loaded onto the microcolumns packed with C18, AG50WX8 and AG4x4. The columns were then washed with 300 µl of deionozed water. The flowthrough was collected and the oligosaccharide was injected into PA200 column and analyzed by Dionex ICS-3000 system. Consistent with the findings by MALDI-TOF MS analysis, the oligosaccharide from antibody produced by CHO-1E5 exists as a single peak and a substantially homogeneous population that is different from the heterogeneous profile of the oligosaccharides produced by the parental host cells (FIG. 18).

Based on the composition of the monosaccharides and the molecular weight of the N-glycan synthesized by CHO-1E5, 6 possible structures of the N-glycan were deduced (FIG. 19A and B). To further determine the structure of the N-glycan synthesized by CHO-1E5, different mannosidases were used to digest the N-glycan on the antibody and the released saccharide was analyzed by PA1 column/Dionex ICS-3000 system. α1,2 mannosidase (Prozyme, San Leandro, Calif.) was used to cleave the N-glycan synthesized by CHO-1E5 and the parental host cells to determine if there is α1,2 bond between mannoses. It is well established that α1,2 mannose bond does not exist in N-glycan produced by wild type CHO cells. There was no release of the saccharide from the antibodies after they were digested with α1,2 mannosidase, indicating that there was no α1,2 mannose bond existing in N-glycan synthesized by CHO-1E5. The enzymatic activity was confirmed using a positive control (oligomannose 9, Prozyme, San Leandro, Calif.). The N-glycans were then cut from the antibody with another enzyme, α1,2,3 mannosidase (New England Biolabs, Ipswich, Mass.) and the profile of the released saccharides was analyzed. Based on the classic structure of N-glycan synthesized by the wild type CHO cells, it was reasoned that there is only one cutting site of α1,3 mannose bond, and that this enzyme could release a disaccharide or trisaccharide (FIG. 20A). The antibodies (ET101) synthesized by CHO-1E5 and parental host cells were incubated with α1-2,3 mannosidase at 37° C. for 24 hours. To remove the antibody and the enzyme, the digested antibody solution was first passed through MicroCon YM10 (Millipore, Billerica, Mass.) and then MicroCon YM100 (Millipore, Billerica, Mass.). The sample was analyzed by PA1 column/Dionex ICS-3000 system. As shown in FIG. 20B and C, no monosaccharide was eluted by 18 mM NaOH and a peak corresponding to the elution time of disaccharide (sucrose) appeared when eluted by 90 mM NaOH. When the N-glycan on the antibody produced by CHO-1E5 was digested by α1-2, 3 mannosidase, a mannose was eluted by 18 mM NaOH and a disaccharide by 90 mM NaOH (FIG. 6D and E). The lack of α1,2 mannose bond and the profile of the saccharides released from CHO-1E5-produced antibody by α1,2,3 mannosidase suggest two structures that match the profile of the digestion by α1,2,3 mannosidase (FIG. 20F and G).

Example 8

N-Glycan Does Not Affect Antibody Assembly

As the alterations of protein glycosylation may affect protein folding and functional assembly, this issue was addressed by separating the antibody on SDS-PAGE electrophoresis. The purified antibodies produced by the parental host cells and CHO-1E5 were subjected to SDS-PAGE electrophoresis under reducing and non-reducing conditions, and stained with Coomassie Blue. As shown in FIG. 21, the migration of the monomers (both the light and heavy chains) and the whole antibody synthesized by CHO-1E5 is same as the antibody produced by the parental host cells under both reducing and non-reducing conditions, suggesting that the N-glycan produced by CHO-1E5 cells does not interfere with the functional assembly of the produced antibody.

Example 9

Antibody with Enhanced ADCC Activity and Higher Binding Affinity to FcγRIIIa

Figure 22A:
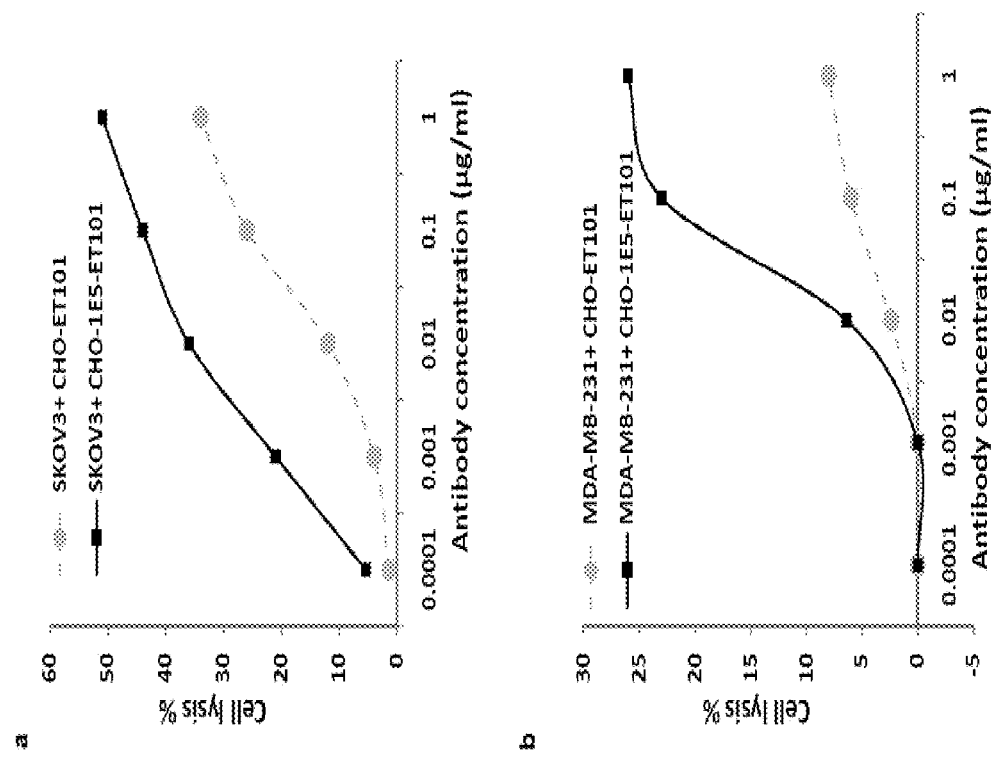

To determine if the modification of the antibody with the N-glycan of the invention could improve its biologic functions such as ADCC activity, two purified antibodies targeting ErbB2 and EGFR were used to test their ADCC activity in vitro (ET101 and ET201, respectively). ET101 antibody is an ErbB2-blocking IgG1. ET101 produced by CHO-1E5 cells was purified from the conditioned medium by Protein A chromatography; and quantified by UV280. Parental unmodified ET101 was expressed in wild-type CHO cells and purified in the same way. For ADCC assay, 100 μl of the target cell suspension was pre-incubated with 50 μl of the expressed ErbB2-blocking antibody ET101 in 96-well plate at 37° C. for half an hour. 50 μl of PBMCs were then added at the effector/target cell ratio of 20:1. After incubation for 16 hours, the plate was spun down and 50 μl of cell-free supernatants were transferred to a new plate. The released LDH was measured by CytoTox96 Non-radioactive Cytotoxicity Assay (Promega, Madison, Wis.). The cell lysis was calculated by the formula (E−S)/(M−S) (E: experimental release, S: spontaneous release, M: maximal release). PBS or nonspecific antibody was used as a negative control. The ADCC activity of ET101 exhibiting the N-glycan produced by CHO-1E5 cell clone in serum-free medium against the ovarian cancer cell line (SKOV3) and the breast cancer cell line (MDA-MB-231) was significantly enhanced as compared to that of the unmodified ET101 produced by the parental CHO cells (FIG. 22A).

Figure 22B:
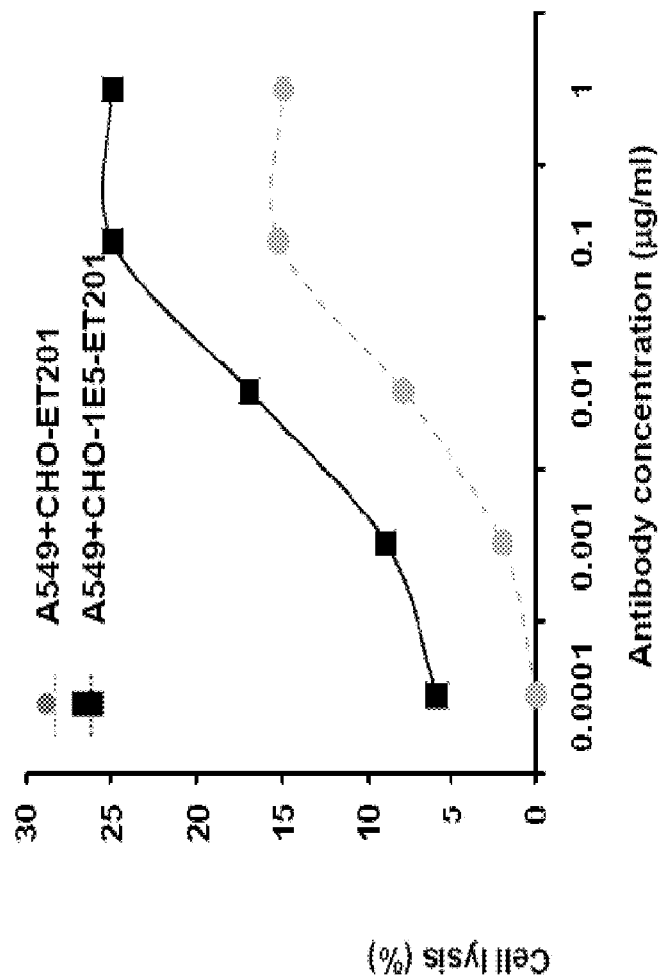

ET201 is an anti-EGFR antibody. ET201 expressed in CHO-1E5 cells was purified from the conditioned medium by Protein A chromatography and quantified by UV280. The ADCC assay was performed using the same method as described in FIG. 8A. The ADCC activity of ET201 exhibiting the N-glycan produced by CHO-1E5 cell clone in serum-free medium against the lung cancer cell line (A549) was enhanced as compared to that of the unmodified ET101 produced by the parental CHO cells (FIG. 22B).

To further identify how the N-glycan of the invention improves ADCC activity, recombinant FcγRIa and FcγRIIIa (R&D Systems, Minneapolis, Minn.) and ForteBio system (ForteBio, Menlo Park, Calif.) were used to measure the binding affinity of the antibody to these two Fc receptors. The antibodies were first biotinylated and loaded onto the streptavidin-coated biosensor (ForteBio, Menlo Park, Calif.). Recombinant FcγRI and FcγRIIIb proteins were suspended at the concentration of 100-400 nM (R&D Systems, Minneapolis, Minn.). The binding affinity ($K_D$, nM) was assessed according to ForteBio's standard kinetics protocol. The antibody produced by CHO-1E5 cells had increased binding affinity to FcγRIIIa as compared to the antibody produced by the parental CHO cells, although there was no significant difference in binding to FcγRIa (FIG. 23). These results indicate that the protein glycosylation by the N-glycan with the composition and the structures described herein confers the antibody with improved binding affinity to FcγRIIIa and an enhanced ADCC activity.

Example 10

Pharmacokinetics of the Antibody Exhibiting the N-Glycan

To further determine if the glycosylation by the N-glycan synthesized by CHO-1E5 cells could affect the pharmacokinetics of antibody in vivo, the antibodies produced by either parental host cells or by CHO-1E5 cells were injected into 13-week-old female Balb/c mice through the tail vein at 10 mg/kg, 3 mice for each antibody. 50 μl of blood were collected at 5 minutes, 1 hour, 6 hours, 72 hours and 120 hours. Serum concentration of the antibodies was monitored at 1, 6, 72 and 120 hours after the injection. The antibody concentration in the serum was measured by OCTET (ForteBio, Menlo Park, Calif.). The antibody concentration at the time of 5 minutes was considered as 100%. The pharmacokinetics of CHO-1E5-produced antibody is comparable to that of the antibody produced by the parental host cells (FIG. 24), indicating that the N-glycan of the invention does not affect the pharmacokinetics of the antibody in vivo.

Example 11

Further Structural Analysis of the Oligosaccharides Produced by CHO-1E5

To further validate the structures of the N-glycan synthesized by 1E5 cells, the high-quality N-glycan released by PNGase F was purified in large quantity, and the purified N-glycan and a positive control (Oligimannose 9, Glyko, San Leandro, Calif.) were digested with α1,2,3 mannosidase or α1,2,3,6 mannosidase, and the products of the digestion were analyzed by PA1 column and Dionex ICS-3000 system (Dionex, Sunnyvale, Calif.).

The antibodies (ET101) synthesized by 1E5 (A and C) and a positive control N-glycan (Band D)(oligomannose 9, Glyko, San Leandro, Calif.) were incubated with α1,2,3 mannosidase (A and B) or α1,2,3,6 mannosidase (C and D) at 37° C. for 24 hours. To remove the antibody and the enzyme, the digested antibody solution was first passed through the microcolumns packed with C18, AG50WX8 and AG4x4. The columns were then washed with 300 µl of deionozed water. The flowthrough was collected, dried under vacuum and analyzed by PA1 column/Dionex ICS-3000 system.

Two peaks were observed when the product of digestion was eluted by 18 mM NaOH. One peak was at 17 minutes, which corresponds to the elution time of a mannose standard. Another was at 24 minutes, which is similar to a disacharride standard (FIG. 25A). The digestion pattern by α1,2,3 mannosidase is consistent with the prediction of the two structures, i.e. Formulas 1 and 2 disclosed herein, and excludes the possibility of other putative structures as no mannose could be predicted to be released by α1,2,3 mannosidase digestion. The products of oligomannose 9 digestion by α1,2,3 mannosidase were consistent with the prediction (FIG. 25B). When digested by α1,2,3,6 mannosidase, three peaks, corresponding to the standards of mannose, disaccharide, and trisacharride, were eluted by 18 mM NaOH (FIG. 25C). The digestion pattern by α1,2,3,6 mannosidase was also consistent with the prediction of the structural formulas 1 and 2 (FIG. 25C). These data further establish that structural formulas 1 and 2 are the two final candidate structures of N-glycan synthesized by 1E5 cells. There is no available method to date to distinguish these two structures.

Example 12

Enhanced ADCC Against Cells Expressing the Low Affinity FcγRIIIa 158 F/F

Human FCγR IIIa has a polymorphism at amino acid 158. When the amino acid 158 is Valine at the two alleles, the FCγR IIIa has high affinity to the Fc fragment of IgG (termed FCγR IIIa 158V/V). When it is a Phenylalanine-carrier at amino acid 158, the binding affinity of the FCγR IIIa to the Fc fragment of IgG is low (FCγR IIIa 158F/F or 158F/V). The ADCC activity correlates positively with the FCγR IIIa binding affinity with the Fc fragment. The FCγR IIIa polymorphism of the PBMCs used in the ADCC assays was genotyped as shown previously.

For ADCC assay, 100 µl of the target cell suspension was pre-incubated with 50 µl of the expressed ErbB2-blocking antibody ET101 in 96-well plate at 37° C. for half an hour. 50 µl of PBMCs were then added at the effector/target cell ratio of 20:1. After incubation for 16 hours, the plate was spun down and 50 µl of cell-free supernatants were transferred to a new plate. The released LDH was measured by CytoTox96 Non-radioactive Cytotoxicity Assay (Promega, Madison, Wis.). The cell lysis was calculated by the formula (E−S)/(M−S) (E: experimental release, S: spontaneous release, M: maximal release). PBS or nonspecific antibody was used as a negative control. The genomic DNA was isolated from PMBCs used for these ADCC assays. The PCR assay to genotype the polymorphism of FcγR IIIa is according to the standard protocols in the art. The ADCC activity was measured against the ovarian cancer cell line (SKOV3) and the breast cancer cell line (MDA-MB-231). It was found that the antibody expressing the unique N-glycan produced by CHO-1E5 cells enhanced the ADCC activity equally efficiently when PBMCs of different genetic backgrounds expressing either the high-affinity FCγR IIIa 158V/V or the low-affinity FCγR IIIa 158F/F were used as the effector cells (FIGS. 26A and B). The ET101 antibody produced by CHO-1E5 cells bound to the low affinity FCγR IIIa 158F/F equally well and elicited a strong ADCC response.

Example 13

Antibody Produced by 1E5 Cells Exhibits Hither Binding Affinity to FcγRIIIa and Lower Binding Affinity to FCγR IIb as Compared to a Parental Antibody ADCC is a process that a specific antibody targeting a cell surface antigen first binds to the cell and the Fc fragment of that antibody then recruits the effector cells such as natural killer cells and monocytes to the target cells through Fc binding to the Fc receptors expressed on the cell surface of the effector cells. The recruitment brings the target and the effector cells to the proximity in order to kill the target cells by the effector cells. The Fc receptors (FCγR) consist of three types, I, II and III. FCγR Ia, FCγR IIa and FCγR IIIa are activating receptors that mediate and enhance ADCC when activated. FCγR IIb is an inhibitory receptor that blocks ADCC when activated. So an antibody with high affinity to FCγR Ia, FCγR IIa or FCγR IIIa has enhanced ADCC activity. However, an antibody with high affinity to FCγR IIb may inhibit ADCC activity and vice versa (FIG. 27).

In order to determine the mechanism of this enhanced ADCC activity by the antibodies produced by 1E5 cells, the binding affinity of the antibodies to FCγRs was assessed. Human full length FcγRIIIA and FcγRIIb were cloned into the expression vector and stably expressed in CHO-K1 cells. The cells were released from tissue culture dishes by 20 mM EDTA in PBS and disbursed into single cells. The cells were incubated with biotinylated antibodies at 10 µg/ml in PBS with 5% FBS on ice for 30 minutes. After washing with PBS for three times, the cells were incubated with FITC-conjugated streptadividin, analyzed by FACS and the mean fluorescence intensity (MFI) was acquired. The antibody binding affinity with inhibitory FcγRIIb (A) and activating FcγRIIIA (B) (at 10 µg/ml) and the mechanistic schemes are shown in FIG. 27.

CHO-K1 cell lines that stably overexpressed human Fcγ receptors including FCγRIIb and FCγR IIIa 158 (V/V type-high affinity) on the cell surface were established. By using FACS approach, the binding affinities of the antibodies produced by parental CHO cells and 1E5 cells with these Fcγ receptors were measured by quantifying the mean fluorescence intensity (MFI). It was found that the antibody produced by 1E5 cells has significantly reduced binding affinity with the inhibitory receptor, FCγR IIb, when compared to the antibody produced by parental CHO cells (FIGS. 27A and 28), suggesting that the inhibitory receptor is much less activated by the antibody produced by CHO-1E5 cells. Furthermore, the antibody produced by 1E5 cells had significantly increased binding affinity to the activating FCγR IIIa (FIGS. 27B and 28). The antibody produced by 1E5 cells had comparable binding affinities to FCγRI and the neonatal Fc receptor for IgG (FcRN) as the antibody produced by parental CHO cells (FIG. 28). These results suggest a mechanism that the enhanced ADCC activity by 1E5-produced antibody is mediated by increased activation of the activating FCγRIIIa and decreased activation of the inhibitory FCγR.

Example 14

Immunogenicity of Antibody Produced by CHO-1E5 cells

To assess immunogenicity of the antibody produced by CHO-1E5 cells exhibiting enhanced ADCC activity as compared to that of an antibody produced by unmodified parental CHO cells, in vivo immunogenicity of the subject antibodies is assessed by measuring titer of antibody specific against the subject antibodies in primates. Specifically, female cynomolgus monkeys of 3-5 years old weighing 4-6 kilograms (kg) receive anti-Her2 antibody ET101 produced by wild type CHO cells, or ET101 produced by CHO-1E5 cells at a dose of 8 mg/ml/kg of body weight. Two monkeys are in each group. 0.5 ml of blood is collected 7 days before the antibody injection and on days 3, 5, 7, 14, 21, 28, 35 after the antibody injection. Serum samples are isolated and frozen at −80° C. (FIG. 29A). ELISA is used to determine immunogenicity of ET101-CHO-1E5 antibody in cynomolgus monkeys. The assay detects the presence of IgM in the monkey serum specific for the administered ET-101 antibodies. An ELISA plate is coated with ET101-CHO or ET101-CHO-1E5 antibodies. The isolated monkey serum samples at different dilutions are applied to the coated plate to allow binding to the coated ET-101-CHO or ET-101-CHO-1E5 antibodies. The bound IgM is detected with an anti-IgM secondary antibody (FIG. 29B). The ELISA results show no significant difference in immunogenicity (i.e. ET101-specific IgM levels in monkey serum) between ET101-CHO and ET101-CHO-1E5 antibodies ((FIG. 29C). This example demonstrates that antibody produced by CHO-1E5 clone does not elicit higher immunogenicity than antibody produced by the wild type CHO cells.

The present disclosure is not limited to the embodiments described above, but is capable of modification within the scope of the appended claims. Those skilled in the art will recognize, or be able to ascertain using no more than routine experimentation, many equivalents of the specific embodiments of the present disclosure described herein.

What is claimed is:

1. An isolated mammalian glycoprotein, wherein said isolated mammalian glycoprotein exhibits a variant glycosylation pattern, wherein said variant glycosylation pattern comprises an N-linked glycan having a structure of formula (I) or (II):

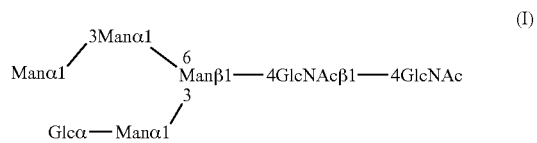

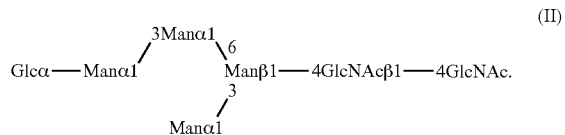

2. The isolated mammalian glycoprotein of claim 1, wherein said isolated mammalian glycoprotein is an antibody.

3. The isolated mammalian glycoprotein of claim 2, wherein said antibody exhibits an increased ADCC (antibody-dependent cell-mediated cytotoxicity) activity, as compared to a corresponding wildtype antibody.

4. The isolated mammalian glycoprotein of claim 1, wherein said isolated mammalian glycoprotein has a substantially homogeneous pattern of N-linked glycan, wherein said pattern of N-linked glycan is characterized by a single peak resolved by high performance liquid chromatography (HPLC).

5. The isolated mammalian glycoprotein of claim 1, wherein said isolated mammalian glycoprotein is produced by a host cell comprising a mammalian glycosylation system.

6. The isolated mammalian glycoprotein of claim 1, wherein said isolated mammalian glycoprotein comprises one or more fucose molecules.

* * * * *